US008410147B2

(12) United States Patent
Peterson et al.

(10) Patent No.: US 8,410,147 B2
(45) Date of Patent: Apr. 2, 2013

(54) METHOD FOR TREATING DISEASES ASSOCIATED WITH ALTERATIONS IN CELLULAR INTEGRITY USING RHO KINASE INHIBITOR COMPOUNDS

(75) Inventors: Ward M. Peterson, Morrisville, NC (US); John W. Lampe, Cary, NC (US); Tomas Navratil, Carrboro, NC (US); Scott D. Sorensen, Morrisville, NC (US); Emilee H. Fulcher, Cary, NC (US)

(73) Assignee: Inspire Pharmaceuticals, Inc., Whitehouse Station, NJ (US)

( * ) Notice: Subject to any disclaimer, the term of this patent is extended or adjusted under 35 U.S.C. 154(b) by 314 days.

(21) Appl. No.: 12/492,932

(22) Filed: Jun. 26, 2009

(65) Prior Publication Data

US 2009/0325905 A1   Dec. 31, 2009

Related U.S. Application Data

(60) Provisional application No. 61/075,846, filed on Jun. 26, 2008, provisional application No. 61/169,239, filed on Apr. 14, 2009, provisional application No. 61/169,639, filed on Apr. 15, 2009, provisional application No. 61/169,635, filed on Apr. 15, 2009.

(51) Int. Cl.
*A61K 31/41* (2006.01)
*A61K 31/40* (2006.01)
*A61K 31/405* (2006.01)

(52) U.S. Cl. ......... 514/359; 514/408; 514/410; 514/415

(58) Field of Classification Search .................. 514/359, 514/408, 410, 415
See application file for complete search history.

(56) References Cited

U.S. PATENT DOCUMENTS

| | | |
|---|---|---|
| 2004/0102437 A1 | 5/2004 | Takami et al. |
| 2005/0148640 A1 | 7/2005 | Come et al. |
| 2006/0167043 A1 | 7/2006 | Iwakubo et al. |
| 2008/0214614 A1 | 9/2008 | Lampe et al. |

FOREIGN PATENT DOCUMENTS

| | | |
|---|---|---|
| EP | 1541151 A1 | 6/2005 |
| WO | WO 01/56988 A1 | 8/2001 |
| WO | WO 2005/003101 A2 | 1/2005 |
| WO | WO 2005/034866 A2 | 4/2005 |
| WO | WO-2006135383 | 12/2006 |
| WO | WO 2008/077057 A2 | 6/2008 |
| WO | WO-2008077552 | 7/2008 |

OTHER PUBLICATIONS

Itoh K et al., "An essential part for Rho-associated kinase in the transcellular invasion of tumor cells," *Nature Medicine*, 5:221-5, 1999.
Ogawa T., "Rho-Associated Kinase Inhibitor Reduces Tumor Recurrence After Liver Transplantation in a Rat Hepatoma Model," *Am J Transplantation*, 7:347-355, 2007.
Shimizu et al., "Parallel Coiled-coil Association of the RhoA-binding Domain in Rho-kinase," *J. Biol. Chem.*, vol. 278, pp. 46046-46051, 2003.
Yamaguchi et al., "Structural Basis for Induced-Fit Binding of Rho-Kinase to the Inhibitor Y-27632." *J. Biochemistry*, vol. 140(3), pp. 305-311, 2006.
Ying H et al., "The Rho kinase inhibitor fasudil inhibits tumor progression in human and rat tumor models," *Mol Cancer Ther.*, 5:2158-2164, 2006.

*Primary Examiner* — Renee Claytor
(74) *Attorney, Agent, or Firm* — Perkins Coie LLP.; Viola T. Kung

(57) ABSTRACT

This invention is directed to methods of preventing or treating diseases or conditions associated with alterations in cellular integrity including alterations in endothelial permeability, excessive cell proliferation or tissue remodeling. Particularly, this invention is directed to methods of treating diabetic nephropathy, malaria, or cancer. The method comprises identifying a subject in need of the treatment, and administering to the subject an effective amount of a novel rho kinase inhibitor compound to treat the disease.

9 Claims, 10 Drawing Sheets

METHOD FOR TREATING DISEASES ASSOCIATED WITH ALTERATIONS IN CELLULAR INTEGRITY USING RHO KINASE INHIBITOR COMPOUNDS

This application claims the benefit of U.S. Provisional Application Nos. 61/075,846, filed Jun. 26, 2008; 61/169,239, filed Apr. 14, 2009; 61/169,639, filed Apr. 15, 2009; and 61/169,635, filed Apr. 15, 2009; which are incorporated herein by reference in their entirety.

TECHNICAL FIELD

This invention relates to methods of preventing or treating diseases or conditions associated with alterations in cellular integrity including endothelial permeability, excessive cell proliferation, tissue remodeling, and inflammation. Particularly, this invention relates to methods of treating diseases or conditions associated with alteration in endothelial permeability, excessive cell proliferation or tissue remodeling such as diabetic nephropathy, malaria, and cancer, using novel rho kinase inhibitor compounds.

BACKGROUND OF THE INVENTION

Rho Kinase as a Target

The Rho family of small GTP binding proteins can be activated by several extracellular stimuli such as growth factors, hormones and mechanic stress and function as a molecular signaling switch by cycling between an inactive GDP-bound form and an active GTP-bound form to elicit cellular responses. Rho kinase (ROCK) functions as a key downstream mediator of Rho and exists as two isoforms (ROCK 1 and ROCK 2) that are ubiquitously expressed. ROCKs are serine/threonine kinases that regulate the function of a number of substrates including cytoskeletal proteins such as adducin, moesin, $Na^+$-$H^+$ exchanger 1 (NHE1), LIM-kinase and vimentin, contractile proteins such as the myosin light chain phosphatase binding subunit (MYPT-1), CPI-17, myosin light chain and calponin, microtubule associated proteins such as Tau and MAP-2, neuronal growth cone associate proteins such as CRMP-2, signaling proteins such as PTEN and transcription factors such as serum response factor (Loirand et al, Circ Res 98:322-334 (2006)). ROCK is also required for cellular transformation induced by RhoA. As a key intermediary of multiple signaling pathways, ROCK regulates a diverse array of cellular phenomena including cytoskeletal rearrangement, actin stress fiber formation, proliferation, chemotaxis, cytokinesis, cytokine and chemokine secretion, endothelial or epithelial cell junction integrity, apoptosis, transcriptional activation and smooth muscle contraction. As a result of these cellular actions, ROCK regulates physiologic processes such as vasoconstriction, bronchoconstriction, tissue remodeling, inflammation, edema, platelet aggregation and proliferative disorders.

One well documented example of ROCK activity is in smooth muscle contraction. In smooth muscle cells ROCK mediates calcium sensitization and smooth muscle contraction. Agonists (noradrenaline, acetylcholine, endothelin, etc.) that bind to G protein coupled receptors produce contraction by increasing both the cytosolic $Ca^{2+}$ concentration and the $Ca^{2+}$ sensitivity of the contractile apparatus. The $Ca^{2+}$-sensitizing effect of smooth muscle constricting agents is ascribed to ROCK-mediated phosphorylation of MYPT-1, the regulatory subunit of myosin light chain phosphatase (MLCP), which inhibits the activity of MLCP resulting in enhanced phosphorylation of the myosin light chain and smooth muscle contraction (WO 2005/003101A2, WO 2005/034866A2).

The use of prototype non-potent Rho-kinase inhibitors, Y27632 or fasudil, in animal models has suggested a number of potential benefits of Rho-kinase inhibitors, Y27632 has shown favorable activity in animal models of neoplasias and tumor metastasis (Ogawa T *Am J Transplantation* 7:347-355, 2007). Fasudil has been shown to have favorable activity in models of tumor growth and metastasis (Ying H et al. *Mol Cancer Ther* 5:2158-64, 2006). In addition, fasudil has been shown to provide benefits for controlling cerebral vasospasms and ischemia following subarachnoid hemorrhage in humans.

Diabetic Nephropathy

Diabetic Nephropathy (also known as Kimmelstiel-Wilson disease and intercapillary glomerulosclerosis) is kidney disease or damage that results as a complication of diabetes. It is the leading cause of death and disability in diabetes, and is characterized by nephrotic syndrome and nodular glomerulosclerosis. (Adler et al., Secondary Glomerular Diseases, in *The Kidney*. 5th, BM Brenner (ed). Pages 1498-1596). Diabetic nephropathy complicates approximately 20-30% of type 1 and type 2 diabetes mellitus and is clinically diagnosed by proteinuria and progressive renal insufficiency. Diabetic nephropathy is the leading cause of end-stage renal diseases in western societies and accounts for 30-35% of patients on renal replacement therapy. The exact cause of diabetic nephropathy is unknown, but it is believed that uncontrolled high blood sugar leads to the development of kidney damage. Diabetic nephropathy is a prime cause for dialysis in many Western countries (Parving et al., Diabetic Nephropathy, in *The Kidney*. 5th ed. B M Brenner (ed) Pages 1864-1892. (1996)).

A growing body of evidence suggests that the RhoA/ROCK pathway may have modulatory effects on the renal system. RhoA/ROCK pathway has been shown to play an important role in renal fibrosis by enhancing signaling pathways involving transforming growth factor-β, angiotensin II, and nuclear factor-κ B (Heusinger-Ribeiro, et al., *J Am Soc Nephrol* 12:1853-1861 (2001); Sharpe, et al., *J Am Soc Nephrol* 14:261-264 (2003)) as well as in VEGF-induced glomerular endothelial cell hyperpermeability (Kolavennu, et al., *Diabetes* 57:714-723 (2008)). Fasudil and Y-27632, two selective ROCK inhibitors not of Formula I or II, have been shown to improve outcomes in a variety of renal injury models in animals, including unilateral ureteral obstruction (Nagatoya, et al., *Kidney Int* 61:1684-1695 (2002)), hypertensive glomerulosclerosis (Kanda, et al., *Kidney Int* 64:2009-2019 (2003)) and ischemia/reperfusion-induced acute renal failure (Teraishi et al., *Eur J Pharmacol* 505:205-211, (2004)).

Optimization of glycemic control and inhibition of the renin-angiotensin system (RAS) are the mainstays of management of diabetic nephropathy, but renal damage progresses in many patients despite these measures (Bach, *Diabetes* 57:532-3 (2008)). Improved approaches to treating nephropathy are therefore required.

Malaria

Malaria currently represents one of the most prevalent infections in tropical and subtropical areas throughout the world. Per year, malaria infections kill up to 2.7 million people in developing and emerging countries. Malaria is caused by mosquito-borne hematoprotozoan parasites belonging to the genus *Plasmodium*. There are four species of *Plasmodium* protozoa (*P. falciparum, P. vivax, P. ovale* and *P. malariae*) that are responsible for the disease in man, The symptoms of uncomplicated malaria include fever, malaise, fatigue, muscle aches, back pain, headache, dizziness, loss of appetite, nausea, vomiting, abdominal pain, and diarrhea. Malaria may cause anemia and jaundice due to the destruction of red blood cells. *P. falciparum* accounts for the majority of infections in humans and is the most lethal type because the disease can progress to cerebral malaria. Cerebral malaria mostly affects young children and pregnant women in sub-saharan Africa, whereas multi-organ failure is seen mainly in adults in South East Asia. Severe malaria cases may then progress rapidly, often within 24 hours, to coma and death if left untreated. The current standard of treatment is with anti-malarials or quinine. Antimalarials resistance has become a significant problem, and while combination therapies and quinine treatments offer some solution, combination therapies are often more expensive while quinine has greater side effect risks such as causing birth defects in pregnant women. The complex life cycle of the parasite and its constantly changing antigens have thus far prohibited vaccine development (Greenwood B et al. *J Clin Invest*, 118(4): 1266-1276, 2008). Therefore, there is a significant need for novel malarial therapies.

Endothelial activation is believed to play a crucial role in *P. falciparum* malaria acute phase severity. *P. falciparum* cytoadherence is known to induce proinflammatory endothelial responses via NF-kappaB signaling cascades. In addition, adherence of parasitized cells or of parasites at the surface of uninfected target endothelial cells is known to induce the activation of Rho kinase through membrane borne adhesion molecules. Members of the Rho family of small GTPases are known to play a pivotal role in the signal transmission of various receptors, including ICAM-1, vascular cell adhesion molecule (VCAM)-1 and selectins involved in cytoadherence and in the formation of focal adhesions (Taoufiq Z et al. *J. Infectious Diseases*, 197:1062-1073, 2008). In endothelial cells adhered by infected erythrocytes, activation of Rho kinase leads to Akt kinase inhibition and apoptosis of the endothelial cells and these effect are inhibited by fasudil, a known Rho kinase inhibitor compound not of Formula I or II.

Cancer

Cancer is the second most common cause of death in the US, exceeded only by heart disease. In the US, cancer accounts for 1 of every 4 deaths. This year, about 565,650 Americans are expected to die of cancer, more than 1,500 people a day. Cancer is a term that identifies a group of diseases characterized by uncontrolled growth of abnormal cells that are able to invade other tissues. In cancer patients, malignant tumors undergo extensive invasion and metastasis, the extent of which negatively impacts their prognosis and benefit from therapy. Metastasis of tumors and complications thereof, are the primary cause for cancer mortality. There is a great need to identify molecular pathways that are necessary for tumor invasion and metastasis and develop pharmacological agents that could effectively inhibit or block these processes (Ying H et al. *Mol Cancer Ther*, 5:2158-2164, 2006).

The ability of cancer cells to undergo invasion and migration is a prerequisite for tumor metastasis. The effects of a representative Rho kinase inhibitor compound, Y-27632, not of Formula I or II on the in vitro invasion of LPA-stimulated MM1 cells are to inhibit the migration of MM1 cells in a concentration dependent manner. The relative potencies of these compounds for inhibition of invasion were consistent with their inhibition constants (Ki) for inhibition of the kinase activity of ROCK in vitro (Itoh K et al. *Nature Medicine*, 5:221-5, 1999). Similarly, fasudil, another Rho kinase inhibitor compound not of Formula I or II has been shown to inhibit in vivo tumor progression in rodent model via alterations in cell migration and cell growth (Ying H et al. *Mol Cancer Ther*, 5:2158-2164, 2006).

There is a need for an effective or improved method for treating diseases or conditions associated with alteration in cellular integrity, permeability, proliferation or remodeling such as diabetic nephropathy, malaria, and cancer.

SUMMARY OF THE INVENTION

The present invention is directed to methods of preventing or treating diseases or conditions associated with alterations in endothelial permeability, excessive cell proliferation, remodeling, inflammation, and cell motility. Particularly, this invention relates to methods of treating diseases or conditions associated with alterations in endothelial permeability, excessive cell proliferation or remodeling such as diabetic nephropathy, malaria, and cancer, using novel rho kinase inhibitor compounds.

The method comprises identifying a subject suffering from diabetic nephropathy, malaria, or cancer, and administering to the subject an effective amount of a novel rho kinase inhibitor compound of Formula II to treat diabetic nephropathy, malaria, or cancer.

The active compound is delivered to a subject by systemic administration or local administration.

DETAILED DESCRIPTION OF THE INVENTION

Definitions

Figure 1:
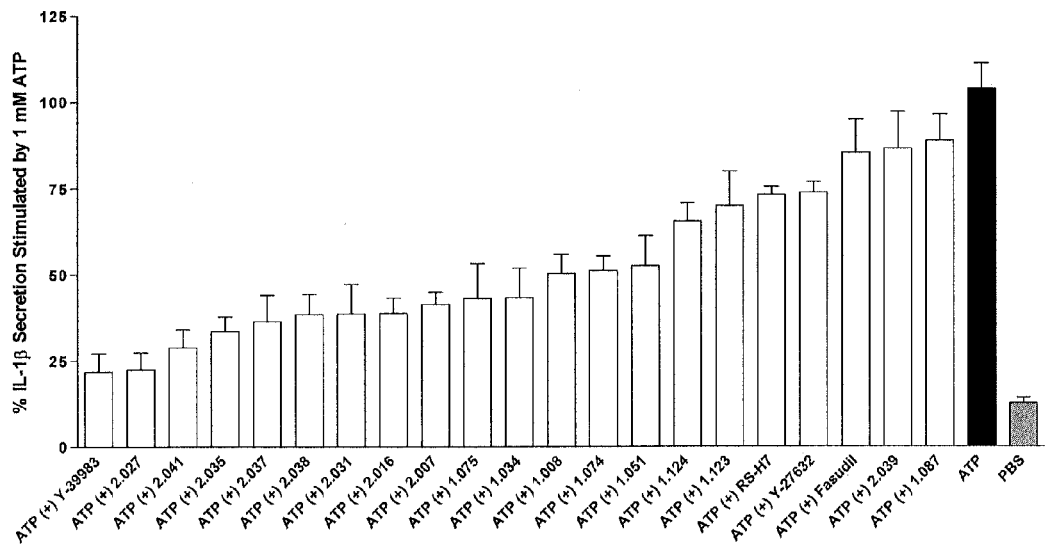
FIG. 1 shows the % inhibition of IL-1β Secretion in Human Monocytes by Rho Kinase Inhibitors. Data represent the mean±SD of at least n=2 experiments.

When present, unless otherwise specified, the following terms are generally defined as, but are not limited to, the following:

Halo substituents are taken from fluorine, chlorine, bromine, and iodine.

"Alkyl" refers to groups of from 1 to 12 carbon atoms inclusively, either straight chained or branched, more preferably from 1 to 8 carbon atoms inclusively, and most preferably 1 to 6 carbon atoms inclusively.

"Alkenyl" refers to groups of from 2 to 12 carbon atoms inclusively, either straight or branched containing at least one double bond but optionally containing more than one double bond.

"Alkynyl" refers to groups of from 2 to 12 carbon atoms inclusively, either straight or branched containing at least one triple bond but optionally containing more than one triple bond, and additionally optionally containing one or more double bonded moieties.

"Alkoxy" refers to the group alkyl-O— wherein the alkyl group is as defined above including optionally substituted alkyl groups as also defined above.

"Alkenoxy" refers to the group alkenyl-O— wherein the alkenyl group is as defined above including optionally substituted alkenyl groups as also defined above.

"Alkynoxy" refers to the group alkynyl-O— wherein the alkynyl group is as defined above including optionally substituted alkynyl groups as also defined above.

"Aryl" refers to an unsaturated aromatic carbocyclic group of from 6 to 14 carbon atoms inclusively having a single ring (e.g., phenyl) or multiple condensed rings (e.g., naphthyl or anthryl). Preferred aryls include phenyl, naphthyl and the like.

"Arylalkyl" refers to aryl-alkyl- groups preferably having from 1 to 6 carbon atoms inclusively in the alkyl moiety and from 6 to 10 carbon atoms inclusively in the aryl moiety. Such arylalkyl groups are exemplified by benzyl, phenethyl and the like.

"Arylalkenyl" refers to aryl-alkenyl- groups preferably having from 2 to 6 carbon atoms in the alkenyl moiety and from 6 to 10 carbon atoms inclusively in the aryl moiety.

"Arylalkynyl" refers to aryl-alkynyl- groups preferably having from 2 to 6 carbon atoms inclusively in the alkynyl moiety and from 6 to 10 carbon atoms inclusively in the aryl moiety.

"Cycloalkyl" refers to cyclic alkyl groups of from 3 to 12 carbon atoms inclusively having a single cyclic ring or multiple condensed rings which can be optionally substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures such as adamantyl, and the like.

"Cycloalkenyl" refers to cyclic alkenyl groups of from 4 to 12 carbon atoms inclusively having a single cyclic ring or multiple condensed rings and at least one point of internal unsaturation, which can be optionally substituted with from 1 to 3 alkyl groups. Examples of suitable cycloalkenyl groups include, for instance, cyclobut-2-enyl, cyclopent-3-enyl, cyclooct-3-enyl and the like.

"Cycloalkylalkyl" refers to cycloalkyl-alkyl- groups preferably having from 1 to 6 carbon atoms inclusively in the alkyl moiety and from 6 to 10 carbon atoms inclusively in the cycloalkyl moiety. Such cycloalkylalkyl groups are exemplified by cyclopropylmethyl, cyclohexylethyl and the like.

"Cycloalkylalkenyl" refers to cycloalkyl-alkenyl- groups preferably having from 2 to 6 carbon atoms inclusively in the alkenyl moiety and from 6 to 10 carbon atoms inclusively in the cycloalkyl moiety. Such cycloalkylalkenyl groups are exemplified by cyclohexylethenyl and the like.

"Cycloalkylalkynyl" refers to cycloalkyl-alkynyl- groups preferably having from 2 to 6 carbon atoms inclusively in the alkynyl moiety and from 6 to 10 carbon atoms inclusively in the cycloalkyl moiety. Such cycloalkylalkynyl groups are exemplified by cyclopropylethynyl and the like.

"Heteroaryl" refers to a monovalent aromatic heterocyclic group of from 1 to 10 carbon atoms inclusively and 1 to 4 heteroatoms inclusively selected from oxygen, nitrogen and sulfur within the ring. Such heteroaryl groups can have a single ring (e.g., pyridyl or furyl) or multiple condensed rings (e.g., indolizinyl or benzothienyl).

"Heteroarylalkyl" refers to heteroaryl-alkyl- groups preferably having from 1 to 6 carbon atoms inclusively in the alkyl moiety and from 6 to 10 atoms inclusively in the heteroaryl moiety. Such heteroarylalkyl groups are exemplified by pyridylmethyl and the like.

"Heteroarylalkenyl" refers to heteroaryl-alkenyl- groups preferably having from 2 to 6 carbon atoms inclusively in the alkenyl moiety and from 6 to 10 atoms inclusively in the heteroaryl moiety.

"Heteroarylalkynyl" refers to heteroaryl-alkynyl- groups preferably having from 2 to 6 carbon atoms inclusively in the alkynyl moiety and from 6 to 10 atoms inclusively in the heteroaryl moiety.

"Heterocycle" refers to a saturated or unsaturated group having a single ring or multiple condensed rings, from 1 to 8 carbon atoms inclusively and from 1 to 4 hetero atoms inclusively selected from nitrogen, sulfur or oxygen within the ring. Such heterocyclic groups can have a single ring (e.g., piperidinyl or tetrahydrofuryl) or multiple condensed rings (e.g., indolinyl, dihydrobenzofuran or quinuclidinyl). Preferred heterocycles include piperidinyl, pyrrolidinyl and tetrahydrofuryl.

"Heterocycle-alkyl" refers to heterocycle-alkyl- groups preferably having from 1 to 6 carbon atoms inclusively in the alkyl moiety and from 6 to 10 atoms inclusively in the heterocycle moiety. Such heterocycle-alkyl groups are exemplified by morpholino-ethyl, pyrrolidinylmethyl, and the like.

"Heterocycle-alkenyl" refers to heterocycle-alkenyl-groups preferably having from 2 to 6 carbon atoms inclusively in the alkenyl moiety and from 6 to 10 atoms inclusively in the heterocycle moiety.

"Heterocycle-alkynyl" refers to heterocycle-alkynyl-groups preferably having from 2 to 6 carbon atoms inclusively in the alkynyl moiety and from 6 to 10 atoms inclusively in the heterocycle moiety.

Examples of heterocycles and heteroaryls include, but are not limited to, furan, thiophene, thiazole, oxazole, pyrrole, imidazole, pyrazole, pyridine, pyrazine, pyrimidine, pyridazine, indolizine, isoindole, indole, indazole, purine, quinolizine, isoquinoline, quinolme, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, pyrrolidine, indoline and the like.

Unless otherwise specified, positions occupied by hydrogen in the foregoing groups can be further substituted with substituents exemplified by, but not limited to, hydroxy, oxo, nitro, methoxy, ethoxy, alkoxy, substituted alkoxy, trifluoromethoxy, haloalkoxy, fluoro, chloro, bromo, iodo, halo, methyl, ethyl, propyl, butyl, alkyl, alkenyl, alkynyl, substituted alkyl, trifluoromethyl, haloallyl, hydroxyallyl, alkoxyalkyl, thio, alkylthio, acyl, carboxy, alkoxycarbonyl, carboxamido, substituted carboxamido, alkylsulfonyl, alkylsulfinyl, alkylsulfonylamino, sulfonamido, substituted sulfonamido, cyano, amino, substituted amino, alkylamino, dialkylamino, aminoalkyl, acylamino, amidino, amidoximo, hydroxamoyl, phenyl, aryl, substituted aryl, aryloxy, arylalkyl, arylalkenyl, arylalkynyl, pyridyl, imidazolyl, heteroaryl, substituted heteroaryl, heteroaryloxy, heteroarylalkyl, heteroarylalkenyl, heteroarylalkynyl, cyclopropyl, cyclobutyl, cyclopentyl, cyclohexyl, cycloalkyl, cycloalkenyl, cycloalkylalkyl, substituted cycloalkyl, cycloalkyloxy, pyrrolidinyl, piperidinyl, morpholino, heterocycle, (heterocycle)oxy, and (heterocycle)alkyl; and preferred heteroatoms are oxygen, nitrogen, and sulfur. It is understood that where open valences exist on these substituents they can be further substituted with alkyl, cycloalkyl, aryl, heteroaryl, and/or heterocycle groups, that where these open valences exist on carbon they can be further substituted by halogen and by oxygen-, nitrogen-, or sulfur-bonded substituents, and where multiple such open valences exist, these groups can be joined to form a ring, either by direct formation of a bond or by formation of bonds to a new heteroatom, preferably oxygen, nitrogen, or sulfur. It is further understood that the above subtitutions can be made provided that replacing the hydrogen with the substituent does not introduce unacceptable instability to the molecules of the present invention, and is otherwise chemically reasonable.

The term "heteroatom-containing substituent" refers to substituents containing at least one non-halogen heteroatom. Examples of such substituents include, but are not limited to, hydroxy, oxo, nitro, methoxy, ethoxy, alkoxy, substituted alkoxy, trifluoromethoxy, haloalkoxy, hydroxyalkyl, alkoxyalkyl, thio, alkylthio, acyl, carboxy, alkoxycarbonyl, carboxamido, substituted carboxamido, alkylsulfonyl, alkylsulfinyl, alkylsulfonylamino, sulfonamido, substituted sulfonamido, cyano, amino, substituted amino, alkylamino, dialkylamino, aminoalkyl, acylamino, amidino, amidoximo, hydroxamoyl, aryloxy, pyridyl, imidazolyl, heteroaryl, substituted heteroaryl, heteroaryloxy, heteroarylalkyl, heteroarylalkenyl, heteroarylalkynyl, cycloalkyloxy, pyrrolidinyl, piperidinyl, morpholino, heterocycle, (heterocycle)oxy, and (heterocycle)alkyl; and preferred heteroatoms are oxygen, nitrogen, and sulfur. It is understood that where open valences exist on these substituents they can be further substituted with alkyl, cycloalkyl, aryl, heteroaryl, and/or heterocycle groups, that where these open valences exist on carbon they can be further substituted by halogen and by oxygen-, nitrogen-, or sulfur-bonded substituents, and where multiple such open valences exist, these groups can be joined to form a ring, either by direct formation of a bond or by formation of bonds to a new heteroatom, preferably oxygen, nitrogen, or sulfur. It is further understood that the above substitutions can be made provided that replacing the hydrogen with the substituent does not introduce unacceptable instability to the molecules of the present invention, and is otherwise chemically reasonable.

"Pharmaceutically acceptable salts" are salts that retain the desired biological activity of the parent compound and do not impart undesired toxicological effects. Pharmaceutically acceptable salt forms include various polymorphs as well as the amorphous form of the different salts derived from acid or base additions. The acid addition salts can be formed with inorganic or organic acids. Illustrative but not restrictive examples of such acids include hydrochloric, hydrobromic, sulfuric, phosphoric, citric, acetic, propionic, benzoic, napthoic, oxalic, succinic, maleic, fumaric, malic, adipic, lactic, tartaric, salicylic, methanesulfonic, 2-hydroxyethanesulfonic, toluenesulfonic, benzenesulfonic, camphorsulfonic, and ethanesulfonic acids. The pharmaceutically acceptable base addition salts can be formed with metal or organic counterions and include, but are not limited to, alkali metal salts such as sodium or potassium; alkaline earth metal salts such as magnesium or calcium; and ammonium or tetraalkyl ammonium salts, i.e., $NX_4^+$ (wherein X is $C_{1-4}$).

"Tautomers" are compounds that can exist in one or more forms, called tautomeric forms, which can interconvert by way of a migration of one or more hydrogen atoms in the compound accompanied by a rearrangement in the position of adjacent double bonds. These tautomeric forms are in equilibrium with each other, and the position of this equilibrium will depend on the exact nature of the physical state of the compound. It is understood that where tautomeric forms are possible, the current invention relates to all possible tautomeric forms.

"Solvates" are addition complexes in which a compound of Formula I or Formula II is combined with a pharmaceutically acceptable cosolvent in some fixed proportion. Cosolvents include, but are not limited to, water, methanol, ethanol, 1-propanol, isopropanol, 1-butanol, isobutanol, tert-butanol, acetone, methyl ethyl ketone, acetonitrile, ethyl acetate, benzene, toulene, xylene(s), ethylene glycol, dichloromethane, 1,2-dichloroethane, N-methylformamide, N,N-dimethylformamide, N-methylacetamide, pyridine, dioxane, and diethyl ether. Hydrates are solvates in which the cosolvent is water. It is to be understood that the definitions of compounds in Formula I and Formula II encompass all possible hydrates and solvates, in any proportion, which possess the stated activity.

The term "edema" refers to an abnormal accumulation of extra-vascular fluid.

The term "inflammation" generally refers to a localized reaction of tissue, characterized by the influx of immune cells, which occurs in reaction to injury or infection.

"An effective amount" is the amount effective to treat a disease by ameliorating the pathological condition or reducing the symptoms of the disease. "An effective amount" is the amount effective to improve at least one of the parameters relevant to measurement of the disease.

The inventors of the present invention have discovered that compounds of Formula I or II, which are Rho kinase inhibitors, are effective in reducing cell proliferation, decreasing remodeling that is defined by cell migration and/or proliferation, reducing inflammation via the inhibition of leukocytes chemotaxis and the inhibition of cytokine and chemokine secretion, lowering or preventing tissue or organ edema via the increase of endothelial cell junction integrity. By having the above properties, compounds of Formula I or II are useful in a method of preventing or treating diabetic nephropathy, malaria, or cancer.

The invention provides a method of reducing excessive cell proliferation, a method of decreasing remodeling that is defined by cell migration and/or proliferation, a method of reducing inflammation via inhibition of leukocytes chemotaxis and via decreasing cytokine and chemokine secretion, a method of lowering or preventing tissue or organ edema via increasing endothelial and epithelial cell junction integrity. By resolving one or more of the above-described pathophysiologies, the present invention provides a method of treating diseases associated with alterations in cellular integrity, particularly diabetic nephropathy, malaria, or cancer.

The present method comprises the steps of identifying a subject in need of treatment for the above conditions, and administering to the subject an effective amount of rho kinase inhibitor compound of Formula I or II.

Rho Kinase Inhibitor Compounds

The rho kinase inhibitor compounds useful for this invention include compounds of general Formula I and Formula II, and/or tautomers thereof, and/or pharmaceutically-acceptable salts, and/or solvates, and/or hydrates thereof. Compounds of general Formula I and Formula II can be prepared according to the methods disclosed in co-pending application US2008/0214614, which is incorporated herein by reference.

A compound according to Formula I or Formula II can exist in several diastereomeric forms. The general structures of Formula I and Formula II include all diastereomeric forms of such materials, when not specified otherwise. Formula I and Formula II also include mixtures of compounds of these Formulae, including mixtures of enantiomers, diastereomers and/or other isomers in any proportion.

A. Formula I

Compounds of Formula I are as follows:

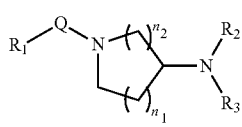

Formula I wherein: $R_1$ is aryl or heteroaryl, optionally substituted;
Q is C=O, $SO_2$, or $(CR_4R_5)_{n3}$;
$n_1$ is 1, 2, or 3;
$n_2$ is 1 or 2;
$n_3$ is 0, 1, 2, or 3;

wherein the ring represented by

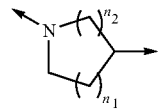

is optionally substituted by alkyl, halo, oxo, $OR_6$, $NR_6R_7$, or $SR_6$;
$R_2$ is selected from the following heteroaryl systems optionally substituted:

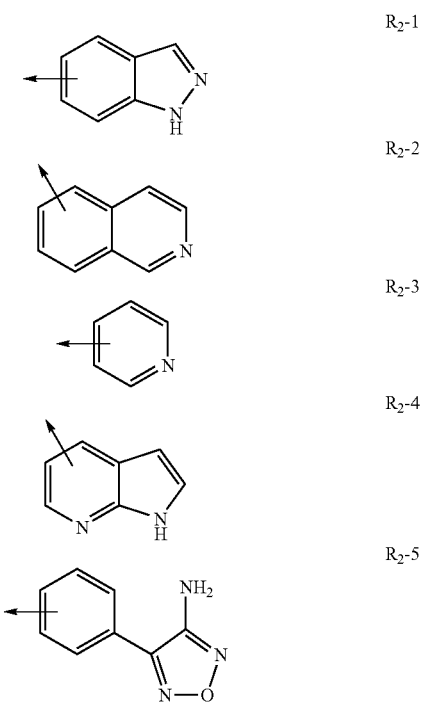

$R_3$-$R_7$ are independently H, alkyl, alkenyl, alkynyl, cycloalkyl, cycloalkenyl, cycloalkylalkyl, cycloalkylalkenyl, or cycloalkylalkynyl optionally substituted.

In Formula I, a preferred $R_1$ is substituted aryl, a more preferred $R_1$ is substituted phenyl, the preferred Q is $(CR_4R_5)_{n3}$, the more preferred Q is $CH_2$, the preferred n1 is 1 or 2, the preferred n2 is 1, the preferred $n_3$ is 1 or 2, and the preferred $R_3$-$R_7$ are H.

In Formula I, a preferred $R_2$ substituent is halo, alkyl, cycloalkyl, hydroxyl, alkoxy, cycloalkyloxy, amino, alkylamino, or $R_2$ is unsubstituted. A more preferred $R_2$ substituent is halo, methyl, ethyl, isopropyl, cyclopropyl, hydroxyl, methoxy, ethoxy, amino, methylamino, dimethylamino, or $R_2$ is unsubstituted.

[1] One embodiment of the invention is represented by Formula I, in which $R_2$ is 5-indazolyl or 6-indazolyl($R_2$-1), optionally substituted.

[1a] In embodiment 1, $R_2$-1 is substituted by one or more alkyl or halo substituents.

[1b] In embodiment 1, $R_2$-1 is substituted by one or more amino, alkylamino, hydroxyl, or alkoxy substituents.

[1c] In embodiment 1, $R_2$-1 is unsubstituted.

[2] In another embodiment, the invention is represented by Formula I in which $R_2$ is 5-isoquinolinyl or 6-isoquinolinyl ($R_2$-2), optionally substituted.

[2a] In embodiment 2, $R_2$-2 is substituted by one or more alkyl or halo substituents.
[2b] In embodiment 2, $R_2$-2 is substituted by one or more amino, alkylamino, hydroxyl, or alkoxy substituents.
[2c] In embodiment 2, $R_2$-2 is unsubstituted.
[3] In another embodiment, the invention is represented by Formula I in which $R_2$ is 4-pyridyl or 3-pyridyl($R_2$-3), optionally substituted.
[3a] In embodiment 3, $R_2$-3 is substituted by one or more alkyl or halo substituents.
[3b] In embodiment 3, $R_2$-3 is substituted by one or more amino, alkylamino, hydroxyl, or alkoxy substituents.
[3c] In embodiment 3, $R_2$-3 is unsubstituted.
[4] In another embodiment, the invention is represented by Formula I in which $R_2$ is 7-azaindol-4-yl or 7-azaindol-5-yl($R_2$-4), optionally substituted.
[4a] In embodiment 4, $R_2$-4 is substituted by one or more alkyl or halo substituents.
[4b] In embodiment 4, $R_2$-4 is substituted by one or more amino, alkylamino, hydroxyl, or alkoxy substituents.
[4c] In embodiment 4, $R_2$-4 is unsubstituted.
[5] In another embodiment, the invention is represented by Formula I in which $R_2$ is 4-(3-amino-1,2,5-oxadiazol-4-yl)phenyl or 3-(3-amino-1,2,5-oxadiazol-4-yl)phenyl($R_2$-5), optionally substituted.
[5a] In embodiment 5, $R_2$-5 is substituted.
[6] In another embodiment, the invention is represented by Formula I in which $R_2$ is one of the groups $R_2$-1-$R_2$-5, substituted by one or more alkyl, halo, amino, alkylamino, hydroxyl, or alkoxy substituents.
[6a] In embodiment 6, $R_2$ is substituted by one or more alkyl or halo substituents.
[6b] In embodiment 6, $R_2$ is substituted by one or more amino, alkylamino, hydroxyl, or alkoxy substituents.
[7] In another embodiment, the invention is represented by Formula I in which $R_2$ is one of the groups $R_2$-1-$R_2$-5, and is unsubstituted.
[8] In another embodiment, the invention is represented by Formula I in which $R_3$ is H.
[9] In another embodiment, the invention is represented by Formula I in which Q is $(CR_4R_5)_{n3}$, and $n_3$ is 1 or 2.
[10] In another embodiment, the invention is represented by Formula I in which Q is $(CH_2)_{n3}$, and $n_3$ is 1.
[11] In another embodiment, the invention is represented by Formula I in which $R_1$ is aryl or heteroaryl substituted with one or more alkenyl, alkynyl, aryl, arylalkyl, arylalkenyl, arylalkynyl, heteroaryl, heteroarylalkyl, heteroarylalkenyl, heteroarylalkynyl, cycloalkyl, cycloalkenyl, cycloalkylalkyl, cycloalkylalkenyl, cycloalkylalkynyl, heterocycle, (heterocycle)alkyl, (heterocycle)alkenyl, or (heterocycle)alkynyl substituents, optionally further substituted.
Compounds exemplifying embodiment 11 include compounds 1.009, 1.010, 1.011, 1.012, 1.020, 1.021, 1.030, 1.034, 1.037, 1.044, 1.047, 1.076, 1.077, 1.083, 2.010, 2.011, 2.019, 2.020, 2.022, 2.023, and 2.031, shown below in Table A.
[12] In another embodiment, the invention is represented by Formula I in which $R_1$ is aryl or heteroaryl substituted with one or more heteroatom-containing substituents, with the proviso that if the $R_1$ substituent is acyclic and is connected to $R_1$ by a carbon atom, then this substituent contains at least one nitrogen or sulfur atom, with the second proviso that if the substituent is acyclic and is connected to $R_1$ by an oxygen or nitrogen atom, then this substituent contains at least one additional oxygen, nitrogen or sulfur atom, and with the third proviso that if the substituent is connected to $R_1$ by a sulfone linkage "—$SO_2$—", then $R_2$ is not nitrogen- or oxygen-substituted $R_2$-2.
[12a] In embodiment 12, the heteroatom-containing substituent is connected to $R_1$ by an oxygen or nitrogen atom.
[12b] In embodiment 12, the heteroatom-containing substituent is connected to $R_1$ by a sulfide linkage, "—S—".
Compounds exemplifying embodiment 12 include compounds 1.001, 1.002, 1.004, 1.005, 1.038, 1.048, 1.055, 1.056, 2.002, 2.003, 2.005, 2.007, 1.003, 1.006, 1.007, 1.018, 1.039, 1.051, 1.058, 1.060, 1.084, 1.085, 1.086, 1.087, 1.088, 1.090, 1.091, 1.092, 1.093, 1.094, 1.095, 1.096, 1.097, 1.098, 1.102, 1.111, 1.113, 1.115, 1.116, 1.117, 1.118, 1.120, 1.121, 1.123, 1.124, 1.125, 1.126, 1.127, 1.128, 1.129, 1.130, 2.004, 2.008, 2.032, 2.033, 2.034, 2.035, 2.036, 2.037, 2.038, 2.039, 2.040, 2.041, 2.042, 2.043, 2.044, 1.008, 1.017, 1.026, 1.040, 1.074, 1.075, 2.009, 2.012, 2.021, 2.024, 2.026, and 2.029, shown below in Table A.
[13] In another embodiment, the invention is represented by Formula I in which $R_1$ is aryl or heteroaryl substituted with one or more alkyl, alkenyl, alkynyl, aryl, arylalkyl, arylalkenyl, arylalkynyl, heteroaryl, heteroarylalkyl, heteroarylalkenyl, heteroarylalkynyl, cycloalkyl, cycloalkenyl, cycloalkylalkyl, cycloalkylalkenyl, cycloalkylalkynyl, heterocycle, (heterocycle)alkyl, (heterocycle)alkenyl, or (heterocycle)alkynyl substituents, which are further substituted with one or more heteroatom-containing substituents, with the proviso that if the $R_1$ substituent is acyclic and its heteroatom-containing substituent falls on the carbon by which it is attached to $R_1$, then the heteroatom-containing substituent contains at least one nitrogen or sulfur atom.
Compounds exemplifying embodiment 13 include compounds 1.019, 1.027, 1.028, 1.029, 1.035, 1.041, 1.042, 1.043, 1.057, 1.061, 1.099, 1.101, 1.103, 1.104, 1.105, 1.106, 1.107, 1.108, 1.109, 1.112, 1.114, 1.119, 1.122, and 1.123, shown below in Table A.
[14] In another embodiment, the invention is represented by Formula I in which $R_1$ is aryl or heteroaryl substituted with one or more alkenyl, alkynyl, aryl, arylalkyl, arylalkenyl, arylalkynyl, heteroaryl, heteroarylalkyl, heteroarylalkenyl, heteroarylalkynyl, cycloalkyl, cycloalkenyl, cycloalkylalkyl, cycloalkylalkenyl, cycloalkylalkynyl, heterocycle, (heterocycle)alkyl, (heterocycle)alkenyl, or (heterocycle)alkynyl substituents, optionally further substituted, and $R_2$ is 5-indazolyl($R_2$-1) or 5-isoquinolinyl($R_2$-2), optionally substituted.
[14a] In embodiment 14, $R_2$ is 5-indazolyl($R_2$-1), optionally substituted by one or more alkyl, halo, amino, alkylamino, hydroxyl, or alkoxy substituents.
[14b] In embodiment 14, $R_2$ is 5-isoquinolinyl($R_2$-2), optionally substituted by one or more alkyl, halo, amino, alkylamino, hydroxyl, or alkoxy substituents.
[14c] In embodiment 14, $R_2$ is unsubstituted.
Compounds exemplifying embodiment 14 include compounds 1.009, 1.010, 1.011, 1.012, 1.020, 1.021, 1.030, 1.034, 1.037, 1.044, 1.047, 1.076, 1.077, 1.083, 2.010, 2.011, 2.019, 2.020, 2.022, 2.023, and 2.031, shown below in Table A.
[15] In another embodiment, the invention is represented by Formula I in which $R_1$ is aryl or heteroaryl substituted with one or more heteroatom-containing substituents, and $R_2$ is 5-indazolyl($R_2$-1) or 5-isoquinolinyl($R_2$-2), optionally substituted, with the proviso that if the $R_1$ substituent is acyclic and is connected to $R_1$ by a carbon atom, then this substituent contains at least one nitrogen or sulfur atom, with the second proviso that if the substituent is acyclic and is connected to $R_1$ by an oxygen or nitrogen atom, then this substituent contains at least one additional oxygen, nitrogen or sulfur atom, and with the third proviso that if the substituent is connected to $R_1$ by a sulfone linkage "—$SO_2$-", then $R_2$ is not nitrogen- or oxygen-substituted $R_2$-2.

[15a] In embodiment 15, $R_2$ is 5-indazolyl($R_2$-1), optionally substituted by one or more alkyl, halo, amino, alkylamino, hydroxyl, or alkoxy substituents.

[15b] In embodiment 15, $R_2$ is 5-isoquinolinyl($R_2$-2), optionally substituted by one or more alkyl, halo, amino, alkylamino, hydroxyl, or alkoxy substituents.

[15c] In embodiment 15, $R_2$ is unsubstituted.

[15d] In embodiment 15, the heteroatom-containing substituent is connected to $R_1$ by an oxygen or nitrogen atom.

[15e] In embodiment 15, the heteroatom-containing substituent is connected to $R_1$ by a sulfide linkage, "—S—".

Compounds exemplifying embodiment 15 include compounds 1.001, 1.002, 1.004, 1.005, 1.038, 1.048, 1.055, 1.056, 2.002, 2.003, 2.005, 2.007, 1.003, 1.006, 1.007, 1.018, 1.039, 1.051, 1.058, 1.060, 1.084, 1.085, 1.086, 1.087, 1.088, 1.090, 1.091, 1.092, 1.093, 1.094, 1.095, 1.096, 1.097, 1.098, 1.102, 1.111, 1.113, 1.115, 1.116, 1.117, 1.118, 1.120, 1.121, 1.123, 1.124, 1.125, 1.126, 1.127, 1.128, 1.129, 1.130, 2.004, 2.008, 2.032, 2.033, 2.034, 2.035, 2.036, 2.037, 2.038, 2.039, 2.040, 2.041, 2.042, 2.043, 2.044, 1.008, 1.017, 1.026, 1.040, 1.074, 1.075, 2.009, 2.012, 2.021, 2.024, 2.026, and 2.029, shown below in Table A.

[16] In another embodiment, the invention is represented by Formula I in which $R_1$ is aryl or heteroaryl substituted with one or more alkyl, alkenyl, alkynyl, aryl, arylalkyl, arylalkenyl, arylalkynyl, heteroaryl, heteroarylalkyl, heteroarylalkenyl, heteroarylalkynyl, cycloalkyl, cycloalkenyl, cycloalkylalkyl, cycloalkylalkenyl, cycloalkylalkynyl, heterocycle, (heterocycle)alkyl, (heterocycle)alkenyl, or (heterocycle)alkynyl substituents, at least one of which is further substituted with one or more heteroatom-containing substituents, and $R_2$ is 5-indazolyl($R_2$-1) or 5-isoquinolinyl($R_2$-2), optionally substituted, with the proviso that if the $R_1$ substituent is acyclic and its heteroatom-containing substituent falls on the carbon by which it is attached to $R_1$, then the heteroatom-containing substituent contains at least one nitrogen or sulfur atom.

[16a] In embodiment 16, $R_2$ is 5-indazolyl($R_2$-1), optionally substituted by one or more alkyl, halo, amino, alkylamino, hydroxyl, or alkoxy substituents.

[16b] In embodiment 16, $R_2$ is 5-isoquinolinyl($R_2$-2), optionally substituted by one or more alkyl, halo, amino, alkylamino, hydroxyl, or alkoxy substituents.

[16c] In embodiment 16, $R_2$ is unsubstituted.

Compounds exemplifying embodiment 16 include compounds 1.019, 1.027, 1.028, 1.029, 1.035, 1.041, 1.042, 1.043, 1.057, 1.061, 1.099, 1.101, 1.103, 1.104, 1.105, 1.106, 1.107, 1.108, 1.109, 1.112, 1.114, 1.119, 1.122, and 1.123, shown below in Table A.

The inventors have discovered certain compounds of Formula I that have properties that render them particularly useful for treating the conditions addressed by the invention. In particular, these preferred compounds can be described as compounds of Formula I in which $R_2$, $R_3$, $n_1$, and $n_2$ are limited to the combinations shown in Formulae Ia, Ib, and Ic:

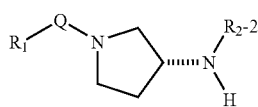

Formula Ia

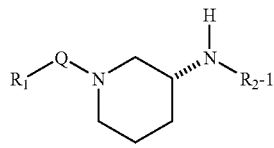

Formula Ib

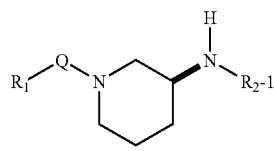

Formula Ic

In Formulae Ia, Ib, and Ic, the stereochemistry of the central pyrrolidine or piperidine ring is limited to the R, R, and S configurations respectively, as drawn. Further, the group $R_1$ in these Formulae is limited to phenyl, thiophene, and 6,5- or 6,6-fused bicyclic heteroaryl rings. The group $R_1$ is either unsubstituted or is optionally substituted with 1, 2 or 3 substituents independently selected from halogen, methyl, ethyl, hydroxyl, methoxy, or ethoxy.

In Formula Ia, Ib, and Ic, Q is C=O, $SO_2$, or $(CR_4R_5)_{n3}$; where $R_4$ and $R_5$ are independently H, alkyl, cycloalkyl, optionally substituted. The preferred $R_4$ and $R_5$ are H or unsubstituted alkyl. The preferred Q is $CH_2$.

In Formula Ia, Ib, and Ic, a preferred $R_2$ substituent is halo, alkyl, cycloalkyl, hydroxyl, alkoxy, cycloalkyloxy, amino, alkylamino, or $R_2$ is unsubstituted. A more preferred $R_2$ substituent is halo, methyl, ethyl, isopropyl, cyclopropyl, hydroxyl, methoxy, ethoxy, amino, methylamino, dimethylamino, or $R_2$ is unsubstituted.

In a more preferred form of Formulae Ia, Ib, and Ic, $R_1$ is phenyl or a 6,5-fused bicyclic heteroaryl ring, optionally substituted by 1 or 2 substituents, Q is $CH_2$, and the group $R_2$ is unsubstituted. The most preferred 6,5-fused bicyclic heteroaryl rings are benzofuran, benzothiophene, indole, and benzimidazole.

In another more preferred form, $R_1$ of Formulae Ia, Ib, and Ic is mono- or disubstituted when $R_1$ is phenyl, with 3-substituted, 4-substituted, 2,3-disubstituted, and 3,4-disubstituted being most preferred, When $R_1$ is bicyclic heteroaryl, an unsubstituted or monosubstituted $R_1$ is most preferred.

The inventors have found that certain members of Formulae Ia, Ib, and Ic, as defined above, are particularly useful in treating the conditions addressed in this invention. The compounds of the invention are multikinase inhibitors, with inhibitory activity against ROCK1 and ROCK2, in addition to several other kinases in individual compound cases. These kinase inhibitory properties endow the compounds of the invention not only with smooth muscle relaxant properties, but additionally with antiproliferative, antichemotactic, and cytokine secretion inhibitory properties that render them particularly useful in treating conditions with proliferative or inflammatory components as described in the invention.

[17] In particular, we have found that compounds in which $R_2$ is $R_2$-2 are particularly potent inhibitors of both ROCK1 and ROCK2, and that these agents inhibit the migration of neutrophils toward multiple chemotactic stimuli and inhibit the secretion of the cytokines IL-1β, TNF-α and IL-9 from LPS-stimulated human monocytes. Compounds in which $R_1$ is heteroaryl, particularly 6,5-fused bicyclic heteroaryl, are especially preferred. These compounds are of particular value in addressing conditions with an inflammatory component. Compounds exemplifying embodiment 17 include compounds 2.025, 2.027, 2.046, 2.047, 2.048, 2.055, 2.056, 2.057, 2.061, 2.062, 2.065, 2.074, 2.075, 2.088, and 2.090.

[18] In another embodiment, we have found that compounds of Formula Ic are potent and selective inhibitors of ROCK2, with comparatively lower inhibitory potency against ROCK1. We have demonstrated that compounds of this class typically show good smooth muscle relaxation properties and that smooth muscle relaxation effects in this class are generally correlated with ROCK2 potency. Compounds in which $R_1$ is phenyl are particularly preferred. Compounds of this embodiment are of particular value in addressing conditions where relaxation of smooth muscle, in particular vascular and bronchial smooth muscle, is of highest importance.

Compounds exemplifying embodiment 18 include compounds 1.072, 1.078, 1.079, 1.080, 1.141, 1.142, 1.148, 1.149, 1.150, 1.151, 1.154, 1.155, 1.156, 1.163, 1.164, 1.166, 1.170, 1.171, 1.175, 1.179, 1.183, 1.227, 1.277, and 1.278.

[19] In another embodiment, the inventors have found that compounds of Formula Ib are potent mixed inhibitors of ROCK1 and ROCK2, display additional inhibitory activity against the kinases Akt3 and p70S6K, and that these compounds generally display potent antiproliferative activity in models of smooth muscle cell proliferation. Compounds of this class are of particular value in addressing conditions in which an antiproliferative component is desired in combination with a smooth muscle relaxing effect.

Compounds exemplifying embodiment 19 include compounds 1.073, 1.110, 1.131, 1.132, 1.133, 1.134, 1.135, 1.136, 1.137, 1.138, 1.143, 1.144, 1.145, 1.146, 1.172, 1.173, 1.177, 1.191, 1.192, 1.203, 1.210, 1.226, 1.241, 1.242, 1.245, 1.246, 1.252, and 1.254.

[20] In another embodiment, the inventors have found that certain compounds of Formulae Ia, Ib, and Ic distribute preferentially to the lung on oral dosing. In particular, compounds in which $R_1$ is a lipophilic bicyclic heteroaryl group are preferred for this dosing behavior.

Compounds of this type are especially useful for treating diseases of the lung by oral dosing while minimizing impact on other tissues.

Compounds exemplifying embodiment 20 include compounds 1.131, 1.137, 1.138, 1.143, 1.148, 1.149, 1.150, 1.166, 1.175, 1.177, 1.246, 1.252, 2.055, 2.056, 2.057, 2.065, 2.074, and 2.075.

[21] In another embodiment, the inventors have found that certain compounds of Formulae Ia, Ib, and Ic produce low plasma concentrations of the compound when dosed by the oral route. Compounds in which one substituent on $R_1$ is selected from the group methyl, ethyl, or hydroxyl are preferred for typically exhibiting this pharmacokinetic behavior. Compounds displaying this property are particularly useful for inhalation dosing, since a large portion of the material dosed in this way is typically swallowed, and it is advantageous for this swallowed portion to remain unabsorbed or to be cleared rapidly so as to minimize the impact of the compound on other tissues.

Compounds exemplifying embodiment 21 include compounds 1.078, 1.133, 1.135, 1.136, 1.145, 1.151, 1.154, 1.155, 1.156, 1.163, 1.171, 1.172, 1.173, 1.192, 1.242, 2.025, and 2.061.

Preparation of compounds of Formulae Ia, Ib, and Ic can be problematic using methods commonly known in the art. In particular, syntheses of compounds of Formulae Ib and Ic using transition metal mediated coupling reactions to form the critical bond between $R_2$-1 and the nitrogen atom are hampered by low yields when the indazole ring is not protected properly to allow a successful reaction. Specifically, the methods disclosed in UA2006/0167043 fail to provide the desired amino indazole products when the indazole is unprotected or is protected with a standard acyl protecting group such as pivalate or alkoxycarbonyl protecting groups. The inventors prepare compounds of Formulae Ia, Ib, and Ic according to the methods disclosed in the co-pending application US2008/0214614, which allows the successful protection, coupling, and deprotection of the indazole ring, thereby allowing the successful preparation of the compounds of Formulae Ib and Ic and the demonstration of their useful biological properties.

B. Formula II

A preferred compound of Formula I is where $R_1$=Ar—X, shown below as Formula II:

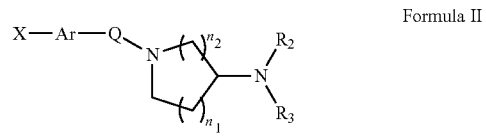

Formula II wherein:

Ar is a monocyclic or bicyclic aryl or heteroaryl ring, such as phenyl;

X is from 1 to 3 substituents on Ar, each independently in the form Y-Z, in which Z is attached to Ar;

Y is one or more substituents on Z, and each is chosen independently from H, halogen, or the heteroatom-containing substituents, including but not limited to $OR_9$, $NR_8R_9$, $NO_2$, $SR_8$, $SOR_8$, $SO_2R_8$, $SO_2NR_8R_9$, $NR_8SO_2R_9$, $OCF_3$, $CONR_8R_9$, $NR_8C(=O)R_9$, $NR_8C(=O)OR_9$, $OC(=O)NR_8R_9$, or $NR_8C(=O)NR_9R_{10}$;

Each instance of Z is chosen independently from alkyl, alkenyl, alkynyl, aryl, arylalkyl, arylalkenyl, arylalkynyl, cycloalkyl, cycloalkenyl, cycloalkylalkyl, cycloalkylalkenyl, cycloalkylalkynyl, heteroaryl, heteroarylalkyl, heteroarylalkenyl, heteroarylalkynyl, heterocycle, (heterocycle)alkyl, (heterocycle)alkenyl, (heterocycle)alkynyl, or is absent;

$R_8$ is H, alkyl, alkenyl, alkynyl, aryl, arylalkyl, arylalkenyl, arylalkynyl, cycloalkyl, cycloalkenyl, cycloalkylalkyl, cycloalkylalkenyl, cycloalkylalkynyl, heteroaryl, heteroarylalkyl, heteroarylalkenyl, heteroarylalkynyl, (heterocycle)alkyl, (heterocycle)alkenyl, (heterocycle)alkynyl, or heterocycle; optionally substituted by one or more halogen or heteroatom-containing substituents, including but not limited to $OR_{11}$, $NR_{11}R_{12}$, $NO_2$, $SR_{11}$, $SOR_{11}$, $SO_2R_{11}$, $SO_2NR_{11}R_{12}$, $NR_{11}SO_2R_{12}$, $OCF_3$, $CONR_{11}R_{12}$, $NR_{11}C(=O)R_{12}$, $NR_{11}C(=O)OR_{12}$, $OC(=O)NR_{11}R_{12}$, or $NR_{11}C(=O)NR_{12}R_{13}$;

$R_9$ and $R_{10}$ are independently H, alkyl, alkenyl, alkynyl, aryl, arylalkyl, arylalkenyl, arylalkynyl, cycloalkyl, cycloalkenyl, cycloalkylalkyl, cycloalkylalkenyl, cycloalkylalkynyl, heteroaryl, heteroarylalkyl, heteroarylalkenyl, heteroarylalkynyl, (heterocycle)alkyl, (heterocycle)alkenyl, (heterocycle)alkynyl, or heterocycle; optionally substituted by one or more halogen or heteroatom-containing substituents, including but not limited to $OR_{14}$, $NR_{14}R_{15}$, $NO_2$, $SR_{14}$, $SOR_{14}$, $SO_2R_{14}$, $SO_2NR_{14}R_{15}$, $NR_{14}SO_2R_{15}$, $OCF_3$, $CONR_{14}R_{15}$, $NR_{14}C(=O)R_{15}$, $NR_{14}C(=O)OR_{15}$, $OC(=O)NR_{14}R_{15}$ or $NR_{14}C(=O)NR_{15}R_{16}$;

any two of the groups $R_8$, $R_9$ and $R_{10}$ are optionally joined with a link selected from the group consisting of bond, —O—, —S—, —SO—, —SO$_2$—, and —NR$_{17}$— to form a ring;

$R_{11}$-$R_{17}$ are independently H, alkyl, alkenyl, alkynyl, aryl, arylalkyl, arylalkenyl, arylalkynyl, cycloalkyl, cycloalkenyl, cycloalkylalkyl, cycloalkylalkenyl, cycloalkylalkynyl, heteroaryl, heteroarylalkyl, heteroarylalkenyl, heteroarylalkynyl, (heterocycle)alkyl, (heterocycle)alkenyl, (heterocycle)alkynyl, or heterocycle.

In Formula II, the preferred Y is H, halogen, $OR_8$, $NR_8R_9$, $NO_2$, $SR_8$, $SOR_8$, $SO_2R_8$, $SO_2NR_8R_9$, $NR_8SO_2R_9$, $OCF_3$, $CONR_8R_9$, $NR_8C(=O)R_9$, $NR_8C(=O)OR_9$, $OC(=O)NR_8R_9$, or $NR_8C(=O)NR_9R_{10}$, the more preferred Y is H, halogen, $OR_8$, $SR_8$, $SOR_8$, $SO_2R_8$, $SO_2NR_8R_9$, $NR_8SO_2R_9$, $CONR_8R_9$, or $NR_8C(=O)NR_9R_{10}$ the preferred Z is alkyl, alkenyl, alkynyl, cycloalkyl, cycloalkenyl, cycloalkylalkyl, or is absent; the more preferred Z is alkyl, alkenyl, alkynyl, cycloalkyl, or is absent, the preferred Q is $(CR_4R_5)_{n3}$ the more preferred Q is $CH_2$, the preferred $n_1$ is 1 or 2, the preferred $n_2$ is 1, the preferred $n_3$ is 1 or 2, the preferred $R_3$-$R_7$ are H, the preferred $R_8$ is H, alkyl, arylalkyl, cycloalkyl, cycloalkylalkyl, or heterocycle, the preferred $R_8$ substituents are H, halogen, $OR_{11}$, $NR_{11}R_{12}$, $SR_{11}$, $SOR_{11}$, $SO_2R_{11}$, $SO_2NR_{11}R_{12}$, $NR_{11}SO_2R_{12}$, $CONR_{11}R_{12}$, $NR_{11}C(=O)R_{12}$, and the preferred $R_9$-$R_{17}$ are H or alkyl.

In Formula II, a preferred $R_2$ substituent is halo, alkyl, cycloalkyl, hydroxyl, alkoxy, cycloalkyloxy, amino, alkylamino, or $R_2$ is unsubstituted. A more preferred $R_2$ substituent is halo, methyl, ethyl, isopropyl, cyclopropyl, hydroxyl, methoxy, ethoxy, amino, methylamino, dimethylamino, or $R_2$ is unsubstituted.

[1] One embodiment of the invention is represented by Formula II in which $R_2$ is 5-indazolyl or 6-indazolyl($R_2$-1), optionally substituted.

[1a] In embodiment 1, $R_2$-1 is substituted by one or more alkyl or halo substituents.

[1b] In embodiment 1, $R_2$-1 is substituted by one or more amino, alkylamino, hydroxyl, or alkoxy substituents.

[1c] In embodiment 1, $R_2$-1 is unsubstituted.

[2] In another embodiment, the invention is represented by Formula II in which $R_2$ is 5-isoquinolinyl or 6-isoquinolinyl($R_2$-2), optionally substituted.

[2a] In embodiment 2, $R_2$-2 is substituted by one or more alkyl or halo substituents.

[2b] In embodiment 2, $R_2$-2 is substituted by one or more amino, alkylamino, hydroxyl, or alkoxy substituents.

[2c] In embodiment 2, $R_2$-2 is unsubstituted.

[3] In another embodiment, the invention is represented by Formula II in which $R_2$ is 4-pyridyl or 3-pyridyl($R_2$-3), optionally substituted.

[3a] In embodiment 3, $R_2$-3 is substituted by one or more alkyl or halo substituents,

[3b] In embodiment 3, $R_2$-3 is substituted by one or more amino, alkylamino, hydroxyl, or alkoxy substituents.

[3c] In embodiment 3, $R_2$-3 is unsubstituted.

[4] In another embodiment, the invention is represented by Formula II in which $R_2$ is 7-azaindol-4-yl or 7-azaindol-5-yl($R_2$-4), optionally substituted.

[4a] In embodiment 4, $R_2$-4 is substituted by one or more alkyl or halo substituents.

[4b] In embodiment 4, $R_2$-4 is substituted by one or more amino, alkylamino, hydroxyl, or alkoxy substituents.

[4c] In embodiment 4, $R_2$-4 is unsubstituted.

[5] In another embodiment, the invention is represented by Formula II in which $R_2$ is 4-(3-amino-1,2,5-oxadiazol-4-yl)phenyl or 3-(3-amino-1,2,5-oxadiazol-4-yl)phenyl($R_2$-5), optionally substituted.

[5a] In embodiment 5, $R_2$-5 is unsubstituted.

[6] In another embodiment, the invention is represented by Formula II in which $R_2$ is one of the groups $R_2$-1-$R_2$-5, substituted by one or more alkyl, halo, amino, alkylamino, hydroxyl, or alkoxy substituents.

[6a] In embodiment 6, $R_2$ is substituted by one or more alkyl or halo substituents.

[6b] In embodiment 6, $R_2$ is substituted by one or more amino, alkylamino, hydroxyl, or alkoxy substituents.

[7] In another embodiment, the invention is represented by Formula II in which $R_2$ is one of the groups $R_2$-1-$R_2$-5, and is unsubstituted.

[8] In another embodiment, the invention is represented by Formula II in which $R_3$ is H.

[9] In another embodiment, the invention is represented by Formula II in which Q is $(CR_4R_5)_{n3}$, and $n_3$ is 1 or 2.

[10] In another embodiment, the invention is represented by Formula II in which Q is $(CH_2)_{n3}$, and $n_3$ is 1.

[11] In another embodiment, the invention is represented by Formula II in which for at least one substituent X, Z is alkenyl, alkynyl, aryl, arylalkyl, arylalkenyl, arylalkynyl, heteroaryl, heteroarylalkyl, heteroarylalkenyl, heteroarylalkynyl, cycloalkyl, cycloalkylalkenyl, cycloalkylalkynyl, cycloalkenyl, cycloalkylalkyl, heterocycle, (heterocycle)alkyl, (heterocycle)alkenyl, or (heterocycle)alkynyl.

Compounds exemplifying embodiment 11 include compounds 1.009, 1.010, 1.011, 1.012, 1.020, 1.021, 1.030, 1.034, 1.037, 1.044, 1.047, 1.076, 1.077, 1.083, 2.010, 2.011, 2.019, 2.020, 2.022, 2.023, and 2.031, shown below in Table A.

[12] In another embodiment, the invention is represented by Formula II in which for at least one substituent X, Z is absent, and Y is a heteroatom-containing substituent, including but not limited to $OR_8$, $NR_8R_9$, $SR_8$, $SOR_8$, $SO_2R_8$, $SO_2NR_8R_9$, $NR_8SO_2R_9$, $CONR_8R_9$, $NR_8C(=O)R_9$, $NR_8C(=O)OR_9$, $OC(=O)NR_8R_9$, or $NR_8C(=O)NR_9R_{10}$, with the proviso that if the substituent Y is acyclic and is connected to Ar by a carbon atom, then this substituent contains at least one nitrogen or sulfur atom, with the second proviso that if the substituent Y is acyclic and is connected to Ar by an oxygen or nitrogen atom, then this substituent contains at least one additional oxygen, nitrogen or sulfur atom, and with the third proviso that if the substituent Y is connected to Ar by a sulfone linkage "—$SO_2$—", then $R_2$ is not nitrogen- or oxygen-substituted $R_2$-2.

[12a] In embodiment 12, the heteroatom-containing substituent is connected to $R_1$ by an oxygen or nitrogen atom.

[12b] In embodiment 12, the heteroatom-containing substituent is connected to $R_1$ by a sulfide linkage, "—S—".

Compounds exemplifying embodiment 12 include compounds 1.001, 1.002, 1.004, 1.005, 1.038, 1.048, 1.055, 1.056, 2.002, 2.003, 2.005, 2.007, 1.003, 1.006, 1.007, 1.018, 1.039, 1.051, 1.058, 1.060, 1.084, 1.085, 1.086, 1.087, 1.088, 1.090, 1.091, 1.092, 1.093, 1.094, 1.095, 1.096, 1.097, 1.098, 1.102, 1.111, 1.113, 1.115, 1.116, 1.117, 1.118, 1.120, 1.121, 1.123, 1.124, 1.125, 1.126, 1.127, 1.128, 1.129, 1.130, 2.004, 2.008, 2.032, 2.033, 2.034, 2.035, 2.036, 2.037, 2.038, 2.039, 2.040, 2.041, 2.042, 2.043, 2.044, 1.008, 1.017, 1.026, 1.040, 1.074, 1.075, 2.009, 2.012, 2.021, 2.024, 2.026, and 2.029, shown below in Table A.

[13] In another embodiment, the invention is represented by Formula II in which for at least one substituent X, Z is alkyl, alkenyl, alkynyl, aryl, arylalkyl, arylalkenyl, arylalkynyl, heteroaryl, heteroarylalkyl, heteroarylalkenyl, heteroarylalkynyl, cycloalkyl, cycloalkenyl, cycloalkylalkyl, cycloalkylalkenyl, cycloalkylalkynyl, heterocycle, (heterocycle)alkyl, (heterocycle)alkenyl, or (heterocycle)alkynyl, and Y is a heteroatom-containing substituent, including but not limited to $OR_8$, $NR_8R_9$, $NO_2$, $SR_8$, $SOR_8$, SO$_2$R$_8$, SO$_2$NR$_8$R$_9$, NR$_8$SO$_2$R$_9$, OCF$_3$, CONR$_8$R$_9$, NR$_8$C(=O)R$_9$, NR$_8$C(=O)OR$_9$, OC(=O)NR$_8$R$_9$, or NR$_8$C(=O)NR$_9$R$_{10}$, with the proviso that if Z is acyclic and Y falls on the carbon by which Z is attached to Ar, then Y contains at least one nitrogen or sulfur atom.

Compounds exemplifying embodiment 13 include compounds 1.019, 1.027, 1.028, 1.029, 1.035, 1.041, 1.042, 1.043, 1.057, 1.061, 1.099, 1.101, 1.103, 1.104, 1.105, 1.106, 1.107, 1.108, 1.109, 1.112, 1.114, 1.119, 1.122, and 1.123, shown below in Table A.

[14] In another embodiment, the invention is represented by Formula II in which for at least one substituent X, Z is alkenyl, alkynyl, aryl, arylalkyl, arylalkenyl, arylalkynyl, heteroaryl, heteroarylalkyl, heteroarylalkenyl, heteroarylalkynyl, cycloalkyl, cycloalkenyl, cycloalkylalkyl, cycloalkylalkenyl, cycloalkylalkynyl, heterocycle, (heterocycle)alkyl, (heterocycle)alkenyl, or (heterocycle)alkynyl, and R$_2$ is 5-indazolyl(R$_2$-1) or 5-isoquinolinyl (R$_2$-2), optionally substituted.

[14a] In embodiment 14, R$_2$ is 5-indazolyl(R$_2$-1), optionally substituted by one or more alkyl, halo, amino, alkylamino, hydroxyl, or alkoxy substituents.

[14b] In embodiment 14, R$_2$ is 5-isoquinolinyl(R$_2$-2), optionally substituted by one or more alkyl, halo, amino, alkylamino, hydroxyl, or alkoxy substituents.

[14c] In embodiment 14, R$_2$ is unsubstituted.

Compounds exemplifying embodiment 14 include compounds 1.009, 1.010, 1.011, 1.012, 1.020, 1.021, 1.030, 1.034, 1.037, 1.044, 1.047, 1.076, 1.077, 1.083, 2.010, 2.011, 2.019, 2.020, 2.022, 2.023, and 2.031, shown below in Table A.

[15] In another embodiment, the invention is represented by Formula II in which for at least one substituent X, Z is absent, and Y is a heteroatom-containing substituent, including but not limited to OR$_8$, NR$_8$R$_9$, SR$_8$, SOR$_8$, SO$_2$R$_8$, SO$_2$NR$_8$R$_9$, NR$_8$SO$_2$R$_9$, CONR$_8$R$_9$, NR$_8$C(=O)R$_9$, NR$_8$C(=O)OR$_9$, OC(=O)NR$_8$R$_9$, or NR$_8$C(=O)NR$_9$R$_{10}$, and R$_2$ is 5-indazolyl(R$_2$-1) or 5-isoquinolinyl (R$_2$-2), optionally substituted, with the proviso that if the substituent Y is acyclic and is connected to Ar by a carbon atom, then this substituent contains at least one nitrogen or sulfur atom, with the second proviso that if the substituent Y is acyclic and is connected to Ar by an oxygen or nitrogen atom, then this substituent contains at least one additional oxygen, nitrogen or sulfur atom, and with the third proviso that if the substituent Y is connected to Ar by a sulfone linkage "—SO$_2$—", then R$_2$ is not nitrogen- or oxygen-substituted R$_2$-2.

[15a] In embodiment 15, R$_2$ is 5-indazolyl(R$_2$-1), optionally substituted by one or more alkyl, halo, amino, alkylamino, hydroxyl, or alkoxy substituents,

[15b] In embodiment 15, R$_2$ is 5-isoquinolinyl(R$_2$-2), optionally substituted by one or more alkyl, halo, amino, alkylamino, hydroxyl, or alkoxy substituents.

[15c] In embodiment 15, R$_2$ is unsubstituted.

[15d] In embodiment 15, the heteroatom-containing substituent is connected to R$_1$ by an oxygen or nitrogen atom.

[15e] In embodiment 15, the heteroatom-containing substituent is connected to R$_1$ by a sulfide linkage, "—S—".

Compounds exemplifying embodiment 15 include compounds 1.001, 1.002, 1.004, 1.005, 1.038, 1.048, 1.055, 1.056, 2.002, 2.003, 2.005, 2.007, 1.003, 1.006, 1.007, 1.018, 1.039, 1.051, 1.058, 1.060, 1.084, 1.085, 1.086, 1.087, 1.088, 1.090, 1.091, 1.092, 1.093, 1.094, 1.095, 1.096, 1.097, 1.098, 1.102, 1.111, 1.113, 1.115, 1.116, 1.117, 1.118, 1.120, 1.121, 1.123, 1.124, 1.125, 1.126, 1.127, 1.128, 1.129, 1.130, 2.004, 2.008, 2.032, 2.033, 2.034, 2.035, 2.036, 2.037, 2.038, 2.039, 2.040, 2.041, 2.042, 2.043, 2.044, 1.008, 1.017, 1.026, 1.040, 1.074, 1.075, 2.009, 2.012, 2.021, 2.024, 2.026, and 2.029, shown below in Table A.

[16] In another embodiment, the invention is represented by Formula II in which for at least one substituent X, Z is alkyl, alkenyl, alkynyl, aryl, arylalkyl, arylalkenyl, arylalkynyl, heteroaryl, heteroarylalkyl, heteroarylalkenyl, heteroarylallynyl, cycloalkyl, cycloalkenyl, cycloalkylalkyl, cycloalkylalkenyl, cycloalkylalkynyl, heterocycle, (heterocycle)alkyl, (heterocycle)alkenyl, or (heterocycle)alkynyl, and Y is a heteroatom-containing substituent, including but not limited to OR$_8$, NR$_8$R$_9$, NO$_2$, SR$_8$, SOR$_8$, SO$_2$R$_8$, SO$_2$NR$_8$R$_9$, NR$_8$SO$_2$R$_9$, OCF$_3$, CONR$_8$R$_9$, NR$_8$C(=O)R$_9$, NR$_8$C(=O)OR$_9$, OC(=O)NR$_8$R$_9$, or NR$_8$C(=O)NR$_9$R$_{10}$, and R$_2$ is 5-indazolyl(R$_2$-1) or 5-isoquinolinyl(R$_2$-2), optionally substituted, with the proviso that if Z is acyclic and Y falls on the carbon by which Z is attached to Ar, then Y contains at least one nitrogen or sulfur atom.

[16a] In embodiment 16, R$_2$ is 5-indazolyl(R$_2$-1), optionally substituted by one or more alkyl, halo, amino, alkylamino, hydroxyl, or alkoxy substituents.

[16b] In embodiment 16, R$_2$ is 5-isoquinolinyl(R$_2$-2), optionally substituted by one or more alkyl, halo, amino, alkylamino, hydroxyl, or alkoxy substituents.

[16c] In embodiment 16, R$_2$ is unsubstituted.

[16d] In embodiment 16, Ar is heteroaryl.

Compounds exemplifying embodiment 16 include compounds 1.019, 1.027, 1.028, 1.029, 1.035, 1.041, 1.042, 1.043, 1.057, 1.061, 1.099, 1.101, 1.103, 1.104, 1.105, 1.106, 1.107, 1.108, 1.109, 1.112, 1.114, 1.119, 1.122, and 1.123, shown below in Table A.

In Embodiments 11-16 of Formula II, the preferred Q is (CP$_4$R$_5$)$_{n3}$, the more preferred Q is CH$_2$, the preferred n$_1$ is 1 or 2, the preferred n$_2$ is 1, the preferred n$_3$ is 1 or 2, and the preferred R$_3$ is H.

The inventors have discovered certain compounds of Formula II that have properties that render them particularly useful for treating the conditions addressed by the invention. In particular, these preferred compounds of Embodiments 14, 15 and 16 can be described as compounds of Formula II in which R$_2$, R$_3$, n$_1$, and n$_2$ are limited to the combinations shown in Formulae IIa, IIb, and IIc:

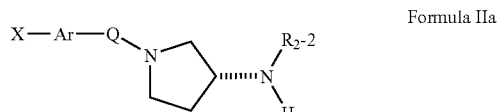

Formula IIa

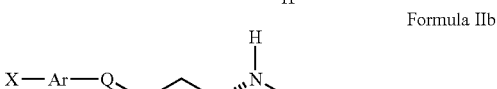

Formula IIb

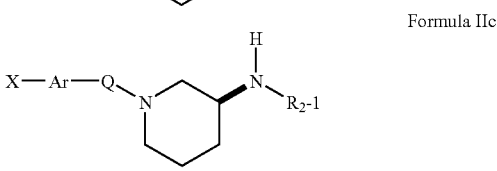

Formula IIc

In Formulae IIa, IIb, and Ic, the stereochemistry of the central pyrrolidine or piperidine ring is limited to the R, R, and S configurations respectively, as drawn.

In Formula IIa, IIb, and IIc, Q is C=O, SO$_2$, or (CR$_4$R$_5$)$_{n3}$; where R$_4$ and R$_5$ are independently H, alkyl, cycloalkyl, optionally substituted. The preferred $R_4$ and $R_5$ are H or unsubstituted alkyl. The preferred Q is $CH_2$.

In Formula IIa, IIb, and IIc, a preferred $R_2$ substituent is halo, alkyl, cycloalkyl, hydroxyl, alkoxy, cycloalkyloxy, amino, alkylamino, or $R_2$ is unsubstituted. A more preferred $R_2$ substituent is halo, methyl, ethyl, isopropyl, cyclopropyl, hydroxyl, methoxy, ethoxy, amino, methylamino, dimethylamino, or $R_2$ is unsubstituted.

In a more preferred form of Formulae IIa, IIb, and IIc, Ar is phenyl or a 6,5- or 6,6-fused bicyclic heteroaryl ring, substituted by 1 or 2 substituents X, and Q is $CH_2$. The most preferred 6,5-fused bicyclic heteroaryl rings are benzofuran, benzothiophene, indole, and benzimidazole.

In its more preferred form, Ar of Formulae IIa, IIb, and IIc is mono- or disubstituted when Ar is phenyl, with 3-substituted, 4-substituted, 2,3-disubstituted, and 3,4-disubstituted being most preferred. When Ar is bicyclic heteroaryl, a monosubstituted Ar is most preferred.

The inventors have found that certain members of Formulae IIa, IIb, and IIc, as defined above, are particularly useful in treating the conditions addressed in this invention. The compounds of the invention are multikinase inhibitors, with inhibitory activity against ROCK1 and ROCK2, in addition to several other kinases in individual compound cases. These kinase inhibitory properties endow the compounds of the invention not only with smooth muscle relaxant properties, but additionally with antiproliferative, antichemotactic, and cytokine secretion inhibitory properties that render them particularly useful in treating conditions with proliferative or inflammatory components as described in the invention.

[17] In particular, we have found that compounds in which $R_2$ is $R_2$-2 are particularly potent inhibitors of both ROCK1 and ROCK2, and that these agents inhibit the migration of neutrophils toward multiple chemotactic stimuli and inhibit the secretion of the cytokines IL-1β, TNF-α and IL-9 from LPS-stimulated human monocytes. Compounds in which Ar is heteroaryl, particularly 6,5-fused bicyclic heteroaryl, are especially preferred. These compounds are of particular value in addressing conditions with an inflammatory component.

Compounds exemplifying embodiment 17 include compounds 2.020, 2.021, 2.022, 2.026, 2.031, 2.033, 2.034, 2.038, 2.039, 2.040, 2.041, 2.043, 2.044, 2.054, 2.058, 2.059, 2.060, 2.063, 2.064, 2.066, 2.067, 2.068, 2.069, 2.070, 2.071, 2.072, 2.073, 2.076, 2.077, 2.078, 2.079, 2.080, 2.081, 2.082, 2.087, 2.092, 2.093, 2.094, 2.095, 2.096, 2.097, 2.098, 2.099, and 2.100.

[18] In another embodiment, we have found that compounds of Formula IIc are potent and selective inhibitors of ROCK2, with comparatively lower inhibitory potency against ROCK1.

We have demonstrated that compounds of this class typically show good smooth muscle relaxation properties and that smooth muscle relaxation effects in this class are generally correlated with ROCK2 potency. Compounds in which Ar is phenyl are particularly preferred, and compounds bearing one polar group X1 in the 3-position and a second group X2 in the 4-position are most preferred. Compounds of this embodiment are of particular value in addressing conditions where relaxation of smooth muscle, in particular vascular and bronchial smooth muscle, is of highest importance.

Compounds exemplifying embodiment 18 include compounds 1.075, 1.077, 1.090, 1.091, 1.094, 1.095, 1.107, 1.109, 1.117, 1.118, 1.124, 1.152, 1.153, 1.157, 1.158, 1.165, 1.168, 1.176, 1.181, 1.182, 1.184, 1.185, 1.186, 1.187, 1.195, 1.196, 1.197, 1.198, 1.199, 1.200, 1.201, 1.213, 1.214, 1.215, 1.217, 1.218, 1.219, 1.223, 1.224, 1.228, 1.229, 1.230, 1.233, 1.234, 1.236, 1.237, 1.238, 1.239, 1.240, 1.253, 1.255, 1.261, 1.269, 1.270, 1.272, 1.274, 1.275, 1.280, and 1.282.

[19] In another embodiment, the inventors have found that compounds of Formula IIb are potent mixed inhibitors of ROCK1 and ROCK2, display additional inhibitory activity against the kinases Akt3 and p70S6K, and that these compounds generally display potent antiproliferative activity in models of smooth muscle cell proliferation. Compounds of this class are of particular value in addressing conditions in which an antiproliferative component is desired in combination with a smooth muscle relaxing effect.

Compounds exemplifying embodiment 19 include compounds 1.074, 1.076, 1.092, 1.093, 1.096, 1.097, 1.106, 1.108, 1.113, 1.115, 1.116, 1.123, 1.125, 1.126, 1.127, 1.128, 1.129, 1.139, 1.140, 1.147, 1.159, 1.160, 1.161, 1.162, 1.174, 1.188, 1.189, 1.193, 1.194, 1.202, 1.205, 1.206, 1.207, 1.208, 1.211, 1.212, 1.221, 1.222, 1.225, 1.231, 1.232, 1.235, 1.244, 1.248, 1.249, 1.258, 1.259, 1.260, 1.262, 1.263, 1.264, 1.265, 1.266, 1.267, 1.268, 1.271, 1.273, 1.276, and 1.281.

[20] In another embodiment, the inventors have found that certain compounds of Formulae IIa, IIb, and IIc distribute preferentially to the lung on oral dosing. In particular, compounds in which Ar is a lipophilic bicyclic heteroaryl group are preferred for this dosing behavior.

Compounds of this type are especially useful for treating diseases of the lung by oral dosing while minimizing impact on other tissues.

Compounds exemplifying embodiment 20 include compounds 1.107, 1.109, 1.165, 1.106, 1.108, 2.058, 1.162, 1.264, 1.268, 1.271, 1.273, 1.217, 1.269, 2.059, 2.060, 2.066, and 2.072.

As discussed above for the compounds of Formulae Ia, Ib, and Ic, preparation of compounds of Formulae IIa, IIb, and IIc can be problematic using methods commonly known in the art. The inventors have disclosed and exemplified in US2008/0214614A1 methods to allow successful protection, coupling, and deprotection sequence that allows the successful preparation of the compounds of Formulae IIb and IIc and the demonstration of their useful biological properties.

The present compounds are useful for both oral and topical use, including use by the inhalation route. To be therapeutically effective in in this way, the compounds must have both adequate potency and proper pharmacokinetic properties such as good permeability across the biological surface relevant to the delivery route. In general, compounds of Formulae I and II bearing polar functionality, particularly on Ar, have preferred absorption properties and are particularly suitable for topical use. In general, compounds bearing small lipophilic functional groups have good ROCK inhibitory potency.

$R_1$ substitution in Formula I and X in Formula II are important factors for pharmacokinetic properties and ROCK inhibitory potency. Specifically, compounds bearing polar functionality, especially those specified in the embodiments 11, 12, 13, 14, 15, and 16 in Formulae I and II, above, are particularly suitable for topical use with adequate ROCK inhibiting activity. Compounds bearing small lipophilic functional groups, as specified in the embodiments 11, 12, 13, 14, 15, and 16 in Formulae I and II, above, display ROCK inhibition with adequate permeability across biological surfaces. Compounds bearing substituents of both types are particularly preferred, and when R1 (Formula I) or Ar (Formula II) is a phenyl ring, compounds with small lipophilic groups in the 4-position and polar functionality in the 3-position are most preferred.

Specific compounds illustrative of Formula I and Formula II are shown in the following Table A. The example compounds have been numbered in such a way that numbers of the form 1.nnn indicate compounds in which $R_2$ is $R_2$-1, numbers of the form 2.nnn indicate compounds in which $R_2$ is $R_2$-2, and so on in a similar fashion for the remaining compound numbers and groups $R_2$. In the following structures, hydrogens are omitted from the drawings for the sake of simplicity. Tautomers drawn represent all tautomers possible. Structures are drawn to indicate the preferred stereochemistry; where stereoisomers may be generated in these compounds, structures are taken to mean any of the possible stereoisomers alone or a mixture of stereoisomers in any ratio.

TABLE A

Exemplified Compounds.

| Compound | Structure | Select Embodiments 1-16 |
|---|---|---|
| 1.001 | N-(1-(4-(methylsulfonyl)benzyl)piperidin-3-yl)-1H-indazol-5-amine | 1c, 7, 8, 9, 10, 12, 15c |
| 1.002 | 3-((3-(1H-indazol-5-ylamino)piperidin-1-yl)methyl)benzonitrile | 1c, 7, 8, 9, 10, 12, 15c |
| 1.003 | N-(4-((3-(1H-indazol-5-ylamino)piperidin-1-yl)methyl)phenyl)acetamide | 1c, 7, 8, 9, 10, 12a, 15c, 15d |
| 1.004 | N-(1-(4-(methylsulfonyl)benzyl)pyrrolidin-3-yl)-1H-indazol-5-amine | 1c, 7, 8, 9, 10, 12, 15c |
| 1.005 | 3-((3-(1H-indazol-5-ylamino)pyrrolidin-1-yl)methyl)benzonitrile | 1c, 7, 8, 9, 10, 12, 15c |
| 1.006 | N-(4-((3-(1H-indazol-5-ylamino)pyrrolidin-1-yl)methyl)phenyl)acetamide | 1c, 7, 8, 9, 10, 12a, 15c, 15d |

TABLE A-continued

Exemplified Compounds.

| Compound | Structure | Select Embodiments 1-16 |
|---|---|---|
| 1.007 | N-(1-(4-(3-(dimethylamino)propoxy)benzyl)pyrrolidin-3-yl)-1H-indazol-5-amine | 1c, 7, 8, 9, 10, 12a, 15c, 15d |
| 1.008 | N-(1-(4-(methylthio)benzyl)piperidin-3-yl)-1H-indazol-5-amine | 1c, 7, 8, 9, 10, 12b, 15c, 15e |
| 1.009 | N-(1-(biphenyl-4-ylmethyl)piperidin-3-yl)-1H-indazol-5-amine | 1c, 7, 8, 9, 10, 11, 14c |
| 1.010 | N-(1-(1H-imidazol-1-yl)benzyl)piperidin-3-yl)-1H-indazol-5-amine | 1c, 7, 8, 9, 10, 11, 14c |
| 1.011 | N-(1-(4-(pyrrolidin-1-yl)benzyl)piperidin-3-yl)-1H-indazol-5-amine | 1c, 7, 8, 9, 10, 11, 14c |
| 1.012 | N-(1-(4-morpholinobenzyl)piperidin-3-yl)-1H-indazol-5-amine | 1c, 7, 8, 9, 10, 11, 14c |
| 1.013 | N-(1-(4-isobutylbenzyl)piperidin-3-yl)-1H-indazol-5-amine | 1c, 7, 8, 9, 10 |

TABLE A-continued

Exemplified Compounds.

| Compound | Structure | Select Embodiments 1-16 |
|---|---|---|
| 1.014 | 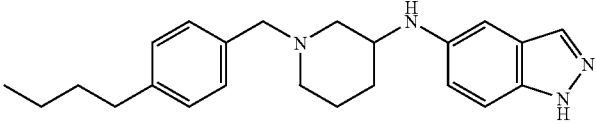<br>N-(1-(4-butylbenzyl)piperidin-3-yl)-1H-indazol-5-amine | 1c, 7, 8, 9, 10 |
| 1.015 | 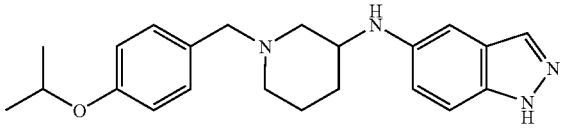<br>N-(1-(4-isopropoxybenzyl)piperidin-3-yl)-1H-indazol-5-amine | 1c, 7, 8, 9, 10 |
| 1.016 | 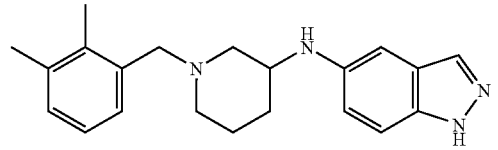<br>N-(1-(2,3-dimethylbenzyl)piperidin-3-yl)-1H-indazol-5-amine | 1c, 7, 8, 9, 10 |
| 1.017 | 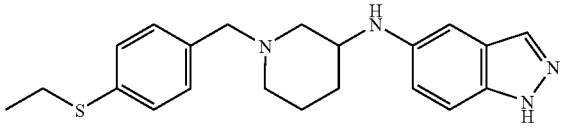<br>N-(1-(4-(ethylthio)benzyl)piperidin-3-yl)-1H-indazol-5-amine | 1c, 7, 8, 9, 10, 12b, 15c, 15e |
| 1.018 | 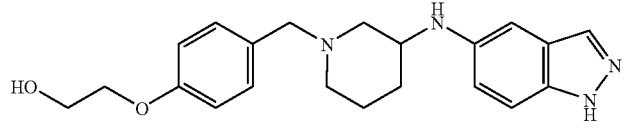<br>2-(4-((3-(1H-indazol-5-ylamino)piperidin-1-yl)methyl)phenoxy)ethanol | 1c, 7, 8, 9, 10, 12a, 15c, 15d |
| 1.019 | 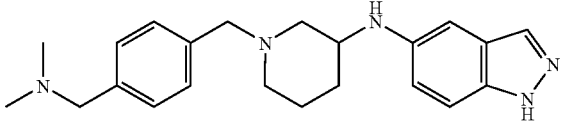<br>N-(1-(4-((dimethylamino)methyl)benzyl)piperidin-3-yl)-1H-indazol-5-amine | 1c, 7, 8, 9, 10, 13, 16c |
| 1.020 | 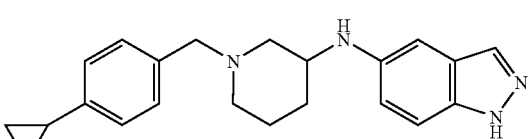<br>N-(1-(4-cyclopropylbenzyl)piperidin-3-yl)-1H-indazol-5-amine | 1c, 7, 8, 9, 10, 11, 14c |
| 1.021 | 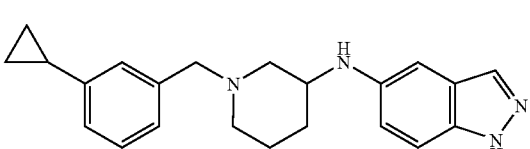<br>N-(1-(3-cyclopropylbenzyl)piperidin-3-yl)-1H-indazol-5-amine | 1c, 7, 8, 9, 10, 11, 14c |

TABLE A-continued

Exemplified Compounds.

| Compound | Structure | Select Embodiments 1-16 |
| --- | --- | --- |
| 1.022 | N-(1-(4-(trifluoromethoxy)benzyl)piperidin-3-yl)-1H-indazol-5-amine | 1c, 7, 8, 9, 10 |
| 1.023 | N-(1-(4-isopropylbenzyl)piperidin-3-yl)-1H-indazol-5-amine | 1c, 7, 8, 9, 10 |
| 1.024 | N-(1-(2,4-dimethylbenzyl)piperidin-3-yl)-1H-indazol-5-amine | 1c, 7, 8, 9, 10 |
| 1.025 | (4-((3-(1H-indazol-5-ylamino)piperidin-1-yl)methyl)phenyl)methanol | 1c, 7, 8, 9, 10 |
| 1.026 | N-(1-(4-(cyclopropylthio)benzyl)piperidin-3-yl)-1H-indazol-5-amine | 1c, 7, 8, 9, 10, 12b, 15c, 15e |
| 1.027 | tert-butyl 4-((3-(1H-indazol-5-ylamino)piperidin-1-yl)methyl)benzylcarbamate | 1c, 7, 8, 9, 10, 13, 16c |
| 1.028 | N-(1-(4-(methylthiomethyl)benzyl)piperidin-3-yl)-1H-indazol-5-amine | 1c, 7, 8, 9, 10, 13, 16c |
| 1.029 | N-(1-(4-(methylsulfonylmethyl)benzyl)piperidin-3-yl)-1H-indazol-5-amine | 1c, 7, 8, 9, 10, 13, 16c |

TABLE A-continued

Exemplified Compounds.

| Compound | Structure | Select Embodiments 1-16 |
|---|---|---|
| 1.030 | N-(1-(4-(thiophen-2-yl)benzyl)piperidin-3-yl)-1H-indazol-5-amine | 1c, 7, 8, 9, 10, 11, 14c |
| 1.031 | N-(1-benzylazepan-4-yl)-1H-indazol-5-amine | 1c, 7, 8, 9, 10 |
| 1.032 | N-(1-(4-(dimethylamino)benzyl)piperidin-3-yl)-1H-indazol-5-amine | 1c, 7, 8, 9, 10 |
| 1.033 | N-(1-(4-ethylbenzyl)piperidin-3-yl)-1H-indazol-5-amine | 1c, 7, 8, 9, 10 |
| 1.034 | N-(1-(4-ethynylbenzyl)piperidin-3-yl)-1H-indazol-5-amine | 1c, 7, 8, 9, 10, 11, 14c |
| 1.035 | N-(1-(4-(aminomethyl)benzyl)piperidin-3-yl)-1H-indazol-5-amine | 1c, 7, 8, 9, 10, 13, 16c |
| 1.036 | 1-(4-((3-(1H-indazol-5-ylamino)piperidin-1-yl)methyl)phenyl)ethanone | 1c, 7, 8, 9, 10 |

| Compound | Structure | Select Embodiments 1-16 |
|---|---|---|
| 1.037 | 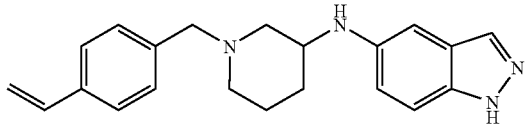<br>N-(1-(4-vinylbenzyl)piperidin-3-yl)-1H-indazol-5-amine | 1c, 7, 8, 9, 10, 11, 14c |
| 1.038 | 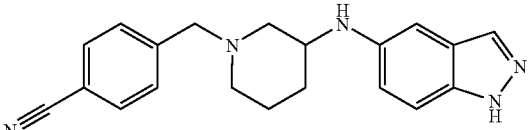<br>4-((3-(1H-indazol-5-ylamino)piperidin-1-yl)methyl)benzonitrile | 1c, 7, 8, 9, 10, 12, 15c |
| 1.039 | 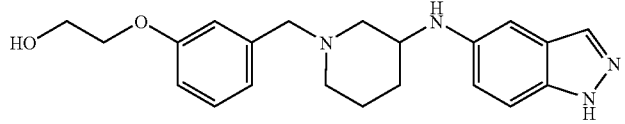<br>2-(3-((3-(1H-indazol-5-ylamino)piperidin-1-yl)methyl)phenoxy)ethanol | 1c, 7, 8, 9, 10, 12a, 15c, 15d |
| 1.040 | 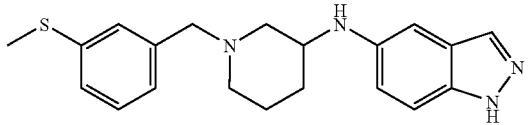<br>N-(1-(3-(methylthio)benzyl)piperidin-3-yl)-1H-indazol-5-amine | 1c, 7, 8, 9, 10, 12b, 15c, 15e |
| 1.041 | 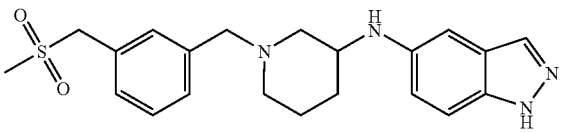<br>N-(1-(3-(methylsulfonylmethyl)benzyl)piperidin-3-yl)-1H-indazol-5-amine | 1c, 7, 8, 9, 10, 13, 16c |
| 1.042 | 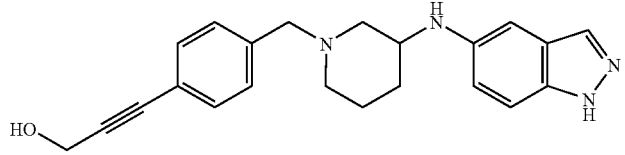<br>3-(4-((3-(1H-indazol-5-ylamino)piperidin-1-yl)methyl)phenyl)prop-2-yn-1-ol | 1c, 7, 8, 9, 10, 13, 16c |
| 1.043 | 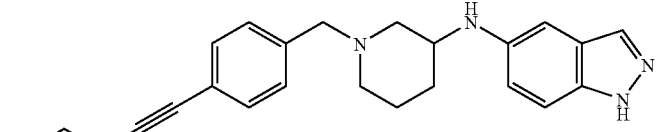<br>4-(4-((3-(1H-indazol-5-ylamino)piperidin-1-yl)methyl)phenyl)but-3-yn-1-ol | 1c, 7, 8, 9, 10, 13, 16c |

TABLE A-continued

Exemplified Compounds.

| Compound | Structure | Select Embodiments 1-16 |
|---|---|---|
| 1.044 | N-(1-(4-(cyclopropylethynyl)benzyl)piperidin-3-yl)-1H-indazol-5-amine | 1c, 7, 8, 9, 10, 11, 14c |
| 1.045 | N-(1-(3-bromobenzyl)piperidin-3-yl)-1H-indazol-5-amine | 1c, 7, 8, 9, 10 |
| 1.046 | 3-((3-(1H-indazol-5-ylamino)piperidin-1-yl)methyl)phenol | 1c, 7, 8, 9, 10 |
| 1.047 | N-(1-(3-ethynylbenzyl)piperidin-3-yl)-1H-indazol-5-amine | 1c, 7, 8, 9, 10, 11, 14c |
| 1.048 | N-(1-(3-(methylsulfonyl)benzyl)piperidin-3-yl)-1H-indazol-5-amine | 1c, 7, 8, 9, 10, 12, 15c |
| 1.049 | N-(1-benzylpiperidin-3-yl)-3-methyl-1H-indazol-5-amine | 1a, 6a, 8, 9, 10 |
| 1.050 | N5-(1-benzylpiperidin-3-yl)-1H-indazole-3,5-diamine | 1b, 6b, 8, 9, 10 |
| 1.051 | N-(3-((3-(1H-indazol-5-ylamino)piperidin-1-yl)methyl)phenyl)methanesulfonamide | 1c, 7, 8, 9, 10, 12a, 15c, 15d |

TABLE A-continued

Exemplified Compounds.

| Compound | Structure | Select Embodiments 1-16 |
| --- | --- | --- |
| 1.052 | N-(1-(benzofuran-5-ylmethyl)piperidin-3-yl)-1H-indazol-5-amine | 1c, 7, 8, 9, 10 |
| 1.053 | N-(1-((2,3-dihydrobenzo[b][1,4]dioxin-6-yl)methyl)piperidin-3-yl)-1H-indazol-5-amine | 1c, 7, 8, 9, 10 |
| 1.054 | N-(1-(benzo[b]thiophen-5-ylmethyl)piperidin-3-yl)-1H-indazol-5-amine | 1c, 7, 8, 9, 10 |
| 1.055 | 3-((3-(1H-indazol-5-ylamino)piperidin-1-yl)methyl)benzamide | 1c, 7, 8, 9, 10, 12, 15c |
| 1.056 | 3-((3-(1H-indazol-5-ylamino)piperidin-1-yl)methyl)benzenesulfonamide | 1c, 7, 8, 9, 10, 12, 15c |
| 1.057 | tert-butyl 3-((3-(1H-indazol-5-ylamino)piperidin-1-yl)methyl)benzylcarbamate | 1c, 7, 8, 9, 10, 13, 16c |
| 1.058 | 2-(5-((3-(1H-indazol-5-ylamino)piperidin-1-yl)methyl)-2-methylphenoxy)ethanol | 1c, 7, 8, 9, 10, 12a, 15c, 15d |

TABLE A-continued

Exemplified Compounds.

| Compound | Structure | Select Embodiments 1-16 |
|---|---|---|
| 1.059 | 5-((3-(1H-indazol-5-ylamino)piperidin-1-yl)methyl)-2-methylphenol | 1c, 7, 8, 9, 10 |
| 1.060 | ethyl 2-(3-((3-(1H-indazol-5-ylamino)piperidin-1-yl)methyl)phenoxy)acetate | 1c, 7, 8, 9, 10, 12a, 15c, 15d |
| 1.061 | N-(1-(3-(aminomethyl)benzyl)piperidin-3-yl)-1H-indazol-5-amine | 1c, 7, 8, 9, 10, 13, 16c |
| 1.062 | N-(1-(3,4-dichlorobenzyl)pyrrolidin-3-yl)-1H-indazol-5-amine | 1c, 7, 8, 9, 10 |
| 1.063 | N-(1-(3-(trifluoromethyl)benzyl)piperidin-3-yl)-1H-indazol-5-amine | 1c, 7, 8, 9, 10 |
| 1.064 | N-(1-(3-(trifluoromethyl)benzyl)pyrrolidin-3-yl)-1H-indazol-5-amine | 1c, 7, 8, 9, 10 |
| 1.065 | N-(1-(3-ethoxybenzyl)piperidin-3-yl)-1H-indazol-5-amine | 1c, 7, 8, 9, 10 |

TABLE A-continued

Exemplified Compounds.

| Compound | Structure | Select Embodiments 1-16 |
|---|---|---|
| 1.066 | 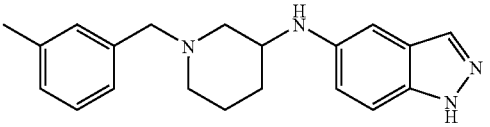<br>N-(1-(3-methylbenzyl)piperidin-3-yl)-1H-indazol-5-amine | 1c, 7, 8, 9, 10 |
| 1.067 | 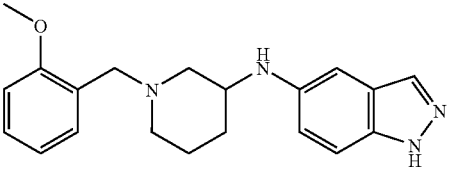<br>N-(1-(2-methoxybenzyl)piperidin-3-yl)-1H-indazol-5-amine | 1c, 7, 8, 9, 10 |
| 1.068 | 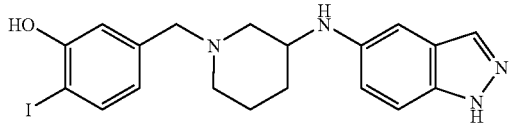<br>5-((3-(1H-indazol-5-ylamino)piperidin-1-yl)methyl)-2-iodophenol | 1c, 7, 8, 9, 10 |
| 1.069 | 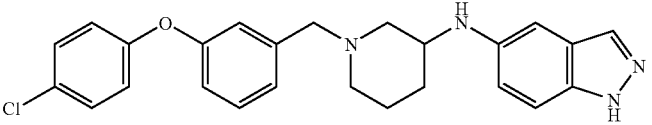<br>N-(1-(3-(4-chlorophenoxy)benzyl)piperidin-3-yl)-1H-indazol-5-amine | 1c, 7, 8, 9, 10 |
| 1.070 | 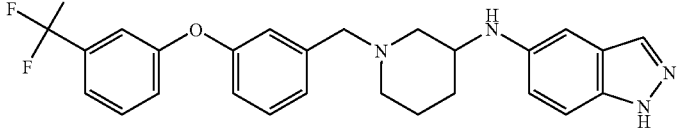<br>N-(1-(3-(3-trifluoromethyl)phenoxy)benzyl)piperidin-3-yl)-1H-indazol-5-amine | 1c, 7, 8, 9, 10 |
| 1.071 | 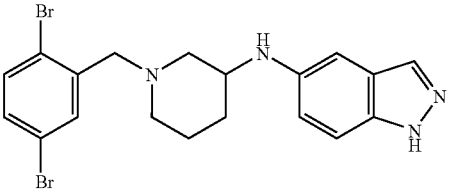<br>N-(1-(2,5-dibromobenzyl)piperidin-3-yl)-1H-indazol-5-amine | 1c, 7, 8, 9, 10 |
| 1.072 | 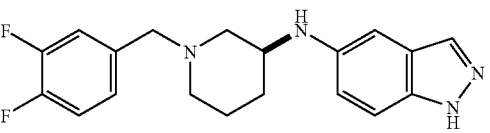<br>(S)-N-(1-(3,4-difluorobenzyl)piperidin-3-yl)-1H-indazol-5-amine | 1c, 7, 8, 9, 10 |

TABLE A-continued

Exemplified Compounds.

| Compound | Structure | Select Embodiments 1-16 |
|---|---|---|
| 1.073 | 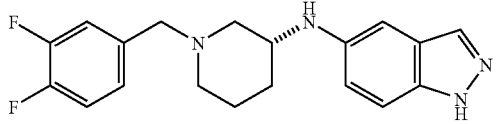<br>(R)-N-(1-(3,4-difluorobenzyl)piperidin-3-yl)-1H-indazol-5-amine | 1c, 7, 8, 9, 10 |
| 1.074 | 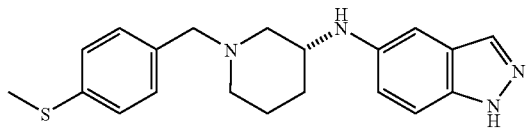<br>(R)-N-(1-(4-(methylthio)benzyl)piperidin-3-yl)-1H-indazol-5-amine | 1c, 7, 8, 9, 10, 12b, 15c, 15e |
| 1.075 | 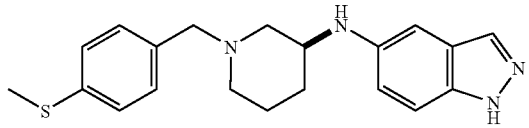<br>(S)-N-(1-(4-(methylthio)benzyl)piperidin-3-yl)-1H-indazol-5-amine | 1c, 7, 8, 9, 10, 12b, 15c, 15e |
| 1.076 | 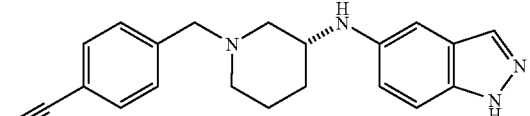<br>(R)-N-(1-4-ethynylbenzyl)piperidin-3-yl)-1H-indazol-5-amine | 1c, 7, 8, 9, 10, 11, 14c |
| 1.077 | 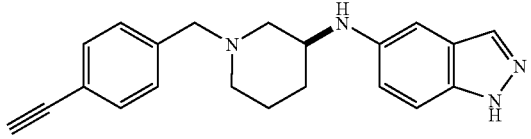<br>(S)-N-(1-(4-ethynylbenzyl)piperidin-3-yl)-1H-indazol-5-amine | 1c, 7, 8, 9, 10, 11, 14c |
| 1.078 | 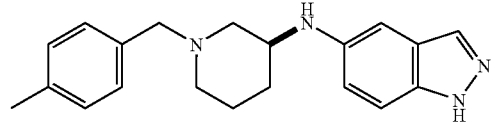<br>(S)-N-(1-(4-methylbenzyl)piperidin-3-yl)-1H-indazol-5-amine | 1c, 7, 8, 9, 10 |
| 1.079 | 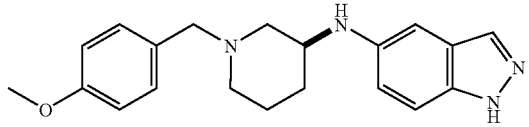<br>(S)-N-(1-(4-methoxybenzyl)piperidin-3-yl)-1H-indazol-5-amine | 1c, 7, 8, 9, 10 |
| 1.080 | 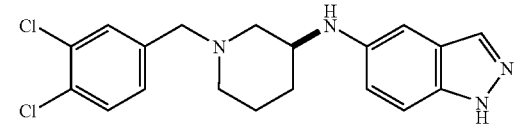<br>(S)-N-(1-(3,4-dichlorobenzyl)piperidin-3-yl)-1H-indazol-5-amine | 1c, 7, 8, 9, 10 |

TABLE A-continued

Exemplified Compounds.

| Compound | Structure | Select Embodiments 1-16 |
|---|---|---|
| 1.082 | N-(1-((1H-indol-6-yl)methyl)piperidin-3-yl)-1H-indazol-5-amine | 1c, 7, 8, 9, 10 |
| 1.083 | 5-((3-(1H-indazol-5-ylamino)piperidin-1-yl)methyl)-2-ethynylphenol | 1c, 7, 8, 9, 10, 11, 14c |
| 1.084 | 3-(3-((3-(1H-indazol-5-ylamino)piperidin-1-yl)methyl)phenoxy)propan-1-ol | 1c, 7, 8, 9, 10, 12a, 15c, 15d |
| 1.085 | N-(1-(3-(2-aminoethoxy)benzyl)piperidin-3-yl)-1H-indazol-5-amine | 1c, 7, 8, 9, 10, 12a, 15c, 15d |
| 1.086 | 2-(3-((3-(1H-indazol-5-ylamino)piperidin-1-yl)methyl)phenoxy)acetic acid | 1c, 7, 8, 9, 10, 12a, 15c, 15d |
| 1.087 | N-(3-((3-(1H-indazol-5-ylamino)pyrrolidin-1-yl)methyl)phenyl)methanesulfonamide | 1c, 7, 8, 9, 10, 12a, 15c, 15d |
| 1.088 | 2-(3-((3-(1H-indazol-5-ylamino)pyrrolidin-1-yl)methyl)phenoxy)ethanol | 1c, 7, 8, 9, 10, 12a, 15c, 15d |
| 1.089 | N-(1-(3-amino-4-chlorobenzyl)piperidin-3-yl)-1H-indazol-5-amine | 1c, 7, 8, 9, 10 |

TABLE A-continued

Exemplified Compounds.

| Compound | Structure | Select Embodiments 1-16 |
| --- | --- | --- |
| 1.090 | (S)-2-(3-((3-(1H-indazol-5-ylamino)piperidin-1-yl)methyl)phenoxy)ethanol | 1c, 7, 8, 9, 10, 12a, 15c, 15d |
| 1.091 | (S)-N-(3-((3-(1H-indazol-5-ylamino)piperidin-1-yl)methyl)phenyl)methanesulfonamide | 1c, 7, 8, 9, 10, 12a, 15c, 15d |
| 1.092 | (R)-2-(3-((3-(1H-indazol-5-ylamino)piperidin-1-yl)methyl)phenoxy)ethanol | 1c, 7, 8, 9, 10, 12a, 15c, 15d |
| 1.093 | (R)-N-(3-((3-(1H-indazol-5-ylamino)piperidin-1-yl)methyl)phenyl)methanesulfonamide | 1c, 7, 8, 9, 10, 12a, 15c, 15d |
| 1.094 | (S)-2-(3-((3-(1H-indazol-5-ylamino)pyrrolidin-1-yl)methyl)phenoxy)ethanol | 1c, 7, 8, 9, 10, 12a, 15c, 15d |
| 1.095 | (S)-N-(3-((3-(1H-indazol-5-ylamino)pyrrolidin-1-yl)methyl)phenyl)methanesulfonamide | 1c, 7, 8, 9, 10, 12a, 15c, 15d |
| 1.096 | (R)-2-(3-((3-(1H-indazol-5-ylamino)pyrrolidin-1-yl)methyl)phenoxy)ethanol | 1c, 7, 8, 9, 10, 12a, 15c, 15d |

TABLE A-continued

Exemplified Compounds.

| Compound | Structure | Select Embodiments 1-16 |
| --- | --- | --- |
| 1.097 | (R)-N-(3-((3-(1H-indazol-5-ylamino)pyrrolidin-1-yl)methyl)phenyl)methanesulfonamide | 1c, 7, 8, 9, 10, 12a, 15c, 15d |
| 1.098 | 2-(3-((3-(1H-indazol-5-ylamino)piperidin-1-yl)methyl)phenoxy)acetamide | 1c, 7, 8, 9, 10, 12a, 15c, 15d |
| 1.099 | 2-(6-((3-(1H-indazol-5-ylamino)piperidin-1-yl)methyl)-1H-indol-1-yl)acetamide | 1c, 7, 8, 9, 10, 13, 16c |
| 1.100 | N-(1-((1H-indol-5-yl)methyl)piperidin-3-yl)-1H-indazol-5-amine | 1c, 7, 8, 9, 10, 13, 16c |
| 1.101 | 2-(6-((3-(1H-indazol-5-ylamino)piperidin-1-yl)methyl)-1H-indol-1-yl)ethanol | 1c, 7, 8, 9, 10, 13, 16c |
| 1.102 | N-(5-((3-(1H-indazol-5-ylamino)piperidin-1-yl)methyl)-2-chlorophenyl)methanesulfonamide | 1c, 7, 8, 9, 10, 12a, 15c, 15d |

TABLE A-continued

Exemplified Compounds.

| Compound | Structure | Select Embodiments 1-16 |
|---|---|---|
| 1.103 | 2-(6-((3-(1H-indazol-5-ylamino)piperidin-1-yl)methyl)-1H-indol-1-yl)acetic acid | 1c, 7, 8, 9, 10, 13, 16c |
| 1.104 | 2-(6-((3-(1H-indazol-5-ylamino)piperidin-1-yl)methyl)indolin-1-yl)ethanol | 1c, 7, 8, 9, 10, 13, 16c |
| 1.105 | 2-(5-((3-(1H-indazol-5-ylamino)piperidin-1-yl)methyl)-1H-indol-1-yl)acetamide | 1c, 7, 8, 9, 10, 13, 16c |
| 1.106 | (R)-2-(6-((3-(1H-indazol-5-ylamino)piperidin-1-yl)methyl)-1H-indol-1-yl)acetamide | 1c, 7, 8, 9, 10, 13, 16c |
| 1.107 | (S)-2-(6-((3-(1H-indazol-5-ylamino)piperidin-1-yl)methyl)-1H-indol-1-yl)acetamide | 1c, 7, 8, 9, 10, 13, 16c |

TABLE A-continued

Exemplified Compounds.

| Compound | Structure | Select Embodiments 1-16 |
|---|---|---|
| 1.108 | 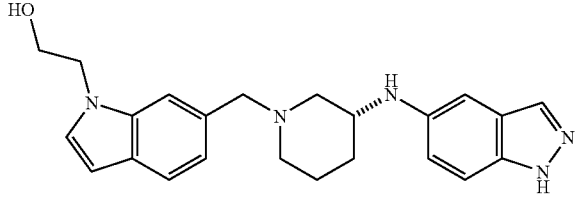<br>(R)-2-(6-((3-(1H-indazol-5-ylamino)piperidin-1-yl)methyl)-1H-indol-1-yl)ethanol | 1c, 7, 8, 9, 10, 13, 16c |
| 1.109 | 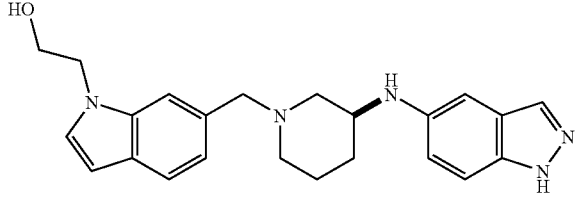<br>(S)-2-(6-((3-(1H-indazol-5-ylamino)piperidin-1-yl)methyl)-1H-indol-1-yl)ethanol | 1c, 7, 8, 9, 10, 13, 16c |
| 1.110 | 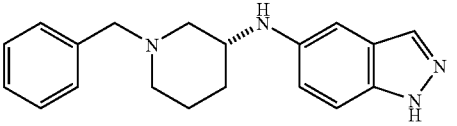<br>(R)-N-(1-benzylpiperidin-3-yl)-1H-indazol-5-amine | 1c, 7, 8, 9, 10 |
| 1.111 | 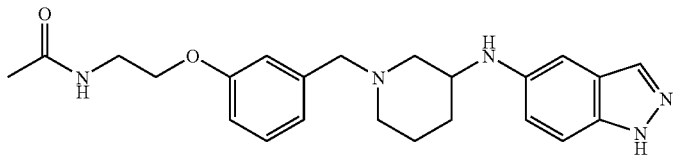<br>N-(2-(3-((3-(1H-indazol-5-ylamino)piperidin-1-yl)methyl)phenoxy)ethyl)acetamide | 1c, 7, 8, 9, 10, 12a, 15c, 15d |
| 1.112 | 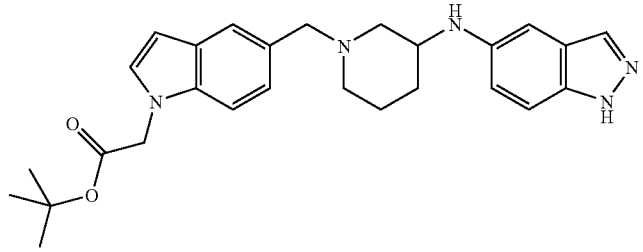<br>tert-butyl 2-(5-((3-(1H-indazol-5-ylamino)piperidin-1-yl)methyl)-1H-indol-1-yl)acetate | 1c, 7, 8, 9, 10, 13, 16c |
| 1.113 | 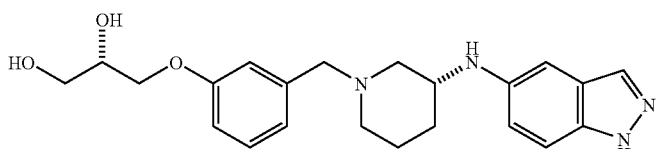<br>(S)-3-(3-(((R)-3-(1H-indazol-5-ylamino)piperidin-1-yl)methyl)phenoxy)propane-1,2-diol | 1c, 7, 8, 9, 10, 12a, 15c, 15d |

TABLE A-continued

Exemplified Compounds.

| Compound | Structure | Select Embodiments 1-16 |
|---|---|---|
| 1.114 | 2-(5-((3-(1H-indazol-5-ylamino)piperidin-1-yl)methyl)-1H-indol-1-yl)ethanol | 1c, 7, 8, 9, 10, 13, 16c |
| 1.115 | (R)-3-(3-(((R)-3-(1H-indazol-5-ylamino)piperidin-1-yl)methyl)phenoxy)propane-1,2-diol | 1c, 7, 8, 9, 10, 12a, 15c, 15d |
| 1.116 | (R)-1-(3-(((R)-3-(1H-indazol-5-ylamino)piperidin-1-yl)methyl)phenoxy)propan-2-ol | 1c, 7, 8, 9, 10, 12a, 15c, 15d |
| 1.117 | (R)-3-(3-(((S)-3-(1H-indazol-5-ylamino)piperidin-1-yl)methyl)phenoxy)propane-1,2-diol | 1c, 7, 8, 9, 10, 12a, 15c, 15d |
| 1.118 | (R)-1-(3-(((S)-3-(1H-indazol-5-ylamino)piperidin-1-yl)methyl)phenoxy)propan-2-ol | 1c, 7, 8, 9, 10, 12a, 15c, 15d |
| 1.119 | 2-(5-((3-(1H-indazol-5-ylamino)piperidin-1-yl)methyl)-1H-indol-1-yl)acetic acid | 1c, 7, 8, 9, 10, 13, 16c |

TABLE A-continued

Exemplified Compounds.

| Compound | Structure | Select Embodiments 1-16 |
|---|---|---|
| 1.120 | N-(3-((3-(1H-indazol-5-ylamino)piperidin-1-yl)methyl)phenyl)ethanesulfonamide | 1c, 7, 8, 9, 10, 12a, 15c, 15d |
| 1.121 | N-(3-((3-(1H-indazol-5-ylamino)piperidin-1-yl)methyl)phenyl)-N-methylmethanesulfonamide | 1c, 7, 8, 9, 10, 12a, 15c, 15d |
| 1.122 | N-(3-((3-(1H-indazol-5-ylamino)piperidin-1-yl)methyl)benzyl)acetamide | 1c, 7, 8, 9, 10, 13, 16c |
| 1.123 | (R)-N-(3-((3-(1H-indazol-5-ylamino)piperidin-1-yl)methyl)phenyl)ethanesulfonamide | 1c, 7, 8, 9, 10, 12a, 15c, 15d |
| 1.124 | (S)-N-(3-((3-(1H-indazol-5-ylamino)piperidin-1-yl)methyl)phenyl)ethanesulfonamide | 1c, 7, 8, 9, 10, 12a, 15c, 15d |
| 1.125 | (R)-2-(3-((3-(1H-indazol-5-ylamino)piperidin-1-yl)methyl)phenoxy)acetic acid | 1c, 7, 8, 9, 10, 12a, 15c, 15d |
| 1.126 | (R)-2-(3-((3-(1H-indazol-5-ylamino)piperidin-1-yl)methyl)phenoxy)-N-(pyridin-3-yl)acetamide | 1c, 7, 8, 9, 10, 12a, 15c, 15d |

TABLE A-continued

Exemplified Compounds.

| Compound | Structure | Select Embodiments 1-16 |
|---|---|---|
| 1.127 | (R)-2-(3-((3-(1H-indazol-5-ylamino)piperidin-1-yl)methyl)phenoxy)-1-morpholinoethanone | 1c, 7, 8, 9, 10, 12a, 15c, 15d |
| 1.128 | (R)-2-(3-((3-(1H-indazol-5-ylamino)piperidin-1-yl)methyl)phenoxy)-1-(4-methylpiperazin-1-yl)ethanone | 1c, 7, 8, 9, 10, 12a, 15c, 15d |
| 1.129 | (R)-diethyl (3-((3-(1H-indazol-5-ylamino)piperidin-1-yl)methyl)phenoxy)methylphosphonate | 1c, 7, 8, 9, 10, 12a, 15c, 15d |
| 1.130 | 2-(3-((4-(1H-indazol-5-ylamino)piperidin-1-yl)methyl)phenoxy)ethanol | 1c, 7, 8, 9, 10, 12a, 15c, 15d |
| 1.131 | (R)-N-(1-(benzofuran-5-ylmethyl)piperidin-3-yl)-1H-indazol-5-amine | 1c, 7, 8, 9, 10 |
| 1.132 | (R)-N-(1-(4-chlorobenzyl)piperidin-3-yl)-1H-indazol-5-amine | 1c, 7, 8, 9, 10 |
| 1.133 | (R)-N-(1-(4-methylbenzyl)piperidin-3-yl)-1H-indazol-5-amine | 1c, 7, 8, 9, 10 |

TABLE A-continued

Exemplified Compounds.

| Compound | Structure | Select Embodiments 1-16 |
|---|---|---|
| 1.134 | 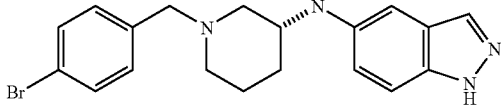<br>(R)-N-(1-(4-bromobenzyl)piperidin-3-yl)-1H-indazol-5-amine | 1c, 7, 8, 9, 10 |
| 1.136 | 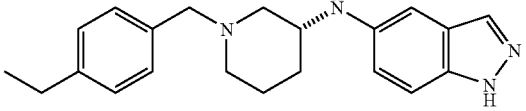<br>(R)-N-(1-(4-ethylbenzyl)piperidin-3-yl)-1H-indazol-5-amine | 1c, 7, 8, 9, 10 |
| 1.137 | 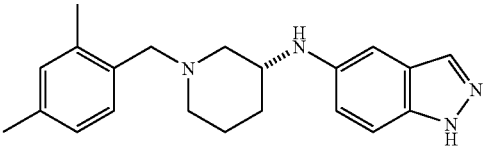<br>(R)-N-(1-(2,4-dimethylbenzyl)piperidin-3-yl)-1H-indazol-5-amine | 1c, 7, 8, 9, 10 |
| 1.138 | 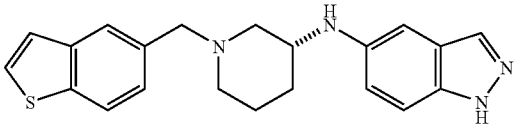<br>(R)-N-(1-(benzo[b]thiophen-5-ylmethyl)piperidin-3-yl)-1H-indazol-5-amine | 1c, 7, 8, 9, 10 |
| 1.139 | 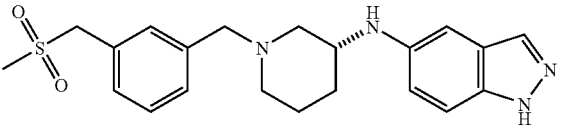<br>(R)-N-(1-(3-(methylsulfonylmethyl)benzyl)piperidin-3-yl)-1H-indazol-5-amine | 1c, 7, 8, 9, 10, 12, 15c |
| 1.140 | 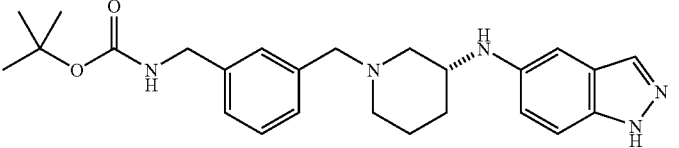<br>(R)-tert-butyl 3-((3-(1H-indazol-5-ylamino)piperidin-1-yl)methyl)benzylcarbamate | 1c, 7, 8, 9, 10, 13, 16c |
| 1.141 | 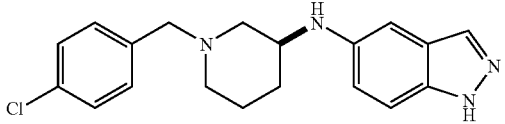<br>(S)-N-(1-(4-chlorobenzyl)piperidin-3-yl)-1H-indazol-5-amine | 1c, 7, 8, 9, 10 |
| 1.142 | 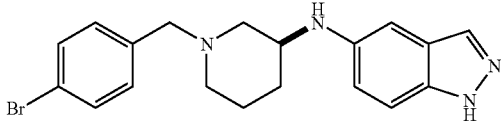<br>(S)-N-(1-(4-bromobenzyl)piperidin-3-yl)-1H-indazol-5-amine | 1c, 7, 8, 9, 10 |

TABLE A-continued

Exemplified Compounds.

| Compound | Structure | Select Embodiments 1-16 |
|---|---|---|
| 1.143 | (R)-N-(1-((1H-indol-5-yl)methyl)piperidin-3-yl)-1H-indazol-5-amine | 1c, 7, 8, 9, 10, 13, 16c |
| 1.144 | (R)-N-(1-(3,4-dichlorobenzyl)piperidin-3-yl)-1H-indazol-5-amine | 1c, 7, 8, 9, 10 |
| 1.145 | (R)-3-((3-(1H-indazol-5-ylamino)piperidin-1-yl)methyl)phenol | 1c, 7, 8, 9, 10 |
| 1.146 | (R)-N-(1-(4-fluorobenzyl)piperidin-3-yl)-1H-indazol-5-amine | 1c, 7, 8, 9, 10 |
| 1.147 | (R)-ethyl 2-(3-((3-(1H-indazol-5-ylamino)piperidin-1-yl)methyl)phenoxy)acetate | 1c, 7, 8, 9, 10, 12a, 15c, 15d |
| 1.148 | (S)-N-(1-((1H-indol-6-yl)methyl)piperidin-3-yl)-1H-indazol-5-amine | 1c, 7, 8, 9, 10 |
| 1.149 | (S)-N-(1-((1H-indol-5-yl)methyl)piperidin-3-yl)-1H-indazol-5-amine | 1c, 7, 8, 9, 10 |
| 1.150 | (S)-N-(1-(benzofuran-5-ylmethyl)piperidin-3-yl)-1H-indazol-5-amine | 1c, 7, 8, 9, 10 |

TABLE A-continued

Exemplified Compounds.

| Compound | Structure | Select Embodiments 1-16 |
|---|---|---|
| 1.151 | (S)-5-((3-(1H-indazol-5-ylamino)piperidin-1-yl)methyl)-2-methylphenol | 1c, 7, 8, 9, 10 |
| 1.152 | (S)-2-(5-((3-(1H-indazol-5-ylamino)piperidin-1-yl)methyl)-2-methylphenoxy)ethanol | 1c, 7, 8, 9, 10, 12a, 15c, 15d |
| 1.153 | (S)-N-(1-(3-ethynylbenzyl)piperidin-3-yl)-1H-indazol-5-amine | 1c, 7, 8, 9, 10, 11, 14c |
| 1.154 | (S)-N-(1-(4-ethylbenzyl)piperidin-3-yl)-1H-indazol-5-amine | 1c, 7, 8, 9, 10 |
| 1.155 | (S)-N-(1-(2,4-dimethylbenzyl)piperidin-3-yl)-1H-indazol-5-amine | 1c, 7, 8, 9, 10 |
| 1.156 | (S)-N-(1-(2,3-dimethylbenzyl)piperidin-3-yl)-1H-indazol-5-amine | 1c, 7, 8, 9, 10 |
| 1.157 | (S)-N-(1-(3-(methylsulfonylmethyl)benzyl)piperidin-3-yl)-1H-indazol-5-amine | 1c, 7, 8, 9, 10, 12, 15c |

TABLE A-continued

Exemplified Compounds.

| Compound | Structure | Select Embodiments 1-16 |
|---|---|---|
| 1.158 | (S)-N-(1-(3-(methylthio)benzyl)piperidin-3-yl)-1H-indazol-5-amine | 1c, 7, 8, 9, 10, 12b, 15c, 15e |
| 1.159 | (R)-N-(1-(3-(methylthio)benzyl)piperidin-3-yl)-1H-indazol-5-amine | 1c, 7, 8, 9, 10, 12b, 15c, 15e |
| 1.160 | (R)-N-(1-(3-(methylsulfonyl)benzyl)piperidin-3-yl)-1H-indazol-5-amine | 1c, 7, 8, 9, 10, 12, 15c |
| 1.161 | (R)-2-(5-((3-(1H-indazol-5-ylamino)piperidin-1-yl)methyl)-2-methylphenoxy)ethanol | 1c, 7, 8, 9, 10, 12a, 15c, 15d |
| 1.162 | (R)-2-(5-((3-(1H-indazol-5-ylamino)piperidin-1-yl)methyl)-1H-indol-1-yl)acetamide | 1c, 7, 8, 9, 10, 13, 16c |
| 1.163 | (S)-3-((3-(1H-indazol-5-ylamino)piperidin-1-yl)methyl)phenol | 1c, 7, 8, 9, 10 |
| 1.164 | (S)-N-(1-(4-fluorobenzyl)piperidin-3-yl)-1H-indazol-5-amine | 1c, 7, 8, 9, 10 |

TABLE A-continued

Exemplified Compounds.

| Compound | Structure | Select Embodiments 1-16 |
|---|---|---|
| 1.165 | (S)-2-(5-((3-(1H-indazol-5-ylamino)piperidin-1-yl)methyl)-1H-indol-1-yl)acetamide | 1c, 7, 8, 9, 10, 13, 16c |
| 1.166 | (S)-N-(1-((2,3-dihydrobenzo[b][1,4]dioxin-6-yl)methyl)piperidin-3-yl)-1H-indazol-5-amine | 1c, 7, 8, 9, 10 |
| 1.167 | (S)-N-A(1-(4-(trifluoromethyl)benzyl)piperidin-3-yl)-1H-indazol-5-amine | 1c, 7, 8, 9, 10 |
| 1.168 | (S)-N-(1-(4-(ethylthio)benzyl)piperidin-3-yl)-1H-indazol-5-amine | 1c, 7, 8, 9, 10, 12b, 15c, 15e |
| 1.169 | (S)-N-(1-(3-(trifluoromethyl)benzyl)piperidin-3-yl)-1H-indazol-5-amine | 1c, 7, 8, 9, 10 |
| 1.170 | (S)-N-(1-(3-chlorobenzyl)piperidin-3-yl)-1H-indazol-5-amine | 1c, 7, 8, 9, 10 |
| 1.171 | (S)-N-(1-(3-methylbenzyl)piperidin-3-yl)-1H-indazol-5-amine | 1.171 |

TABLE A-continued

Exemplified Compounds.

| Compound | Structure | Select Embodiments 1-16 |
|---|---|---|
| 1.172 | (R)-N-(1-(2,3-dimethylbenzyl)piperidin-3-yl)-1H-indazol-5-amine | 1.172 |
| 1.173 | (R)-5-((3-(1H-indazol-5-ylamino)piperidin-1-yl)methyl)-2-methylphenol | 1.173 |
| 1.174 | (R)-2-(3-((3-(1H-indazol-5-ylamino)piperidin-1-yl)methyl)phenoxy)acetamide | 1.174 |
| 1.175 | (S)-N-(1-(benzo[b]thiophen-5-ylmethyl)piperidin-3-yl)-1H-indazol-5-amine | 1.175 |
| 1.176 | (S)-tert-butyl 3-((3-(1H-indazol-5-ylamino)piperidin-1-yl)methyl)benzylcarbamate | 1.176 |
| 1.177 | (R)-N-(1-((2,3-dihydrobenzo[b][1,4]dioxin-6-yl)methyl)piperidin-3-yl)-1H-indazol-5-amine | 1.177 |
| 1.178 | (R)-N-(1-(4-(trifluoromethyl)benzyl)piperidin-3-yl)-1H-indazol-5-amine | 1.178 |

TABLE A-continued

Exemplified Compounds.

| Compound | Structure | Select Embodiments 1-16 |
|---|---|---|
| 1.179 | (S)-N-(1-(3-ethoxybenzyl)piperidin-3-yl)-1H-indazol-5-amine | 1.179 |
| 1.180 | (S)-N-(1-(4-isopropylbenzyl)piperidin-3-yl)-1H-indazol-5-amine | 1.180 |
| 1.181 | (S)-N-(1-(4-(methylsulfonyl)benzyl)piperidin-3-yl)-1H-indazol-5-amine | 1.181 |
| 1.182 | (S)-N-(1-(3-(methylsulfonyl)benzyl)piperidin-3-yl)-1H-indazol-5-amine | 1.182 |
| 1.183 | (S)-N-(1-(3-bromobenzyl)piperidin-3-yl)-1H-indazol-5-amine | 1.183 |
| 1.184 | (S)-N-(1-(3-(aminomethyl)benzyl)piperidin-3-yl)-1H-indazol-5-amine | 1.184 |
| 1.185 | (S)-N-(1-(4-(cyclopropylbenzyl)piperidin-3-yl)-1H-indazol-5-amine | 1.185 |

TABLE A-continued

Exemplified Compounds.

| Compound | Structure | Select Embodiments 1-16 |
|---|---|---|
| 1.186 | (S)-N-(1-(3-cyclopropylbenzyl)piperidin-3-yl)-1H-indazol-5-amine | 1.186 |
| 1.187 | (S)-tert-butyl 2-(3-((3-(1H-indazol-5-ylamino)piperidin-1-yl)methyl)phenoxy)acetate | 1.187 |
| 1.188 | (R)-N-(1-(4-(aminomethyl)benzyl)piperidin-3-yl)-1H-indazol-5-amine | 1.188 |
| 1.189 | (R)-N-(1-(4-(ethylthio)benzyl)piperidin-3-yl)-1H-indazol-5-amine | 1.189 |
| 1.190 | (R)-N-(1-(3-(trifluoromethyl)benzyl)piperidin-3-yl)-1H-indazol-5-amine | 1.190 |
| 1.191 | (R)-N-(1-(3-chlorobenzyl)piperidin-3-yl)-1H-indazol-5-amine | 1c, 7, 8, 9, 10 |
| 1.192 | (R)-N-(1-(3-methylbenzyl)piperidin-3-yl)-1H-indazol-5-amine | 1c, 7, 8, 9, 10 |
| 1.193 | (R)-N-(1-(3-ethynylbenzyl)piperidin-3-yl)-1H-indazol-5-amine | 1c, 7, 8, 9, 10, 11, 14c |

TABLE A-continued

Exemplified Compounds.

| Compound | Structure | Select Embodiments 1-16 |
|---|---|---|
| 1.194 | (R)-N-(1H-indazol-5-ylamino)piperidin-1-yl)methyl)benzyl)acetamide | 1c, 7, 8, 9, 10, 13, 16c |
| 1.195 | (S)-2-(3-((3-(1H-indazol-5-ylamino)piperidin-1-yl)methyl)phenyl-1H-indazol-5-ylamino)piperidin-1-yl)methyl)phenoxy)acetamide | 1c, 7, 8, 9, 10, 12a, 15c, 15d |
| 1.196 | (S)-2-(3-((3-(1H-indazol-5-ylamino)piperidin-1-yl)methyl)phenoxy)acetic acid | 1c, 7, 8, 9, 10, 12a, 15c, 15d |
| 1.197 | (S)-N-(1H-indazol-5-ylamino)piperidin-1-yl)methyl)benzyl)acetamide | 1c, 7, 8, 9, 10, 13, 16c |
| 1.198 | (S)-N-(3-((3-(1H-indazol-5-ylamino)piperidin-1-yl)methyl)phenyl)-N-methylmethanesulfonamide | 1c, 7, 8, 9, 10, 12a, 15c, 15d |
| 1.199 | (S)-tert-butyl 4-((3-(1H-indazol-5-ylamino)piperidin-1-yl)methyl)benzylcarbamate | 1c, 7, 8, 9, 10, 13, 16c |
| 1.200 | (S)-ethyl 2-(3-((3-(1H-indazol-5-ylamino)piperidin-1-yl)methyl)phenoxy)acetate | 1c, 7, 8, 9, 10, 12a, 15c, 15d |

TABLE A-continued

Exemplified Compounds.

| Compound | Structure | Select Embodiments 1-16 |
| --- | --- | --- |
| 1.201 | (S)-N-(1-(4-(aminomethyl)benzyl)piperidin-3-yl)-1H-indazol-5-amine | 1c, 7, 8, 9, 10, 13, 16c |
| 1.202 | (R)-N-(1-(3-(cyclopropylbenzyl)piperidin-3-yl)-1H-indazol-5-amine | 1c, 7, 8, 9, 10, 11, 14c |
| 1.203 | (R)-N-(1-(3-ethoxybenzyl)piperidin-3-yl)-1H-indazol-5-amine | 1c, 7, 8, 9, 10 |
| 1.204 | (R)-N-(1-(4-isopropylbenzyl)piperidin-3-yl)-1H-indazol-5-amine | 1c, 7, 8, 9, 10 |
| 1.205 | (R)-N-(1-(4-(methylsulfonyl)benzyl)piperidin-3-yl)-1H-indazol-5-amine | 1c, 7, 8, 9, 10, 12, 15c |
| 1.206 | (R)-N-(1-(4-cyclopropylbenzyl)piperidin-3-yl)-1H-indazol-5-amine | 1c, 7, 8, 9, 10, 11, 14c |
| 1.207 | (R)-N-(3-((3-(1H-indazol-5-ylamino)piperidin-1-yl)methyl)phenyl)-N-methylmethanesulfonamide | 1c, 7, 8, 9, 10, 12a, 15c, 15d |

TABLE A-continued

Exemplified Compounds.

| Compound | Structure | Select Embodiments 1-16 |
|---|---|---|
| 1.208 | (R)-N-(1-(4-vinylbenzyl)piperidin-3-yl)-1H-indazol-5-amine | 1c, 7, 8, 9, 10, 11, 14c |
| 1.209 | (R)-ethyl 4-((3-(1H-indazol-5-ylamino)piperidin-1-yl)methyl)benzoate | 1c, 7, 8, 9, 10 |
| 1.210 | (R)-N-(1-(3-bromobenzyl)piperidin-3-yl)-1H-indazol-5-amine | 1c, 7, 8, 9, 10 |
| 1.211 | (R)-N-(2-(3-((3-(1H-indazol-5-ylamino)piperidin-1-yl)methyl)phenoxy)ethyl)acetamide | 1c, 7, 8, 9, 10, 12a, 15c, 15d |
| 1.212 | (R)-N-(5-((3-(1H-indazol-5-ylamino)piperidin-1-yl)methyl)-2-chlorophenyl)methanesulfonamide | 1c, 7, 8, 9, 10, 12a, 15c, 15d |
| 1.213 | (S)-N-(5-((3-(1H-indazol-5-ylamino)piperidin-1-yl)methyl)-2-chlorophenyl)methanesulfonamide | 1c, 7, 8, 9, 10, 12a, 15c, 15d |
| 1.214 | N-((S)-1-(3-(((S)-2,2-dimethyl-1,3-dioxolan-4-yl)methoxy)benzyl)piperidin-3-yl)-1H-indazol-5-amine | 1c, 7, 8, 9, 10, 12a, 15c, 15d |

US 8,410,147 B2

TABLE A-continued

Exemplified Compounds.

| Compound | Structure | Select Embodiments 1-16 |
|---|---|---|
| 1.215 | 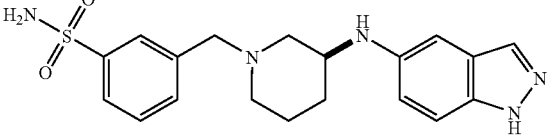<br>(S)-3-((3-(1H-indazol-5-ylamino)piperidin-1-yl)methyl)benzenesulfonamide | 1c, 7, 8, 9, 10, 12, 15c |
| 1.216 | 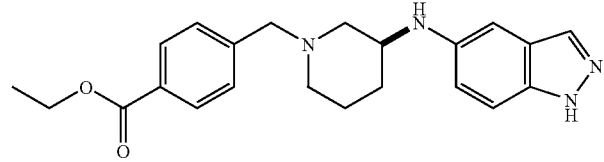<br>(S)-ethyl 4-((3-(1H-indazol-5-ylamino)piperidin-1-yl)methyl)benzoate | 1c, 7, 8, 9, 10 |
| 1.217 | 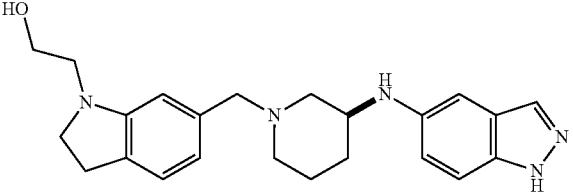<br>(S)-2-(6-((3-(1H-indazol-5-ylamino)piperidin-1-yl)methyl)indolin-1-yl)ethanol | 1c, 7, 8, 9, 10, 13, 16c |
| 1.218 | 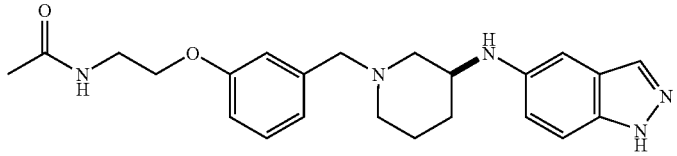<br>(S)-N-(2-(3-((3-(1H-indazol-5-ylamino)piperidin-1-yl)methyl)phenoxy)ethyl)acetamide | 1c, 7, 8, 9, 10, 12a, 15c, 15d |
| 1.219 | 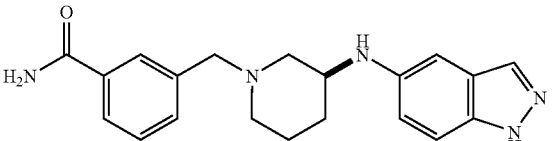<br>(S)-3-((3-(1H-indazol-5-ylamino)piperidin-1-yl)methyl)benzamide | 1c, 7, 8, 9, 10, 12, 15c |
| 1.221 | 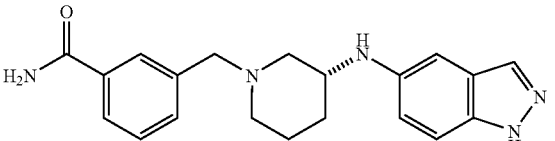<br>(R)-3-((3-(1H-indazol-5-ylamino)piperidin-1-yl)methyl)benzamide | 1c, 7, 8, 9, 10, 12, 15c |

TABLE A-continued

Exemplified Compounds.

| Compound | Structure | Select Embodiments 1-16 |
| --- | --- | --- |
| 1.222 | N-((R)-1-(3-(((S)-2,2-dimethyl-1,3-dioxolan-4-yl)methoxy)benzyl)piperidin-3-yl)-1H-indazol-5-amine | 1c, 7, 8, 9, 10, 12a, 15c, 15d |
| 1.223 | (S)-(4-((3-(1H-indazol-5-ylamino)piperidin-1-yl)methyl)phenyl)methanol | 1c, 7, 8, 9, 10, 13, 16c |
| 1.224 | (S)-2-(3-((3-(1H-indazol-5-ylamino)piperidin-1-yl)methyl)phenoxy)ethyl benzoate | 1c, 7, 8, 9, 10, 12a, 15c, 15d |
| 1.225 | (R)-2-(3-((3-(1H-indazol-5-ylamino)piperidin-1-yl)methyl)phenoxy)ethyl benzoate | 1c, 7, 8, 9, 10, 12a, 15c, 15d |
| 1.226 | (R)-N-(1-(4-methoxybenzyl)piperidin-3-yl)-1H-indazol-5-amine | 1c, 7, 8, 9, 10 |
| 1.227 | (S)-N-(1-benzylpiperidin-3-yl)-1H-indazol-5-amine | 1c, 7, 8, 9, 10 |
| 1.228 | (S)-2-(4-((3-(1H-indazol-5-ylamino)piperidin-1-yl)methyl)phenoxy)ethanol | 1c, 7, 8, 9, 10, 12a, 15c, 15d |

TABLE A-continued

Exemplified Compounds.

| Compound | Structure | Select Embodiments 1-16 |
|---|---|---|
| 1.229 | (S)-N-(1-(4-vinylbenzyl)piperidin-3-yl)-1H-indazol-5-amine | 1c, 7, 8, 9, 10, 11, 14c |
| 1.230 | (S)-3-(3-((3-(1H-indazol-5-ylamino)piperidin-1-yl)methyl)phenoxy)propan-1-ol | 1c, 7, 8, 9, 10, 12a, 15c, 15d |
| 1.231 | (R)-3-(3-((3-(1H-indazol-5-ylamino)piperidin-1-yl)methyl)phenoxy)propan-1-ol | 1c, 7, 8, 9, 10, 12a, 15c, 15d |
| 1.232 | (R)-(4-((3-(1H-indazol-5-ylamino)piperidin-1-yl)methyl)phenyl)methanol | 1c, 7, 8, 9, 10 |
| 1.233 | (S)-N-(5-((3-(1H-indazol-5-ylamino)piperidin-1-yl)methyl)-2-methylphenyl)methanesulfonamide | 1c, 7, 8, 9, 10, 12a, 15c, 15d |
| 1.234 | (S)-N-(5-((3-(1H-indazol-5-ylamino)piperidin-1-yl)methyl)-2-methoxyphenyl)methanesulfonamide | 1c, 7, 8, 9, 10, 12a, 15c, 15d |
| 1.235 | (R)-N-(1-(3-(aminomethyl)benzyl)piperidin-3-yl)-1H-indazol-5-amine | 1c, 7, 8, 9, 10, 13, 16c |
| 1.236 | (S)-N-(5-((3-(1H-indazol-5-ylamino)piperidin-1-yl)methyl)-2-methylphenyl)butane-1-sulfonamide | 1c, 7, 8, 9, 10, 12a, 15c, 15d |

TABLE A-continued

Exemplified Compounds.

| Compound | Structure | Select Embodiments 1-16 |
|---|---|---|
| 1.237 | (S)-N-(2-((3-(1H-indazol-5-ylamino)piperidin-1-yl)methyl)-5-methylphenyl)-N',N' dimethylaminosulfamide | 1c, 7, 8, 9, 10, 12a, 15c, 15d |
| 1.238 | (S)-N-(5-((3-(1H-indazol-5-ylamino)piperidin-1-yl)methyl)-2-methylphenyl)propane-1-sulfonamide | 1c, 7, 8, 9, 10, 12a, 15c, 15d |
| 1.239 | (S)-N-(5-((3-1H-indazol-5-ylamino)piperidin-1-yl)methyl)-2-methylphenyl)-4-methylbenzenesulfonamide | 1c, 7, 8, 9, 10, 12a, 15c, 15d |
| 1.240 | (S)-2-(5-((3-(1H-indazol-5-ylamino)piperidin-1-yl)methyl)-2-methylphenyl-1H-indazol-5-ylamino)piperidin-1-yl)methyl)-2-methylphenoxy)acetic acid | 1c, 7, 8, 9, 10, 12a, 15c, 15d |
| 1.241 | (R)-N-(1-(4-chlorobenzyl)pyrrolidin-3-yl)-1H-indazol-5-amine | 1c, 7, 8, 9, 10 |
| 1.242 | (R)-N-(1-(4-methylbenzyl)pyrrolidin-3-yl)-1H-indazol-5-amine | 1c, 7, 8, 9, 10 |
| 1.243 | (R)-N-(1-(3-(trifluoromethyl)benzyl)pyrrolidin-3-yl)-1H-indazol-5-amine | 1c, 7, 8, 9, 10 |

TABLE A-continued

Exemplified Compounds.

| Compound | Structure | Select Embodiments 1-16 |
|---|---|---|
| 1.244 | (R)-N-(1-(4-methylsulfonyl)benzyl)pyrrolidin-3-yl)-1H-indazol-5-amine | 1c, 7, 8, 9, 10, 12b, 15c, 15e |
| 1.245 | (R)-N-(1-(4-methoxybenzyl)pyrrolidin-3-yl)-1H-indazol-5-amine | 1c, 7, 8, 9, 10 |
| 1.246 | (R)-N-(1-((2,3-dihydrobenzofuran-5-yl)methyl)piperidin-3-yl)-1H-indazol-5-amine | 1c, 7, 8, 9, 10 |
| 1.247 | (R)-N-(1-(pyridin-4-ylmethyl)piperidin-3-yl)-1H-indazol-5-amine | 1c, 7, 8, 9, 10 |
| 1.248 | (R)-N-(1-(4-(pyrrolidin-1-yl)benzyl)piperidin-3-yl)-1H-indazol-5-amine | 1c, 7, 8, 9, 10, 11, 14c |
| 1.249 | (R)-3-((3-(1H-indazol-5-ylamino)piperidin-1-yl)methyl)benzenesulfonamide | 1c, 7, 8, 9, 10, 12b, 15c, 15e |
| 1.250 | (R)-N-(1-(3-(furan-2-yl)benzyl)piperidin-3-yl)-1H-indazol-5-amine | 1c, 7, 8, 9, 10, 11, 14c |

TABLE A-continued

Exemplified Compounds.

| Compound | Structure | Select Embodiments 1-16 |
|---|---|---|
| 1.251 | N-((3R)-1-(2-phenylpropyl)piperidin-3-yl)-1H-indazol-5-amine | 1c, 7, 8, 9 |
| 1.252 | (R)-N-(1-((1H-indol-3-yl)methyl)piperidin-3-yl)-1H-indazol-5-amine | 1c, 7, 8, 9, 10 |
| 1.253 | (S)-N-(5-((3-(1H-indazol-5-ylamino)piperidin-1-yl)methyl)-2-methylphenyl)ethanesulfonamide | 1c, 7, 8, 9, 10, 12a, 15c, 15d |
| 1.254 | (R)-N-(1-(3,4-dichlorobenzyl)pyrrolidin-3-yl)-1H-indazol-5-amine | 1c, 7, 8, 9, 10 |
| 1.255 | (S)-N-(1-(1H-imidazol-1-yl)benzyl)piperidin-3-yl)-1H-indazol-5-amine | 1c, 7, 8, 9, 10, 11, 14c |
| 1.256 | (S)-N-(1-((1H-imidazol-2-yl)methyl)piperidin-3-yl)-1H-indazol-5-amine | 1c, 7, 8, 9, 10 |
| 1.257 | (S)-N-(1-((1-methyl-1H-imidazol-2-yl)methyl)piperidin-3-yl)-1H-indazol-5-amine | 1c, 7, 8, 9, 10 |

TABLE A-continued

Exemplified Compounds.

| Compound | Structure | Select Embodiments 1-16 |
|---|---|---|
| 1.258 | (R)-N-(5-((3-(1H-indazol-5-ylamino)piperidin-1-yl)methyl)-2-methylphenyl)methanesulfonamide | 1c, 7, 8, 9, 10, 12a, 15c, 15d |
| 1.259 | (R)-N-(5-((3-(1H-indazol-5-ylamino)piperidin-1-yl)methyl)-2-methylphenyl)ethanesulfonamide | 1c, 7, 8, 9, 10, 12a, 15c, 15d |
| 1.260 | (R)-N-(5-((3-(1H-indazol-5-ylamino)piperidin-1-yl)methyl)-2-methylphenyl)-4-methylbenzenesulfonamide | 1c, 7, 8, 9, 10, 12a, 15c, 15d |
| 1.261 | (S)-N-(3-((3-(1H-indazol-5-ylamino)piperidin-1-yl)methyl)phenyl)-N′,N′ dimethylaminosulfamide | 1c, 7, 8, 9, 10, 12a, 15c, 15d |
| 1.262 | (R)-N-(2-((3-(1H-indazol-5-ylamino)piperidin-1-yl)methyl)-5-methylphenyl)-N′,N′ dimethylaminosulfamide | 1c, 7, 8, 9, 10, 12a, 15c, 15d |
| 1.263 | (R)-N-(1-((1-benzyl-1H-imidazol-2-yl)methyl)piperidin-3-yl)-1H-indazol-5-amine | 1c, 7, 8, 9, 10, 11, 14c |
| 1.264 | (7-(((R)-3-(1H-indazol-5-ylamino)piperidin-1-yl)methyl)-2,3-dihydrobenzo[b][1,4]dioxin-2-yl)methanol | 1c, 7, 8, 9, 10, 13, 16c |

TABLE A-continued

Exemplified Compounds.

| Compound | Structure | Select Embodiments 1-16 |
|---|---|---|
| 1.265 | (R)-1-(3-((3-(1H-indazol-5-ylamino)piperidin-1-yl)methyl)phenyl)-3-methylurea | 1c, 7, 8, 9, 10, 12a, 15c, 15d |
| 1.266 | (R)-N-(3-((3-(1H-indazol-5-ylamino)piperidin-1-yl)methyl)phenyl)pyrrolidine-1-carboxamide | 1c, 7, 8, 9, 10, 12a, 15c, 15d |
| 1.267 | (R)-3-(3-((3-(1H-indazol-5-ylamino)piperidin-1-yl)methyl)phenyl)-1,1-diethylurea | 1c, 7, 8, 9, 10, 12a, 15c, 15d |
| 1.268 | (R)-2-(5-((3-(1H-indazol-5-ylamino)piperidin-1-yl)methyl)-1H-indol-1-yl)ethanol | 1c, 7, 8, 9, 10, 13, 16c |
| 1.269 | (S)-2-(5-((3-(1H-indazol-5-ylamino)piperidin-1-yl)methyl)-1H-indol-1-yl)ethanol | 1c, 7, 8, 9, 10, 13, 16c |
| 1.270 | (S)-N-(3-((3-(1H-indazol-5-ylamino)piperidin-1-yl)methyl)phenyl)piperidine-1-sulfonamide | 1c, 7, 8, 9, 10, 12a, 15c, 15d |

TABLE A-continued

Exemplified Compounds.

| Compound | Structure | Select Embodiments 1-16 |
|---|---|---|
| 1.271 | (R)-N-(1-((1-benzyl-1H-indol-3-yl)methyl)piperidin-3-yl)-1H-indazol-5-amine | 1c, 7, 8, 9, 10, 11, 14c |
| 1.272 | (S)-N-(1-((1-(methylsulfonyl)-1,2,3,4-tetrahydroquinolin-6-yl)methyl)piperidin-3-yl)-1H-indazol-5-amine | 1c, 7, 8, 9, 10, 12b, 15c, 15e |
| 1.273 | (R)-2-(3-((3-(1H-indazol-5-ylamino)piperidin-1-yl)methyl)-1H-indol-1-yl)ethanol | 1c, 7, 8, 9, 10, 13, 16c |
| 1.274 | (S)-N-(3-((3-(1H-indazol-5-ylamino)piperidin-1-yl)methyl)-2-methylphenyl)methanesulfonamide | 1c, 7, 8, 9, 10, 12a, 15c, 15d |
| 1.275 | (S)-N-(3-((3-(1H-indazol-5-ylamino)piperidin-1-yl)methyl)-2-methylphenyl)-N',N'-dimethylaminosulfamide | 1c, 7, 8, 9, 10, 12a, 15c, 15d |
| 1.276 | (R)-2-(5-((3-(1H-indazol-5-ylamino)pyrrolidin-1-yl)methyl)-2-methylphenyl-1H-indazol-5-ylamino)pyrrolidin-1-yl)methyl)-2-methylphenoxy)ethanol | 1c, 7, 8, 9, 10, 12a, 15c, 15d |

TABLE A-continued

Exemplified Compounds.

| Compound | Structure | Select Embodiments 1-16 |
|---|---|---|
| 1.277 | 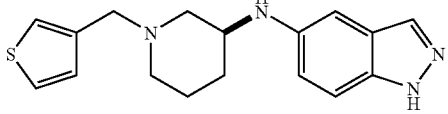<br>(S)-N-(1-(thiophen-3-ylmethyl)piperidin-3-yl)-1H-indazol-5-amine | 1c, 7, 8, 9, 10 |
| 1.278 | 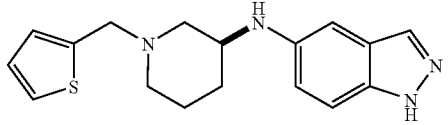<br>(S)-N-(1-(thiophen-2-ylmethyl)piperidin-3-yl)-1H-indazol-5-amine | 1c, 7, 8, 9, 10 |
| 1.279 | 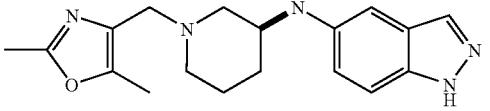<br>(S)-N-(1-((2,5-dimethyloxazol-4-yl)methyl)piperidin-3-yl)-1H-indazol-5-amine | 1c, 7, 8, 9, 10 |
| 1.280 | 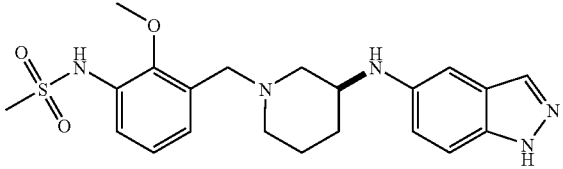<br>(S)-N-(3-((3-(1H-indazol-5-ylamino)piperidin-1-yl)methyl)-2-methoxyphenyl)methanesulfonamide | 1c, 7, 8, 9, 10, 12a, 15c, 15d |
| 1.281 | 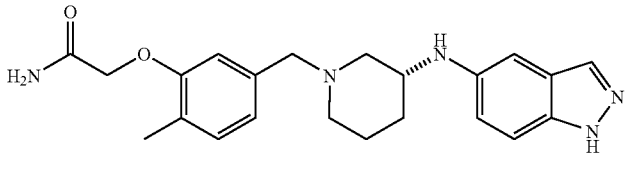<br>(R)-2-(5-((3-(1H-indazol-5-ylamino)piperidin-1-yl)methyl)-1H-indazol-5-ylamino)piperidin-1-yl)methyl)-2-methylphenoxy)acetamide | 1c, 7, 8, 9, 10, 12a, 15c, 15d |
| 1.282 | 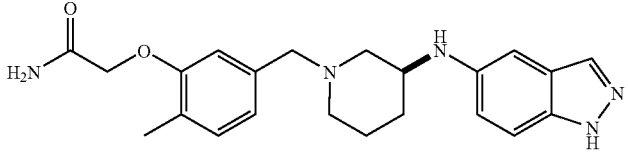<br>(S)-2-(5-((3-(1H-indazol-5-ylamino)piperidin-1-yl)methyl)-1H-indazol-5-ylamino)piperidin-1-yl)methyl)-2-methylphenoxy)acetamide | 1c, 7, 8, 9, 10, 12a, 15c, 15d |
| 2.001 | 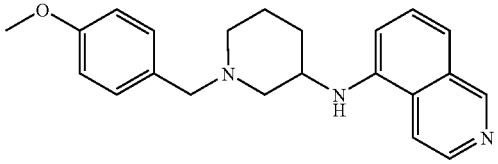<br>N-(1-(4-methoxybenzyl)piperidin-3-yl)isoquinolin-5-amine | 2c, 7, 8, 9, 10 |

TABLE A-continued

Exemplified Compounds.

| Compound | Structure | Select Embodiments 1-16 |
|---|---|---|
| 2.002 | N-(1-(4-methylsulfonyl)benzyl)piperidin-3-yl)isoquinolin-5-amine | 2c, 7, 8, 9, 10, 12, 15c |
| 2.003 | 3-((3-(isoquinolin-5-ylamino)piperidin-1-yl)methyl)benzonitrile | 2c, 7, 8, 9, 10, 12, 15c |
| 2.004 | N-(4-((3-(isoquinolin-5-ylamino)piperidin-1-yl)methyl)phenyl)acetamide | 2c, 7, 8, 9, 10, 12a, 15c, 15d |
| 2.005 | N-(1-(4-(methylsulfonyl)benzyl)pyrrolidin-3-yl)isoquinolin-5-amine | 2c, 7, 8, 9, 10, 12, 15c |
| 2.006 | N-(1-benzylpyrrolidin-3-yl)isoquinolin-5-amine | 2c, 7, 8, 9, 10 |
| 2.007 | 3-((3-(isoquinolin-5-ylamino)pyrrolidin-1-yl)methyl)benzonitrile | 2c, 7, 8, 9, 10, 12, 15c |

TABLE A-continued

Exemplified Compounds.

| Compound | Structure | Select Embodiments 1-16 |
| --- | --- | --- |
| 2.008 | N-(4-((3-(isoquinolin-5-ylamino)pyrrolidin-1-yl)methyl)phenyl)acetamide | 2c, 7, 8, 9, 10, 12a, 15c, 15d |
| 2.009 | N-(1-(4-(methylthio)benzyl)piperidin-3-yl)isoquinolin-5-amine | 2c, 7, 8, 9, 10, 12b, 15c, 15e |
| 2.010 | N-(1-(4-cyclopropylbenzyl)piperidin-3-yl)isoquinolin-5-amine | 2c, 7, 8, 9, 10, 11, 14c |
| 2.011 | N-(1-(3-cyclopropylbenzyl)piperidin-3-yl)isoquinolin-5-amine | 2c, 7, 8, 9, 10, 11, 14c |
| 2.012 | N-(1-(4-cyclopropylthio)benzyl)piperidin-3-yl)isoquinolin-5-amine | 2c, 7, 8, 9, 10, 12b, 15c, 15e |
| 2.013 | N-(1-benzylazepan-4-yl)isoquinolin-5-amine | 2c, 7, 8, 9, 10 |
| 2.014 | N-(1-(3,4-dichlorobenzyl)piperidin-3-yl)isoquinolin-5-amine | 2c, 7, 8, 9, 10 |

TABLE A-continued

Exemplified Compounds.

| Compound | Structure | Select Embodiments 1-16 |
| --- | --- | --- |
| 2.015 | 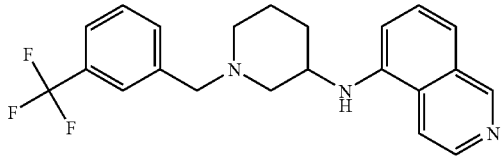<br>N-(1-(3-(trifluoromethyl)benzyl)piperidin-3-yl)isoquinolin-5-amine | 2c, 7, 8, 9, 10 |
| 2.016 | 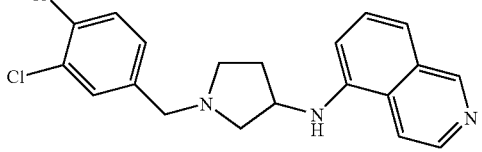<br>N-(1-(3,4-dichlorobenzyl)pyrrolidin-3-yl)isoquinolin-5-amine | 2c, 7, 8, 9, 10 |
| 2.017 | 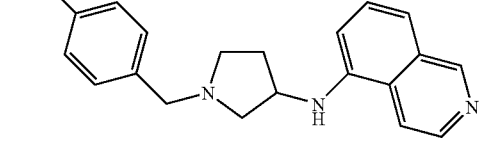<br>N-(1-(4-methoxybenzyl)pyrrolidin-3-yl)isoquinolin-5-amine | 2c, 7, 8, 9, 10 |
| 2.018 | 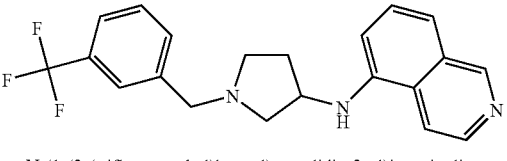<br>N-(1-(3-(trifluoromethyl)benzyl)pyrrolidin-3-yl)isoquinolin-5-amine | 2c, 7, 8, 9, 10 |
| 2.019 | 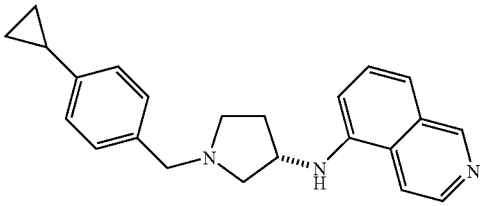<br>(S)-N-(1-(4-cyclopropylbenzyl)pyrrolidin-3-yl)isoquinolin-5-amine | 2c, 7, 8, 9, 10, 11, 14c |
| 2.020 | 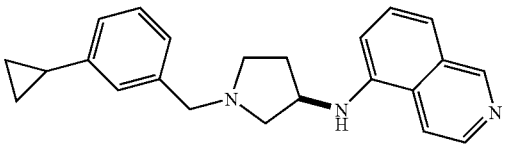<br>(R)-N-(1-(3-cyclopropylbenzyl)pyrrolidin-3-yl)isoquinolin-5-amine | 2c, 7, 8, 9, 10, 11, 14c |

TABLE A-continued

Exemplified Compounds.

| Compound | Structure | Select Embodiments 1-16 |
|---|---|---|
| 2.021 | (R)-N-(1-(4-(cyclopropylthio)benzyl)pyrrolidin-3-yl)isoquinolin-5-amine | 2c, 7, 8, 9, 10, 12b, 15c, 15e |
| 2.022 | (R)-N-(1-(4-cyclopropylbenzyl)pyrrolidin-3-yl)isoquinolin-5-amine | 2c, 7, 8, 9, 10, 11, 14c |
| 2.023 | (S)-N-(1-(3-cyclopropylbenzyl)pyrrolidin-3-yl)isoquinolin-5-amine | 2c, 7, 8, 9, 10, 11, 14c |
| 2.024 | (S)-N-(1-(4-(cyclopropylthio)benzyl)pyrrolidin-3-yl)isoquinolin-5-amine | 2c, 7, 8, 9, 10, 12b, 15c, 15e |
| 2.025 | (R)-N-(1-(4-methylbenzyl)pyrrolidin-3-yl)isoquinolin-5-amine | 2c, 7, 8, 9, 10 |
| 2.026 | (R)-N-(1-(4-(methylthio)benzyl)pyrrolidin-3-yl)isoquinolin-5-amine | 2c, 7, 8, 9, 10, 12b, 15c, 15e |

TABLE A-continued

Exemplified Compounds.

| Compound | Structure | Select Embodiments 1-16 |
| --- | --- | --- |
| 2.027 | (R)-N-(1-(4-chlorobenzyl)pyrrolidin-3-yl)isoquinolin-5-amine | 2c, 7, 8, 9, 10 |
| 2.028 | (S)-N-(1-(4-methylbenzyl)pyrrolidin-3-yl)isoquinolin-5-amine | 2c, 7, 8, 9, 10 |
| 2.029 | (S)-N-(1-(4-(methylthio)benzyl)pyrrolidin-3-yl)isoquinolin-5-amine | 2c, 7, 8, 9, 10, 12b, 15c, 15e |
| 2.030 | (S)-N-(1-(4-chlorobenzyl)pyrrolidin-3-yl)isoquinolin-5-amine | 2c, 7, 8, 9, 10 |
| 2.031 | (R)-N-(1-(4-ethynylbenzyl)pyrrolidin-3-yl)isoquinolin-5-amine | 2c, 7, 8, 9, 10, 11, 14c |
| 2.032 | (S)-2-(3-((3-(isoquinolin-5-ylamino)pyrrolidin-1-yl)methyl)phenoxy)ethanol | 2c, 7, 8, 9, 10, 12a, 15c, 15d |

TABLE A-continued

Exemplified Compounds.

| Compound | Structure | Select Embodiments 1-16 |
|---|---|---|
| 2.033 | 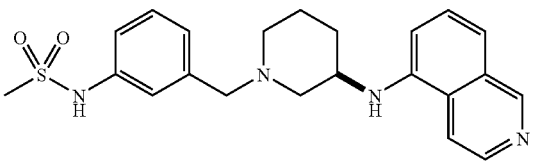<br>(R)-N-(3-((3-(isoquinolin-5-ylamino)piperidin-1-yl)methyl)phenyl)methanesulfonamide | 2c, 7, 8, 9, 10, 12a, 15c, 15d |
| 2.034 | 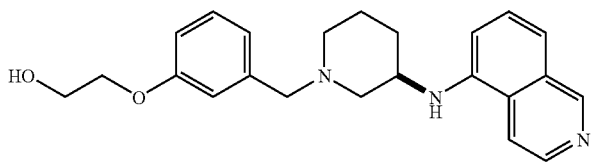<br>(R)-2-(3-((3-(isoquinolin-5-ylamino)piperidin-1-yl)methyl)phenoxy)ethanol | 2c, 7, 8, 9, 10, 12a, 15c, 15d |
| 2.035 | 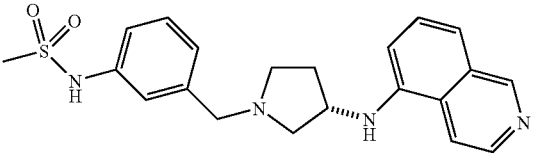<br>(S)-N-(3-((3-(isoquinolin-5-ylamino)pyrrolidin-1-yl)methyl)phenyl)methanesulfonamide | 2c, 7, 8, 9, 10, 12a, 15c, 15d |
| 2.036 | 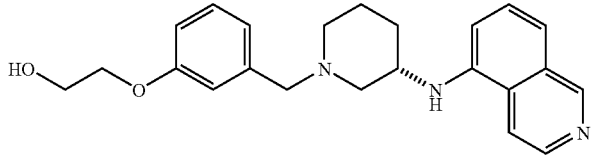<br>(S)-2-(3-((3-(isoquinolin-5-ylamino)piperidin-1-yl)methyl)phenoxy)ethanol | 2c, 7, 8, 9, 10, 12a, 15c, 15d |
| 2.037 | 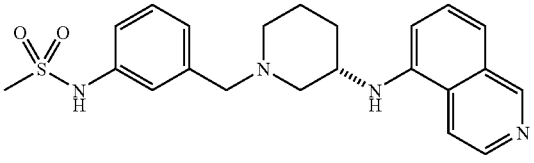<br>(S)-N-(3-((3-(isoquinolin-5-ylamino)piperidin-1-yl)methyl)phenyl)methanesulfonamide | 2c, 7, 8, 9, 10, 12a, 15c, 15d |
| 2.038 | 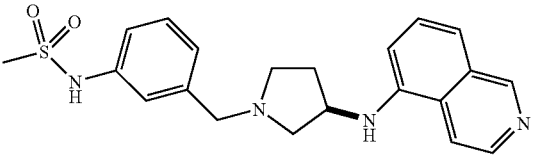<br>(R)-N-(3-((3-(isoquinolin-5-ylamino)pyrrolidin-1-yl)methyl)phenyl)methanesulfonamide | 2c, 7, 8, 9, 10, 12a, 15c, 15d |
| 2.039 | 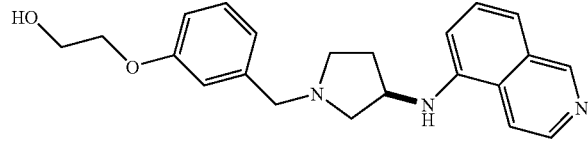<br>(R)-2-(3-((3-(isoquinolin-5-ylamino)pyrrolidin-1-yl)methyl)phenoxy)ethanol | 2c, 7, 8, 9, 10, 12a, 15c, 15d |

TABLE A-continued

Exemplified Compounds.

| Compound | Structure | Select Embodiments 1-16 |
|---|---|---|
| 2.040 | (R)-2-(3-((3-(isoquinolin-5-ylamino)pyrrolidin-1-yl)methyl)phenoxy)acetamide | 2c, 7, 8, 9, 10, 12a, 15c, 15d |
| 2.041 | (R)-N-(3-((3-(isoquinolin-5-ylamino)pyrrolidin-1-yl)methyl)phenyl)ethanesulfonamide | 2c, 7, 8, 9, 10, 12a, 15c, 15d |
| 2.042 | 2-(3-((3-(isoquinolin-5-ylamino)pyrrolidin-1-yl)methyl)phenoxy)ethanol | 2c, 7, 8, 9, 10, 12a, 15c, 15d |
| 2.043 | (R)-2-(3-((3-(isoquinolin-5-ylamino)pyrrolidin-1-yl)methyl)phenoxy)-1-morpholinoethanone | 2c, 7, 8, 9, 10, 12a, 15c, 15d |
| 2.044 | (R)-2-(3-((3-(isoquinolin-5-ylamino)pyrrolidin-1-yl)methyl)phenoxy)acetic acid | 2c, 7, 8, 9, 10, 12a, 15c, 15d |
| 2.045 | (S)-N-(1-(4-methylbenzyl)piperidin-3-yl)isoquinolin-5-amine | 2c, 7, 8, 9, 10 |
| 2.046 | (R)-N-(1-benzylpyrrolidin-3-yl)isoquinolin-5-amine | 2c, 7, 8, 9, 10 |

TABLE A-continued

Exemplified Compounds.

| Compound | Structure | Select Embodiments 1-16 |
|---|---|---|
| 2.047 | 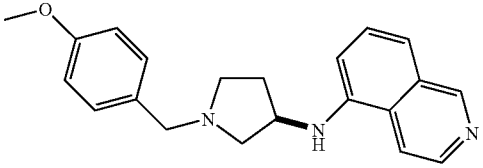<br>(R)-N-(1-(4-methoxybenzyl)pyrrolidin-3-yl)isoquinolin-5-amine | 2c, 7, 8, 9, 10 |
| 2.048 | 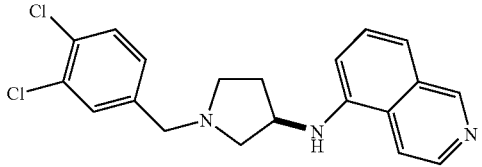<br>(R)-N-(1-(3,4-dichlorobenzyl)pyrrolidin-3-yl)isoquinolin-5-amine | 2c, 7, 8, 9, 10 |
| 2.049 | 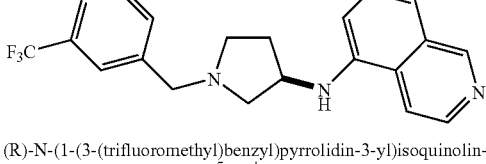<br>(R)-N-(1-(3-(trifluoromethyl)benzyl)pyrrolidin-3-yl)isoquinolin-5-amine | 2c, 7, 8, 9, 10 |
| 2.050 | 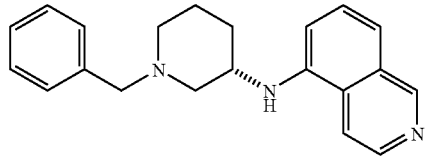<br>(S)-N-(1-benzylpiperidin-3-yl)isoquinolin-5-amine | 2c, 7, 8, 9, 10 |
| 2.051 | 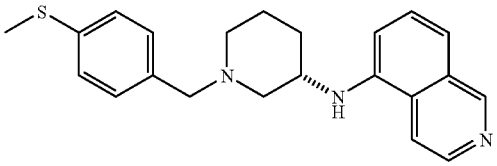<br>(S)-N-(1-(4-(methylthio)benzyl)piperidin-3-yl)isoquinolin-5-amine | 2c, 7, 8, 9, 10, 12b, 15c, 15e |
| 2.052 | 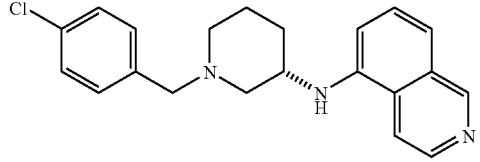<br>(S)-N-(1-(4-chlorobenzyl)piperidin-3-yl)isoquinolin-5-amine | 2c, 7, 8, 9, 10 |

TABLE A-continued

Exemplified Compounds.

| Compound | Structure | Select Embodiments 1-16 |
|---|---|---|
| 2.053 | (S)-N-(1-(4-methoxybenzyl)piperidin-3-yl)isoquinolin-5-amine | 2c, 7, 8, 9, 10 |
| 2.054 | (R)-N-(5-((3-(isoquinolin-5-ylamino)pyrrolidin-1-yl)methyl)-2-methylphenyl)ethanesulfonamide | 2c, 7, 8, 9, 10, 12a, 15c, 15d |
| 2.055 | (R)-N-(1-(benzofuran-5-ylmethyl)pyrrolidin-3-yl)isoquinolin-5-amine | 2c, 7, 8, 9, 10 |
| 2.056 | (R)-N-(1-((2,3-dihydrobenzo[b][1,4]dioxin-6-yl)methyl)pyrrolidin-3-yl)isoquinolin-5-amine | 2c, 7, 8, 9, 10 |
| 2.057 | (R)-N-(1-((1H-indol-6-yl)methyl)pyrrolidin-3-yl)isoquinolin-5-amine | 2c, 7, 8, 9, 10 |
| 2.058 | (R)-2-(6-((3-(isoquinolin-5-ylamino)pyrrolidin-1-yl)methyl)-1H-indol-1-yl)acetamide | 2c, 7, 8, 9, 10, 13, 16c |

TABLE A-continued

Exemplified Compounds.

| Compound | Structure | Select Embodiments 1-16 |
|---|---|---|
| 2.059 | (R)-2-(5-((3-(isoquinolin-5-ylamino)pyrrolidin-1-yl)methyl)-1H-indol-1-yl)acetamide | 2c, 7, 8, 9, 10, 13, 16c |
| 2.060 | (R)-2-(6-((3-(isoquinolin-5-ylamino)pyrrolidin-1-yl)methyl)-1H-indol-1-yl)ethanol | 2c, 7, 8, 9, 10, 13, 16c |
| 2.061 | (R)-3-((3-(isoquinolin-5-ylamino)pyrrolidin-1-yl)methyl)phenol | 2c, 7, 8, 9, 10 |
| 2.062 | (R)-N-(1-(3,4-difluorobenzyl)pyrrolidin-3-yl)isoquinolin-5-amine | 2c, 7, 8, 9, 10 |
| 2.063 | (R)-N-(3-((3-(isoquinolin-5-ylamino)pyrrolidin-1-yl)methyl)benzyl)acetamide | 2c, 7, 8, 9, 10, 13, 16c |
| 2.064 | (R)-2-(5-((3-(isoquinolin-5-ylamino)pyrrolidin-1-yl)methyl)-2-methylphenoxy)ethanol | 2c, 7, 8, 9, 10, 12a, 15c, 15d |

TABLE A-continued

Exemplified Compounds.

| Compound | Structure | Select Embodiments 1-16 |
|---|---|---|
| 2.065 | 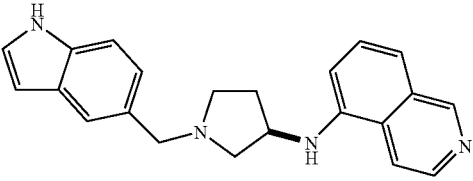<br>(R)-N-(1-((1H-indol-5-yl)methyl)pyrrolidin-3-yl)isoquinolin-5-amine | 2c, 7, 8, 9, 10 |
| 2.066 | 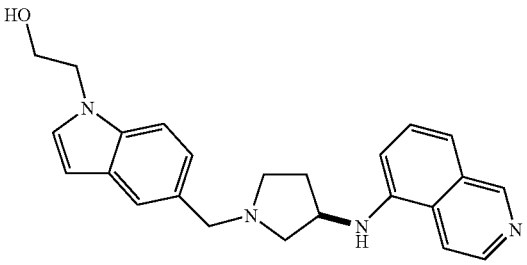<br>(R)-2-(5-((3-(isoquinolin-5-ylamino)pyrrolidin-1-yl)methyl)-1H-indol-1-yl)ethanol | 2c, 7, 8, 9, 10, 13, 16c |
| 2.067 | 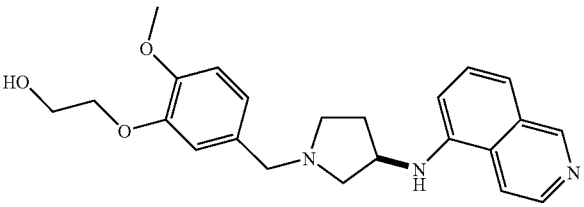<br>(R)-2-(5-((3-(isoquinolin-5-ylamino)pyrrolidin-1-yl)methyl)-2-methoxyphenoxy)ethanol | 2c, 7, 8, 9, 10, 12a, 15c, 15d |
| 2.068 | 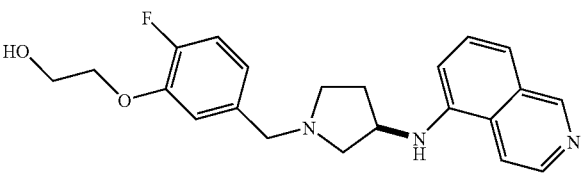<br>(R)-2-(2-fluoro-5-((3-(isoquinolin-5-ylamino)pyrrolidin-1-yl)methyl)phenoxy)ethanol | 2c, 7, 8, 9, 10, 12a, 15c, 15d |
| 2.069 | 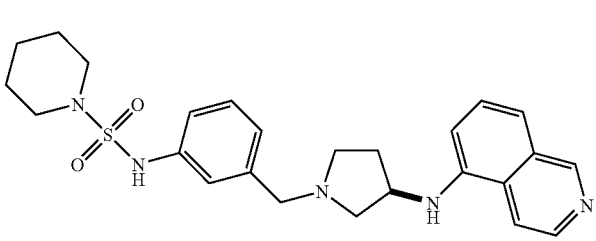<br>(R)-N-(3-((3-(isoquinolin-5-ylamino)pyrrolidin-1-yl)methyl)phenyl)piperidine-1-sulfonamide | 2c, 7, 8, 9, 10, 12a, 15c, 15d |

TABLE A-continued

Exemplified Compounds.

| Compound | Structure | Select Embodiments 1-16 |
|---|---|---|
| 2.070 | (R)-N-(1-((1-(methylsulfonyl)-1,2,3,4-tetrahydroquinolin-6-yl)methyl)pyrrolidin-3-yl)isoquinolin-5-amine | 2c, 7, 8, 9, 10, 12b, 15c, 15e |
| 2.071 | (R)-tert-butyl 2-(5-(((3-(isoquinolin-5-ylamino)pyrrolidin-1-yl)methyl)2-methylphenoxy)acetate | 2c, 7, 8, 9, 10, 12a, 15c, 15d |
| 2.072 | (R)-2-(3-((3-(isoquinolin-5-ylamino)pyrrolidin-1-yl)methyl)-1H-indol-1-yl)ethanol | 2c, 7, 8, 9, 10, 13, 16c |
| 2.073 | (R)-2-(5-(((3-(isoquinolin-5-ylamino)pyrrolidin-1-yl)methyl)-2-methylphenoxy)acetic acid | 2c, 7, 8, 9, 10, 12a, 15c, 15d |
| 2.074 | (R)-N-(1-((1H-benzo[d]imidazol-2-yl)methyl)pyrrolidin-3-yl)isoquinolin-5-amine | 2c, 7, 8, 9, 10 |

TABLE A-continued

Exemplified Compounds.

| Compound | Structure | Select Embodiments 1-16 |
|---|---|---|
| 2.075 | (R)-N-(1-((1-methyl-1H-benzo[d]imidazol-2-yl)methyl)pyrrolidin-3-yl)isoquinolin-5-amine | 2c, 7, 8, 9, 10 |
| 2.076 | (R)-N-(5-((3-(isoquinolin-5-ylamino)pyrrolidin-1-yl)methyl)-2-methylphenyl)methanesulfonamide | 2c, 7, 8, 9, 10, 12a, 15c, 15d |
| 2.077 | (R)-N-(5-((3-(isoquinolin-5-ylamino)pyrrolidin-1-yl)methyl)-2-methylphenyl)-N′,N′ dimethylaminosulfamide | 2c, 7, 8, 9, 10, 12a, 15c, 15d |
| 2.078 | (R)-N-(3-((3-(isoquinolin-5-ylamino)pyrrolidin-1-yl)methyl)-2-methylphenyl)methanesulfonamide | 2c, 7, 8, 9, 10, 12a, 15c, 15d |
| 2.079 | (R)-N-(3-((3-(isoquinolin-5-ylamino)pyrrolidin-1-yl)methyl)-2-methylphenyl)-N′,N′ dimethylaminosulfamide | 2c, 7, 8, 9, 10, 12a, 15c, 15d |
| 2.080 | (R)-5-(1-(3-(2-hydroxyethoxy)-4-methylbenzyl)pyrrolidin-3-ylamino)isoquinoline 2-oxide | 2b, 6b, 8, 9, 10, 12a, 15b, 15d |

TABLE A-continued

Exemplified Compounds.

| Compound | Structure | Select Embodiments 1-16 |
|---|---|---|
| 2.081 | 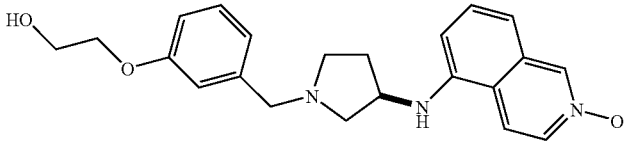<br>(R)-5-(1-(3-(2-hydroxyethoxy)benzyl)pyrrolidin-3-ylamino)isoquinoline 2-oxide | 2b, 6b, 8, 9, 10, 12a, 15b, 15d |
| 2.082 | 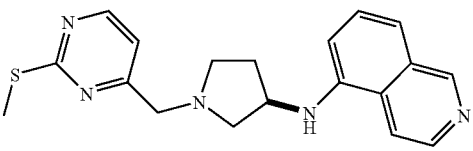<br>(R)-N-(1-((2-(methylthio)pyrimidin-4-yl)methyl)pyrrolidin-3-yl)isoquinolin-5-amine | 2c, 7, 8, 9, 10, 12b, 15c, 15e |
| 2.083 | 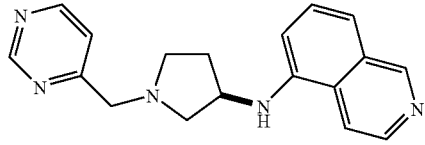<br>(R)-N-(1-(pyrimidin-4-ylmethyl)pyrrolidin-3-yl)isoquinolin-5-amine | 2c, 7, 8, 9, 10 |
| 2.084 | 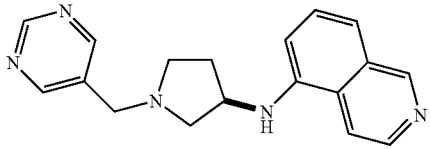<br>(R)-N-(1-(pyrimidin-5-ylmethyl)pyrrolidin-3-yl)isoquinolin-5-amine | 2c, 7, 8, 9, 10 |
| 2.085 | 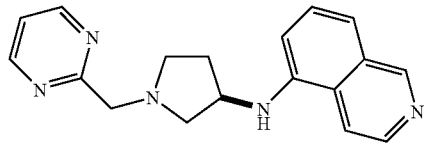<br>(R)-N-(1-(pyrimidin-2-ylmethyl)pyrrolidin-3-yl)isoquinolin-5-amine | 2c, 7, 8, 9, 10 |
| 2.086 | 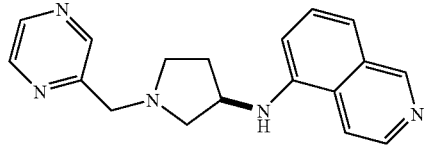<br>(R)-N-(1-(pyrazin-2-ylmethyl)pyrrolidin-3-yl)isoquinolin-5-amine | 2c, 7, 8, 9, 10 |
| 2.087 | 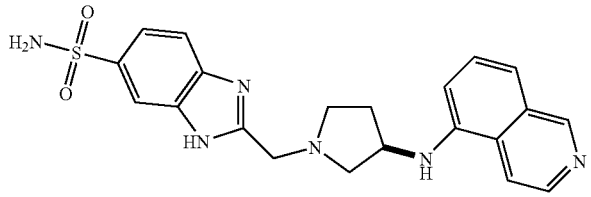<br>(R)-2-((3-(isoquinolin-5-ylamino)pyrrolidin-1-yl)methyl)-1H-benzo[d]imidazole-6-sulfonamide | 2c, 7, 8, 9, 10, 12b, 15c, 15e |

TABLE A-continued

Exemplified Compounds.

| Compound | Structure | Select Embodiments 1-16 |
|---|---|---|
| 2.088 | (R)-N-(1-thiophen-3-ylmethyl)pyrrolidin-3-yl)isoquinolin-5-amine | 2c, 7, 8, 9, 10 |
| 2.089 | (R)-N-(1-((5-nitrothiophen-3-yl)methyl)pyrrolidin-3-yl)isoquinolin-5-amine | 2c, 7, 8, 9, 10 |
| 2.090 | (R)-N-(1-(thiophen-2-ylmethyl)pyrrolidin-3-yl)isoquinolin-5-amine | 2c, 7, 8, 9, 10 |
| 2.091 | (R)-N-(1-((2,5-dimethyloxazol-4-yl)methyl)pyrrolidin-3-yl)isoquinolin-5-amine | 2c, 7, 8, 9, 10 |
| 2.092 | (R)-5-(1-(3-(2-hydroxyethoxy)benzyl)pyrrolidin-3-ylamino)isoquinolin-1(2H)-one | 2b, 6b, 8, 9, 10, 12a, 15b, 15d |
| 2.093 | (R)-5-(1-(3-(2-hydroxyethoxy)-4-methylbenzyl)pyrrolidin-3-ylamino)isoquinolin-1(2H)-one | 2b, 6b, 8, 9, 10, 12a, 15b, 15d |
| 2.094 | (R)-2-(5-((3-(1-methoxyisoquinolin-5-ylamino)pyrrolidin-1-yl)methyl)-2-methylphenoxy)ethanol | 2b, 6b, 8, 9, 10, 12a, 15b, 15d |

TABLE A-continued

Exemplified Compounds.

| Compound | Structure | Select Embodiments 1-16 |
|---|---|---|
| 2.095 | (R)-2-(3-((3-(1-methoxyisoquinolin-5-ylamino)pyrrolidin-1-yl)methyl)phenoxy)ethanol | 2b, 6b, 8, 9, 10, 12a, 15b, 15d |
| 2.096 | (R)-N-(3-((3-(isoquinolin-5-ylamino)pyrrolidin-1-yl)methyl)-2-methoxyphenyl)methanesulfonamide | 2c, 7, 8, 9, 10, 12a, 15c, 15d |
| 2.097 | (R)-N-(3-((3-(isoquinolin-5-ylamino)pyrrolidin-1-yl)methyl)-2-methoxyphenyl)-N',N' dimethylaminosulfamide | 2c, 7, 8, 9, 10, 12a, 15c, 15d |
| 2.098 | (R)-N-(5-((3-(isoquinolin-5-ylamino)pyrrolidin-1-yl)methyl)-2-methoxyphenyl)methanesulfonamide | 2c, 7, 8, 9, 10, 12a, 15c, 15d |
| 2.099 | (R)-2-(5-((3-(isoquinolin-5-ylamino)pyrrolidin-1-yl)methyl)-2-methylphenoxy)acetamide | 2c, 7, 8, 9, 10, 12a, 15c, 15d |
| 2.100 | (R)-2-(2-((3-(isoquinolin-5-ylamino)pyrrolidin-1-yl)methyl)-1H-benzo[d]imidazol-6-yloxy)ethanol | 2c, 7, 8, 9, 10, 12a, 15c, 15d |

TABLE A-continued

Exemplified Compounds.

| Compound | Structure | Select Embodiments 1-16 |
|---|---|---|
| 3.001 | 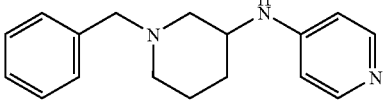<br>N-(1-benzylpiperidin-3-yl)pyridin-4-amine | 3c, 7, 8, 9, 10 |
| 3.002 | 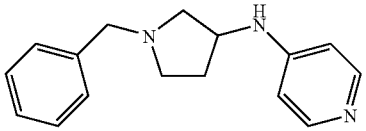<br>N-(1-benzylpyrrolidin-3-yl)pyridin-4-amine | 3c, 7, 8, 9, 10 |
| 4.001 | 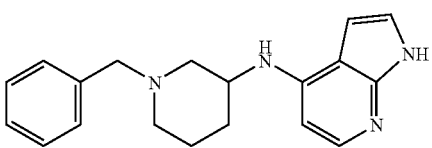<br>N-(1-benzylpiperidin-3-yl)-1H-pyrrolo[2,3-b]pyridin-4-amine | 4c, 7, 8, 9, 10 |
| 4.002 | 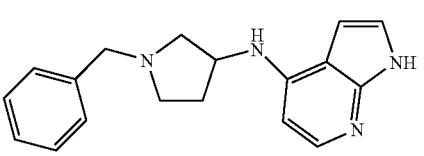<br>N-(1-benzylpyrrolidin-3-yl)-1H-pyrrolo[2,3-b]pyridin-4-amine | 4c, 7, 8, 9, 10 |
| 5.001 | 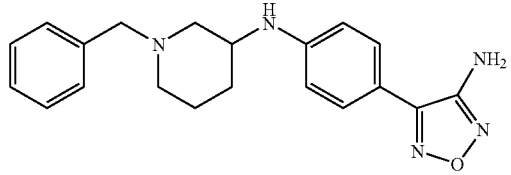<br>4-(4-(1-benzylpiperidin-3-ylamino)phenyl)-1,2,5-oxadiazol-3-amine | 5a, 7, 8, 9, 10 |
| 5.002 | 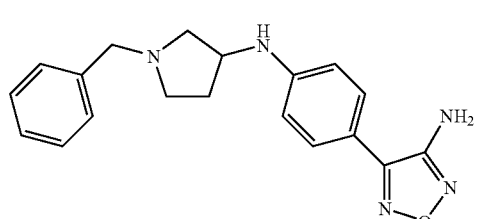<br>4-(4-(1-benzylpyrrolidin-3-ylamino)phenyl)-1,2,5-oxadiazol-3-amine | 5a, 7, 8, 9, 10 |

Preferred ROCK inhibitor compounds of this invention include, but are not limited to the ROCK inhibitor compounds of embodiments 5, 14, 15, 16, 17, 18, 19, 20, and 21 as described above, and their associated salts, tautomers, solvates, or hydrates. In particular, preferred Compounds include 1.074, 1.075, 1.076, 1.077, 1.079, 1.091, 1.093, 1.108, 1.109, 1.123, 1.124, 1.126, 1.131, 1.132, 1.133, 1.134, 1.135, 1.136, 1.137, 1.138, 1.141, 1.148, 1.149, 1.150, 1.152, 1.153, 1.155, 1.156, 1.157, 1.158, 1.161, 1.162, 1.163, 1.164, 1.165, 1.166, 1.171, 1.173, 1.175, 1.176, 1.186, 1.193, 1.195, 1.197, 1.200, 1.206, 1.212, 1.213, 1.215, 1.217, 1.219, 1.223, 1.233, 1.236, 1.237, 1.238, 1.239, 1.249, 1.252, 1.253, 1.258, 1.259, 1.260, 1.261, 1.262, 1.270, 1.273, 1.275, 1.277, 1.281, 2.025, 2.026, 2.031, 2.038, 2.039, 2.041, 2.046, 2.047, 2.054, 2.055, 2.057, 2.058, 2.059, 2.060, 2.061, 2.064, 2.065, 2.066, 2.067, 2.068, 2.069, 2.072, 2.073, 2.076, 2.077, 2.078, 2.079, 2.082, 2.096, 2.097, and 2.099.

Pharmaceutical Formulations

The present invention provides a pharmaceutical formulation comprising compounds of Formula I or II and a pharmaceutically acceptable carrier. Pharmaceutically acceptable carriers can be selected by those skilled in the art using conventional criteria. Pharmaceutically acceptable carriers include, but are not limited to, saline solution, aqueous electrolyte solutions, isotonicity modifiers, water polyethers such as polyethylene glycol, polyvinyls such as polyvinyl alcohol and povidone, cellulose derivatives such as methylcellulose and hydroxypropyl methylcellulose, polymers of acrylic acid such as carboxypolymethylene gel, polysaccharides such as dextrans, and glycosaminoglycans such as sodium hyaluronate and salts such as sodium chloride and potassium chloride.

The pharmaceutical formulation useful for the present invention in general is an aqueous solution comprising water, suitable ionic or non-ionic tonicity modifiers, suitable buffering agents, and a compound of Formula I or II. In one embodiment, the compound is at 0.005 to 3% w/v, and the aqueous solution has a tonicity of 200-400 mOsm/kG and a pH of 4-9.

In one embodiment, the tonicity modifier is ionic such as NaCl, for example, in the amount of 0.5-0.9% w/v, preferably 0.6-0.9% w/v.

In another embodiment, the tonicity modifier is non-ionic, such as mannitol, dextrose, in the amount of at least 2%, or at least 2.5%, or at least 3%, and no more than 7.5%; for example, in the range of 3-5%, preferably 4-5% w/v.

The pharmaceutical formulation can be sterilized by filtering the formulation through a sterilizing grade filter, preferably of a 0.22-micron nominal pore size. The pharmaceutical formulation can also be sterilized by terminal sterilization using one or more sterilization techniques including but not limited to a thermal process, such as an autoclaving process, or a radiation sterilization process, or using pulsed light to produce a sterile formulation. In one embodiment, the pharmaceutical formulation is a concentrated solution of the active ingredient; the formulation can be serially diluted using appropriate acceptable sterile diluents prior to administration.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents such as those set forth above, and flavoring agents can be added to provide palatable oral preparations. These compositions can be preserved by the addition of an anti-oxidant such as ascorbic acid.

Pharmaceutical compositions of the invention can be in the form of oil-in-water emulsions. The oily phase can be a vegetable oil, for example olive oil or arachis oil, or a mineral oil, for example liquid paraffin or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions can also contain sweetening and flavoring agents.

Pharmaceutical compositions of the invention can be in the form of an aerosol suspension of respirable particles comprising the active compound, which the subject inhales. The respirable particles can be liquid or solid, with a particle size sufficiently small to pass through the mouth and larynx upon inhalation. In general, particles having a size of about 1 to 10 microns, preferably 1-5 microns, are considered respirable.

The pharmaceutical formulation for systemic administration such as injection and infusion is generally prepared in a sterile medium. The active ingredient, depending on the vehicle and concentration used, can either be suspended or dissolved in the vehicle. Adjuvants such as local anesthetics, preservatives and buffering agents can also be dissolved in the vehicle. The sterile injectable preparation can be a sterile injectable solution or suspension in a non-toxic acceptable diluent or solvent. Among the acceptable vehicles and solvents that can be employed are sterile water, saline solution, or Ringer's solution.

The pharmaceutical compositions for oral administration contain active compounds in the form of tablets, lozenges, aqueous or oily suspensions, viscous gels, chewable gums, dispersible powders or granules, emulsion, hard or soft capsules, or syrups or elixirs.

For oral use, an aqueous suspension is prepared by addition of water to dispersible powders and granules with a dispersing or wetting agent, suspending agent one or more preservatives, and other excipients. Suspending agents include, for example, sodium carboxymethylcellulose, methylcellulose and sodium alginate. Dispersing or wetting agents include naturally-occurring phosphatides, condensation products of an allylene oxide with fatty acids, condensation products of ethylene oxide with long chain aliphatic alcohols, condensation products of ethylene oxide with partial esters from fatty acids and a hexitol, and condensation products of ethylene oxide with partial esters derived from fatty acids and hexitol anydrides. Preservatives include, for example, ethyl, and n-propyl p-hydroxybenzoate. Other excipients include sweetening agents (e.g., sucrose, saccharin), flavoring agents and coloring agents. Those skilled in the art will recognize the many specific excipients and wetting agents encompassed by the general description above.

For oral application, tablets are prepared by mixing the active compound with nontoxic pharmaceutically acceptable excipients suitable for the manufacture of tablets. These excipients can be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets can be uncoated or they can be coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil. Formulation for oral use can also be presented as chewable gums by embedding the active ingredient in gums so that the active ingredient is slowly released upon chewing.

The pharmaceutical compositions can be in the form of suppositories, which are prepared by mixing the active ingredient with a suitable non-irritating excipient that is solid at ordinary temperatures but liquid at the rectal temperature and will thus melt in the rectum to release the compound. Such excipients include cocoa butter and polyethylene glycols.

Method of Treating Diseases Using Rho Kinase Inhibitor Compounds of Formula I or II The present invention is useful in treating diseases associated with alteration in cellular integrity including endothelial permeability, excessive cell proliferation or tissue remodeling. The present invention is particularly effective in treating diseases associated with alterations in cellular integrity such as diabetic nephropathy, malaria, or cancer.

Diabetic Nephropathy

Rho kinase inhibitor compounds of Formula I or II inhibit the ROCK-mediated regulation of cell migration, cytokine and chemokine secretion, proliferation and endothelial cell permeability, thus they are useful in treating the remodeling, fibrosis and microvascular complications seen in diabetic nephropathy.

The present invention is directed to a method for treating diabetic nephropathy. The method comprises the steps of: identifying a subject suffering from diabetic nephropathy and administering to the subject an effective amount of a Rho kinase inhibitor compound of Formula I or II to treat diabetic nephropathy A method for treating diabetic nephropathy is based on the properties of Rho kinase inhibitor compounds of Formula I or II to reduce at least one of the following processes contributing to pathophysiologies that accompany these disorders: cell migration, cytokine and chemokine secretion, proliferation or endothelial cell permeability.

Indicia of efficacy for treating diabetic nephropathy by the present invention include demonstrable improvement in the measurable signs, symptoms, and other variables clinically relevant to the disease. Such improvements include reduced glomerular hypertension and hyperfiltration, decreased microalbuminuria, and reduction in numbers of dipstick-positive proteinuria. Other improvements include reduction in features of tubulo-interstitial disease such as hyperkalemia and type IV renal tubular acidosis.

Malaria

Rho kinase inhibitor compounds of Formula I and II inhibit the ROCK-mediated regulation of cytokine secretion, cellular adherence and focal adhesions, and endothelial apoptosis, thus they are useful in preventing inflammation, cytoadherence to endothelial cells and loss of endothelial barrier function seen in malaria.

The present invention is directed to a method of treating malaria. The method comprises the steps of first identifying a subject suffering from malaria, then administering to the subject an effective amount of a Rho kinase inhibitor compound of Formula I or II to treat malaria.

A method for treating malaria is based on the properties of the Rho kinase inhibitor compounds of Formula I or II to reduce at least one of the following processes contributing to pathophysiologies that accompany these disorders: inflammation, cytoadherence or endothelial barrier function.

Indicia of efficacy to treat malaria and other diseases involving parasitic cytoadherence include prevention of RhoA/Rho-kinase pathway activation, decrease in *P. falciparum* induced endothelial cell apoptosis, reversion of *P. falciparum* induced endothelial permeability, decreased amounts of inflammatory cytokines due to endothelial activation, decrease in fever, malaise, fatigue, muscle aches, back pain, headache, dizziness, loss of appetite, nausea, vomiting, abdominal pain, diarrhea, malaria-induced anemia and jaundice, decreased destruction of red blood cells and demonstrable improvement in other measurable signs, symptoms and other variables clinically relevant to malaria.

Cancer

Rho kinase inhibitor compounds of Formula I or II inhibit the ROCK-mediated regulation of proliferation, focal adhesions and cell motility, thus they are useful in treating the angiogenesis, tumor cell migration, metastasis or tumor growth seen in cancer.

The present invention is directed to a method for treating proliferation, adhesions and cell motility that underlie angiogenesis, tumor cell migration and metastasis in cancers such as acute lymphoblastic leukemia, acute myeloid leukemia, adrenocortical carcinoma, AIDS-related cancers, AIDS-related lymphoma, anal cancer, appendix cancer, astrocytoma (cerebellar), astrocytoma (cerebral), basal cell carcinoma, bile duct cancer, bladder cancer, bone cancer (osteosarcoma and malignant fibrous histiocytoma), brain tumor, brain stem glioma, medulloblastoma, medulloepithelioma, pineal parenchymal tumors, supratentorial primitive neuroectodermal tumors and pineoblastoma, visual pathway and hypothalamic glioma, brain and spinal cord tumors, breast cancer, bronchial tumors, burkitt lymphoma, carcinoid tumor, gastrointestinal carcinoid tumor, carcinoma, central nervous system lymphoma, malignant glioma, cervical cancer, chordoma, chronic lymphocytic leukemia, chronic myelogenous leukemia, chronic myeloproliferative disorders, colon cancer, colorectal cancer, cutaneous T-cell lymphoma, endometrial cancer, ependymoblastoma, ependymoma, esophageal cancer, extracranial germ cell tumor, extragonadal germ cell tumor, extrahepatic bile duct cancer, intraocular melanoma, retinoblastoma, gallbladder cancer, gastric cancer, gastrointestinal carcinoid tumor, gastrointestinal stromal tumor, germ cell tumor (extracranial), germ cell tumor (extragonadal), germ cell tumor (ovarian), gestational trophoblastic tumor, glioma, hairy cell leukemia, head and neck cancer, hepatocellular (liver) cancer, hypopharyngeal cancer, intraocular melanoma, islet cell tumors, Kaposi sarcoma, kidney (renal cell) cancer, laryngeal cancer, leukemia (acute lymphoblastic), lip and oral cavity cancer, liver cancer, lung cancer (non-small cell), lung cancer (small cell), lymphoma (Hodgkin), lymphoma (non-Hodgkin), lymphoma (primary central nervous system), macroglobulinemia (Waldenstrom), melanoma, merkel cell carcinoma, mesothelioma, metastatic squamous neck cancer, mouth cancer, multiple endocrine neoplasia syndrome, multiple myeloma/plasma cell neoplasm, mycosis fungoides, myelodysplastic syndromes, myelodysplastic/myeloproliferative diseases, myelogenous leukemia (chronic), myeloid leukemia (acute), multiple myeloma, nasal cavity and paranasal sinus cancer, nasopharyngeal cancer, neuroblastoma, oropharyngeal cancer, ovarian cancer, ovarian epithelial cancer, ovarian germ cell tumor, ovarian low malignant potential tumor, pancreatic cancer, papillomatosis, parathyroid cancer, penile cancer, pharyngeal cancer, pheochromocytoma, pineal parenchymal tumors of intermediate differentiation, pineoblastoma and supratentorial primitive neuroectodermal tumors, pituitary tumor, pleuropulmonary blastoma, prostate cancer, rectal cancer, renal pelvis and ureter (transitional cell cancer), retinoblastoma, rhabdomyosarcoma, salivary gland cancer, sarcoma (Ewing family of tumors), sarcoma (soft tissue), Sezary syndrome, skin cancer (nonmelanoma), skin carcinoma (Merkel cell), small intestine cancer, soft tissue sarcoma, squamous cell carcinoma, stomach (Gastric) cancer, supratentorial primitive neuroectodermal tumors, T-cell lymphoma (Cutaneous), testicular cancer, throat cancer, thymoma and thymic carcinoma, thyroid cancer, transitional cell cancer of the renal pelvis and ureter, urethral cancer, uterine cancer (Endometrial), uterine sarcoma, vaginal cancer, vulvar cancer, Waldenstrom macroglobulinemia and Wilms tumor. The present method preferably treats hepatomas, leukemias, breast cancer, lung cancers, ovarian cancers, gastric cancers, or gliomas. The method comprises the steps of: identifying a subject suffering from cancer, and administering to the subject an effective amount of a Rho kinase inhibitor compound of Formula I or II to treat the cancer.

A method for treating cancer is based on the properties of the Rho kinase inhibitor compounds of Formula I or Formula II to reduce at least one of the following processes contributing to pathophysiologies that accompany these disorders: proliferation, cytoadhesion, cell motility, angiogenesis, tumor cell migration and metastasis, or proliferation.

Indicia of efficacy for the treatment of cancer by the present invention include demonstrable improvement in measurable signs, symptoms and other clinically relevant variables. Such improvements include: slow progression of tumor growth, decreased tumor size, fewer tumors or tumor cell count, prevention of metastasis, decrease in weight loss, increase in weight gain, increased appetite, fewer headaches/fevers, fewer non-healing sores/skin changes. Higher life expectancy would also be a marker of effective treatment.

An effective amount of a Formula I or II compound is administered to a patient in need of such treatment. The patient either already has the symptoms of at least one above-mentioned disease, or is identified as being at risk of at least one above-mentioned disease. The compound is administered at a frequency that achieves desired efficacy. What constitutes desired efficacy is determined by a physician or other health-care professional. Whether or not sufficient efficacy has been reached is determined by indicia of efficacy for the specific disease. After an initial dose, additional doses are optionally administered if judged to be necessary by a health-care professional.

Methods of Administration

The present invention is particularly effective in diseases or conditions associated with alterations in endothelial permeability, excessive cell proliferation or tissue remodeling such as diabetic nephropathy, malaria, or cancer. Any method of delivering the compound to the target tissues, including local administration and systemic administration, is suitable for the present invention.

In one embodiment, the active compound is delivered by systemic administration; the compound first reaches plasma and then distributes into the target tissues. Examples of systemic administration include oral ingestion, or intravenous or subcutaneous or intraperitoneal or intrathecal or intramuscular administration.

Additional method of systemic administration of the active compound to a subject involves administering a suppository form of the active compound, such that a therapeutically effective amount of the compound reaches the target sites via systemic absorption and circulation.

Another method of systemically administering the active compounds to the subject involves administering a liquid/liquid suspension in the form of eye drops or eye wash or nasal drops of a liquid formulation, or a nasal spray of respirable particles that the subject inhales. Liquid pharmaceutical compositions of the active compound for producing a nasal spray or nasal or eye drops can be prepared by combining the active compound with a suitable vehicle, such as sterile pyrogen free water or sterile saline by techniques known to those skilled in the art.

The active compounds can also be systemically administered to the subject through absorption by the skin using transdermal patches or pads. The active compounds are absorbed into the bloodstream through the skin. Plasma concentration of the active compounds can be controlled by using patches containing different concentrations of active compounds.

For systemic administration, plasma concentrations of active compounds delivered can vary according to compounds; but are generally $1\times10^{-10}$-$1\times10^{-4}$ moles/liter, and preferably $1\times10^{-8}$-$1\times10^{-5}$ moles/liter.

Dosage level about 0.01-140 mg per kg (about 0.5 mg to about 7 g per patient per day) is useful in the treatment or preventions of conditions involving an inflammatory response. Preferred dosage levels are about 0.05-100, or 0.1-100, or 1-100 mg/kg body weight per day. The amount of active ingredient that can be combined with the carrier materials to produce a single dosage form will vary depending upon the host treated and the particular mode of administration. Dosage unit forms will generally contain between from about 1 mg to about 500 mg of an active ingredient.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more can be administered to achieve adequate steady state levels. The maximum total dose in general does not exceed about 2 g/day for a 40 to 80 kg human patient.

Frequency of dosage can also vary depending on the compound used and the particular disease treated. However, for treatment of most disorders, a dosage regimen of p.r.n, 4 times daily, three times daily, or less is preferred, with a dosage regimen of once daily or 2 times daily being particularly preferred.

In another embodiment, the active compound is delivered by inhalation, topical application, or targeted drug delivery to the target tissues. Methods of inhalation include liquid instillation, instillation as a pressurized fluid preparation via metered dose inhaler or equivalent, or inhalation of an aerosolized solution via nebulizer (preferred), inhalation of dry powder (more preferred), and directing soluble or dried material into the air stream during mechanical ventilation (also more preferred).

One administration method is administering to a subject an aerosol suspension of respirable particles comprising the active compound by inhalation. The respirable particles can be liquid or solid, with a particle size sufficiently small to pass through the mouth and larynx upon inhalation; in general, particles ranging from about 1 to 10 microns, but more preferably 1-5 microns, in size are considered respirable. The surface concentrations of active compounds delivered via inhalation can vary according to compounds; but are generally $1\times10^{-10}$-$1\times10^{-4}$ moles/liter, and preferably $1\times10^{-8}$-$1\times10^{-5}$ moles/liter.

It is understood, however, that the specific dose level for any particular patient will depend upon a variety of factors including the activity of the specific compound employed, the age, body weight, general health, sex, diet, time of administration, route of administration, and rate of excretion, drug combination (i.e., other drugs being administered to the patient), the severity of the particular disease undergoing therapy, and other factors, including the judgment of the prescribing medical practitioner.

Preferred compounds of the invention will have favorable pharmacological properties. Such properties include, but are not limited to bioavailability, low toxicity, low serum protein binding and desirable in vitro and in vivo half-life. Distribution in the body to sites of complement activity is also desirable, e.g., compounds used to treat CNS disorders will preferably penetrate the blood brain barrier, while low brain levels of compounds used to treat periphereal disorders are typically preferred.

An example of targeted drug delivery is enclosure of the compound within a liposome, where the liposome is coated with a specific antibody whose antigen is expressed in the targeted tissue. It can be advantageous to construe a controlled delivery system of the compounds since such an inhaled product targets the site of action, presents the compound of interest in small regimented quantities and reduces/minimizes any unwanted side effects.

Another example of a delivery system includes microparticulate compositions of the compound. In such a case, the compound is formulated as a microparticulate wherein the carrier is loaded with the compound; such a preparation is then filtered through a fine porous membrane or suitable filtering medium or is exposed to solvent interchanges to produce nanoparticles. Such preparations can be freeze dried or held in suspension in an aqueous or physiologically compatible medium. The preparation so obtained can be inhaled by suitable means.

Another example of a suitable preparation includes a reconstitutable preparation. In this case, the compound is formulated in a preparation to contain the necessary adjuvant to make it physiologically compatible. Such a preparation can be reconstituted by addition of water for injection or suitable physiological fluids, admixed by simple agitation and inhaled using appropriate techniques described above.

The compounds described above can also be prepared into dry powder or equivalent inhalation powders using the well known art of super critical fluid technology. In such a case, the compound is admixed with appropriate excipients and milled into a homogenous mass using suitable solvents or adjuvants. Following this, this mass is subjected to mixing using super critical fluid technology and suitable particle size distribution achieved. The particles in the formulation need to be of a desired particle size range such that the particles can be inhaled into the lungs using a suitable inhalation technique or introduced into the lungs via a mechanical ventilator. Alternatively, a formulation can be designed such that the particles are large enough in size thereby offering sufficient surface area to dissolve completely in a suitable fluid when admixed together or to dissolve sufficiently enough prior to nebulization into the lungs.

The invention is illustrated further by the following examples that are not to be construed as limiting the invention in scope to the specific procedures described in them.

EXAMPLES

Example 1

Rho Kinase Inhibition Assay

Relevance:

This assay demonstrates a compound's ability to inhibit ROCK2 and ROCK1 in an in vitro setting using the isolated enzyme. Compounds having ROCK2 $IC_{50}$ values on the order of 2 µM or below have been shown to possess efficacy in many studies using in vivo models of the disease processes described in this application.

Protocol

Inhibition of ROCK2 and ROCK1 activity was determined using the IMAP™ Screening Express Kit (Molecular Devices product number #8073). ROCK2 enzyme (Upstate/Chemicon #14-451), ROCK1 (Upstate/Chemicon #14-601) and Flourescein tagged substrate peptide Fl-AKRRRLSSLRA (Molecular Devices product number R7184) was pre-incubated with a test compound (a Formula II compound or other rho kinase compound such as fasudil, H-1152, H7, Y-27632, Y-39983) for 5 minutes in buffer containing 10 mM Tris-HCl pH 7.2, 10 mM $MgCl_2$, and 0.1% BSA. Following the pre-incubation, 10 µM ATP was added to initiate the reaction. After 60 minutes at room temperature, Molecular Devices IMAP™ binding solution was added to bind phosphorylated substrate. After 30 minutes of incubation in the presence of the IMAP™ beads, the fluorescence polarization was read and the ratio was reported as mP. $IC_{50}$ values for compounds and $EC_{50}$ values for ATP were calculated using the Prism software from Graphpad.

Results:

TABLE 1

Rho Kinase I and II Potency Data

| Compound | ROCK1 Ki, Avg, nM | ROCK1 Ki, StdDev, nM | ROCK2 Ki, Avg, nM | ROCK2 Ki, StdDev, nM |
|---|---|---|---|---|
| 1.008 | 30.5 | 0.8 | 3.9 | 0.1 |
| 1.034 | 36.0 | 22.2 | 5.3 | 2.6 |
| 1.039 | 208.6 | 109.0 | 24.7 | 8.4 |
| 1.051 | 37.2 | 4.0 | 3.8 | 0.0 |
| 1.072 | 33.7 | 22.1 | 5.6 | 3.1 |
| 1.074 | 40.1 | 3.3 | 4.1 | 1.5 |
| 1.075 | 48.7 | 2.8 | 4.4 | 0.3 |
| 1.076 | 14.3 | 5.4 | 2.6 | 0.6 |
| 1.077 | 76.1 | 30.9 | 11.1 | 5.8 |
| 1.078 | 36.3 | 10.1 | 3.6 | 0.9 |
| 1.079 | 71.5 | 9.1 | 4.7 | 1.1 |
| 1.080 | 130.8 | 42.6 | 15.2 | 4.4 |
| 1.087 | 84.1 | 11.1 | 15.4 | 1.4 |
| 1.090 | 281.0 | 103.7 | 24.9 | 7.9 |
| 1.091 | 71.4 | 22.0 | 3.3 | 1.0 |
| 1.092 | 190.5 | 42.2 | 28.4 | 10.6 |
| 1.093 | 64.5 | 21.9 | 7.7 | 5.2 |
| 1.095 | 274.8 | 88.0 | 49.5 | 35.9 |
| 1.098 | 205.6 | 69.4 | 25.0 | 6.4 |
| 1.106 | 223.4 | 82.0 | 15.1 | 4.9 |
| 1.107 | 233.7 | 137.2 | 14.0 | 8.5 |
| 1.108 | 25.6 | 3.2 | 6.5 | 0.3 |
| 1.109 | 58.8 | 25.8 | 9.6 | 2.5 |
| 1.110 | 59.0 | 4.1 | 11.2 | 0.3 |
| 1.115 | 89.7 | 17.5 | 20.6 | 1.7 |
| 1.116 | 257.8 | 45.6 | 48.9 | 5.5 |
| 1.117 | 208.0 | 1.9 | 35.8 | 2.3 |
| 1.118 | 461.7 | 28.3 | 81.7 | 52.7 |
| 1.123 | 82.3 | 11.0 | 9.6 | 4.3 |
| 1.124 | 64.5 | 7.9 | 3.3 | 0.8 |
| 1.125 | 557.1 | 1.7 | 50.9 | 16.8 |
| 1.126 | 76.2 | 16.7 | 17.2 | 3.9 |
| 1.127 | 96.6 | 11.6 | 11.2 | 0.4 |
| 1.130 | 577.1 | 340.0 | 142.0 | 38.1 |
| 1.131 | 19.7 | 5.9 | 3.8 | 0.9 |
| 1.132 | 22.5 | 6.5 | 3.5 | 0.4 |
| 1.133 | 25.0 | 7.2 | 4.3 | 1.1 |
| 1.134 | 22.4 | 6.0 | 4.4 | 0.6 |
| 1.136 | 40.3 | 15.3 | 5.4 | 0.4 |
| 1.137 | 25.8 | 10.7 | 5.1 | 1.2 |
| 1.138 | 36.3 | 12.2 | 7.2 | 1.1 |
| 1.139 | 200.3 | 26.3 | 23.2 | 9.6 |
| 1.140 | 236.1 | 199.3 | 32.9 | 24.9 |
| 1.141 | 28.5 | 11.1 | 3.8 | 1.1 |
| 1.142 | 104.2 | 26.6 | 12.0 | 4.4 |
| 1.143 | 49.7 | 30.8 | 12.6 | 11.9 |
| 1.144 | 97.6 | 65.0 | 19.5 | 13.0 |
| 1.145 | 35.0 | 13.5 | 6.4 | 0.9 |
| 1.146 | 39.8 | 10.9 | 10.7 | 1.5 |
| 1.147 | 58.3 | 15.6 | 45.7 | 52.0 |
| 1.148 | 24.3 | 13.7 | 3.6 | 0.9 |
| 1.149 | 46.8 | 21.3 | 4.2 | 2.2 |
| 1.150 | 33.2 | 17.5 | 3.2 | 1.2 |
| 1.151 | 22.8 | 6.0 | 2.9 | 0.5 |
| 1.152 | 19.8 | 13.3 | 3.3 | 0.9 |
| 1.153 | 62.8 | 8.7 | 4.2 | 0.8 |

TABLE 1-continued

Rho Kinase I and II Potency Data

| Compound | ROCK1 Ki, Avg, nM | ROCK1 Ki, StdDev, nM | ROCK2 Ki, Avg, nM | ROCK2 Ki, StdDev, nM |
|---|---|---|---|---|
| 1.154 | 52.7 | 9.5 | 6.6 | 1.0 |
| 1.155 | 45.4 | 14.7 | 7.0 | 2.0 |
| 1.156 | 135.8 | 34.3 | 13.0 | 3.0 |
| 1.157 | 263.8 | 73.9 | 8.8 | 1.6 |
| 1.158 | 64.1 | 20.1 | 5.1 | 1.0 |
| 1.159 | 48.1 | 9.2 | 10.1 | 2.6 |
| 1.160 | 218.3 | 28.3 | 49.4 | 13.4 |
| 1.161 | 9.9 | 3.4 | 2.5 | 0.5 |
| 1.162 | 15.2 | 1.5 | 2.8 | 0.8 |
| 1.163 | 33.6 | 5.8 | 2.9 | 0.4 |
| 1.164 | 42.4 | 7.2 | 6.1 | 1.2 |
| 1.165 | 50.7 | 4.4 | 3.4 | 0.6 |
| 1.166 | 95.2 | 8.6 | 8.0 | 0.8 |
| 1.167 | 118.6 | 17.1 | 18.5 | 1.7 |
| 1.168 | 162.2 | 68.3 | 22.9 | 10.4 |
| 1.169 | 256.2 | 132.7 | 33.8 | 20.0 |
| 1.170 | 80.0 | 25.9 | 12.5 | 6.1 |
| 1.171 | 109.2 | 60.1 | 16.0 | 8.4 |
| 1.172 | 103.0 | 40.6 | 20.5 | 7.3 |
| 1.173 | 15.1 | 6.8 | 3.6 | 1.0 |
| 1.175 | 65.9 | 28.3 | 7.6 | 1.5 |
| 1.176 | 314.3 | 77.6 | 11.2 | 3.2 |
| 1.177 | 156.1 | 55.0 | 18.2 | 5.5 |
| 1.178 | 137.6 | 58.0 | 24.9 | 17.6 |
| 1.179 | 292.0 | 70.7 | 19.3 | 4.4 |
| 1.180 | 138.5 | 46.5 | 23.1 | 4.8 |
| 1.181 | 567.8 | 191.3 | 32.8 | 3.5 |
| 1.182 | 408.3 | 106.6 | 30.6 | 4.3 |
| 1.183 | 165.1 | 46.3 | 16.8 | 3.7 |
| 1.184 | 843.1 | 53.0 | 90.9 | 13.9 |
| 1.185 | 81.6 | 33.0 | 12.6 | 6.4 |
| 1.186 | 129.3 | 42.2 | 11.9 | 4.9 |
| 1.187 | 296.2 | 78.8 | 17.3 | 5.8 |
| 1.188 | 3468.8 | | 652.7 | |
| 1.189 | 187.9 | 62.0 | 34.3 | 5.1 |
| 1.190 | 325.6 | 38.9 | 71.8 | 9.0 |
| 1.191 | 147.3 | 24.7 | 33.4 | 2.0 |
| 1.192 | 158.4 | 33.5 | 37.7 | 4.7 |
| 1.193 | 64.9 | 4.2 | 14.8 | 1.2 |
| 1.194 | 175.7 | 6.3 | 20.2 | 2.4 |
| 1.195 | 196.2 | 58.0 | 10.3 | 3.6 |
| 1.196 | 710.7 | 191.7 | 39.8 | 15.0 |
| 1.197 | 120.2 | 36.0 | 5.0 | 1.4 |
| 1.198 | 584.5 | 139.5 | 24.7 | 9.9 |
| 1.199 | 1856.6 | | 213.0 | 34.4 |
| 1.200 | 76.5 | 17.9 | 5.9 | 0.9 |
| 1.201 | 1585.4 | | 229.5 | |
| 1.202 | 203.5 | 40.9 | 33.0 | 2.1 |
| 1.203 | 329.4 | 67.4 | 41.6 | 6.4 |
| 1.204 | 196.1 | 42.0 | 31.9 | 2.2 |
| 1.205 | 498.1 | 95.2 | 46.4 | 3.7 |
| 1.206 | 64.4 | 15.1 | 9.1 | 3.8 |
| 1.207 | 516.3 | 27.5 | 43.7 | 1.1 |
| 1.208 | 54.2 | 25.0 | 12.9 | 2.8 |
| 1.209 | 4591.0 | | 469.6 | 58.3 |
| 1.210 | 95.1 | 18.2 | 25.5 | 3.8 |
| 1.211 | 395.5 | 58.5 | 57.6 | 0.6 |
| 1.212 | 44.2 | 11.2 | 3.9 | 0.2 |
| 1.213 | 106.3 | 10.9 | 3.0 | 0.5 |
| 1.214 | 546.5 | 10.9 | 143.0 | 7.0 |
| 1.215 | 102.8 | 5.8 | 3.5 | 0.3 |
| 1.216 | 1885.4 | | 402.9 | 79.5 |
| 1.217 | 70.1 | 9.5 | 12.1 | 1.1 |
| 1.218 | 401.8 | 34.4 | 30.7 | 3.0 |
| 1.219 | 343.6 | 37.6 | 15.4 | 2.3 |
| 1.221 | 264.4 | 41.6 | 30.0 | 2.6 |
| 1.222 | 228.8 | 41.9 | 75.5 | 1.2 |
| 1.223 | 239.5 | 21.5 | 15.7 | 1.9 |
| 1.224 | 487.0 | 151.5 | 77.5 | 23.0 |
| 1.225 | 605.0 | 133.2 | 189.4 | 48.9 |
| 1.226 | 91.7 | 31.5 | 8.8 | 2.6 |
| 1.227 | 47.5 | 2.8 | 5.3 | 0.4 |
| 1.228 | 1883.4 | 681.9 | 139.6 | 28.2 |
| 1.229 | 121.4 | 86.2 | 18.4 | 5.8 |
| 1.230 | 345.9 | 85.2 | 35.3 | 9.8 |
| 1.231 | 305.1 | 62.8 | 60.3 | 18.2 |
| 1.232 | 136.6 | 41.1 | 20.8 | 8.8 |
| 1.233 | 47.2 | 7.2 | 1.3 | 0.1 |
| 1.234 | 1735.2 | 179.0 | 166.4 | 11.6 |
| 1.235 | 1386.4 | 173.1 | 335.4 | 29.4 |
| 1.236 | 49.3 | 7.1 | 2.1 | 0.1 |
| 1.237 | 286.7 | 55.0 | 4.0 | 0.4 |
| 1.238 | 61.2 | 22.1 | 1.5 | 0.3 |
| 1.239 | 282.6 | 36.2 | 6.3 | 0.6 |
| 1.240 | 624.8 | 74.2 | 60.1 | 9.3 |
| 1.241 | 65.1 | 11.8 | 21.0 | 6.4 |
| 1.242 | 71.4 | 14.1 | 17.5 | 1.8 |
| 1.243 | 219.3 | 29.7 | 84.3 | 17.2 |
| 1.244 | 683.1 | 80.9 | 138.7 | 25.4 |
| 1.245 | 199.0 | 27.7 | 49.5 | 7.9 |
| 1.246 | 92.1 | 6.3 | 11.2 | 0.8 |
| 1.247 | 1312.4 | 268.7 | 242.6 | 53.1 |
| 1.248 | 2349.7 | | 890.6 | 509.8 |
| 1.249 | 91.7 | 25.0 | 8.6 | 3.8 |
| 1.250 | 247.0 | 63.7 | 45.8 | 13.8 |
| 1.251 | 206.8 | 44.0 | 49.2 | 10.5 |
| 1.252 | 30.5 | 1.5 | 4.5 | 0.4 |
| 1.253 | 59.9 | 7.4 | 1.7 | 0.2 |
| 1.254 | 116.0 | 19.4 | 39.0 | 8.7 |
| 1.255 | 3559.3 | 1202.9 | 358.9 | 99.3 |
| 1.256 | 700.1 | 179.5 | 85.5 | 18.8 |
| 1.257 | 1273.7 | 237.3 | 168.0 | 35.4 |
| 1.258 | 9.5 | 3.5 | 1.3 | 0.4 |
| 1.259 | 19.5 | 11.6 | 2.1 | 0.3 |
| 1.260 | 70.9 | 48.0 | 7.1 | 1.9 |
| 1.261 | 307.4 | 139.0 | 14.8 | 6.5 |
| 1.262 | 54.9 | 13.3 | 4.0 | 0.7 |
| 1.263 | 2130.5 | 673.5 | 453.4 | 105.3 |
| 1.264 | 494.5 | 1.1 | 59.4 | 9.5 |
| 1.265 | 161.7 | 25.9 | 21.6 | 0.8 |
| 1.266 | 53.8 | 15.1 | 17.1 | 2.8 |
| 1.267 | 98.8 | 21.6 | 23.9 | 6.2 |
| 1.268 | 403.6 | 78.8 | 40.7 | 7.5 |
| 1.269 | 239.1 | 62.6 | 22.8 | 9.0 |
| 1.270 | 130.5 | 45.0 | 9.9 | 0.6 |
| 1.271 | 332.1 | 99.9 | 77.7 | 5.8 |
| 1.272 | 1823.7 | 1294.6 | 194.3 | 17.0 |
| 1.273 | 31.3 | 8.3 | 8.2 | 1.0 |
| 1.274 | 223.4 | 46.3 | 10.7 | 1.1 |
| 1.275 | 401.7 | 44.9 | 14.1 | 2.0 |
| 1.276 | 64.2 | 5.2 | 12.3 | 2.5 |
| 1.277 | 42.3 | 10.4 | 4.6 | 1.3 |
| 1.278 | 80.2 | 10.5 | 10.2 | 1.8 |
| 1.279 | 455.9 | 20.3 | 34.2 | 1.6 |
| 1.280 | 746.0 | 58.3 | 38.0 | 4.0 |
| 1.281 | 71.8 | | 7.4 | |
| 2.007 | 390.4 | | 179.1 | |
| 2.016 | 100.5 | 14.8 | 42.4 | 10.2 |
| 2.020 | 100.5 | 13.1 | 36.5 | 4.7 |
| 2.022 | 44.8 | 6.9 | 15.3 | 1.1 |
| 2.025 | 6.9 | 1.3 | 2.9 | 0.5 |
| 2.026 | 38.0 | 15.2 | 13.0 | 4.1 |
| 2.027 | 15.7 | 3.8 | 7.4 | 2.3 |
| 2.031 | 14.6 | 4.9 | 5.3 | 1.2 |
| 2.034 | 1002.6 | 392.4 | 221.1 | 312.7 |
| 2.035 | 601.0 | | 201.9 | |
| 2.036 | 579.5 | 139.9 | 232.8 | |
| 2.037 | 920.8 | | 182.2 | |
| 2.038 | 28.9 | 4.5 | 6.3 | 1.0 |
| 2.039 | 18.8 | 9.6 | 6.7 | 1.9 |
| 2.040 | 59.6 | 10.7 | 25.4 | 5.0 |
| 2.041 | 30.8 | 2.6 | 9.6 | 2.6 |
| 2.043 | 49.4 | 9.5 | 21.5 | 2.4 |
| 2.044 | 81.4 | 20.2 | 24.1 | 3.7 |
| 2.045 | 90.6 | 64.6 | 88.0 | 57.3 |
| 2.046 | 16.7 | 1.1 | 5.6 | 0.8 |
| 2.047 | 26.4 | 3.6 | 7.0 | 2.3 |
| 2.048 | 71.5 | 22.8 | 34.6 | 9.7 |
| 2.049 | 113.0 | 42.1 | 48.0 | 17.1 |
| 2.050 | 367.7 | 115.4 | 250.7 | |

TABLE 1-continued

Rho Kinase I and II Potency Data

| Compound | ROCK1 Ki, Avg, nM | ROCK1 Ki, StdDev, nM | ROCK2 Ki, Avg, nM | ROCK2 Ki, StdDev, nM |
|---|---|---|---|---|
| 2.051 | 1437.2 | 595.4 | 1179.8 | |
| 2.052 | 508.5 | 169.1 | 142.6 | |
| 2.053 | 951.6 | 157.1 | 182.4 | |
| 2.054 | 17.1 | 2.3 | 3.7 | 0.1 |
| 2.055 | 16.0 | 5.3 | 6.4 | 1.2 |
| 2.056 | 106.6 | 12.7 | 48.7 | 26.5 |
| 2.057 | 6.2 | 1.3 | 3.7 | 0.7 |
| 2.058 | 15.3 | 2.8 | 3.3 | 0.6 |
| 2.059 | 3.9 | 0.3 | 2.7 | 0.2 |
| 2.060 | 4.9 | 0.3 | 3.2 | 0.1 |
| 2.061 | 10.5 | 3.2 | 1.8 | 0.4 |
| 2.062 | 63.4 | 25.1 | 30.5 | 2.2 |
| 2.063 | 206.2 | 88.8 | 73.9 | 3.5 |
| 2.064 | 4.1 | 1.8 | 2.2 | 0.4 |
| 2.065 | 4.1 | 1.4 | 1.8 | 0.2 |
| 2.066 | 10.2 | 3.4 | 2.3 | 0.4 |
| 2.067 | 19.6 | 5.8 | 4.2 | 0.5 |
| 2.068 | 8.0 | 2.0 | 5.8 | 0.4 |
| 2.069 | 16.7 | 4.9 | 2.4 | 0.3 |
| 2.070 | 285.9 | 122.0 | 48.4 | 6.1 |
| 2.071 | 21.2 | 2.7 | 11.9 | 0.5 |
| 2.072 | 7.5 | 1.4 | 4.4 | 0.5 |
| 2.073 | 12.7 | 2.6 | 4.2 | 0.4 |
| 2.074 | 133.3 | 31.1 | 36.4 | 7.7 |
| 2.075 | 123.0 | 25.7 | 21.7 | 1.5 |
| 2.076 | 8.0 | 1.8 | 2.4 | 0.3 |
| 2.077 | 33.7 | 12.5 | 5.0 | 0.8 |
| 2.078 | 18.3 | 4.4 | 2.6 | 0.0 |
| 2.079 | 18.5 | 5.5 | 2.3 | 0.2 |
| 2.080 | 213.7 | 18.5 | 125.9 | 17.7 |
| 2.081 | 1446.1 | 317.4 | 1111.2 | 989.8 |
| 2.082 | 131.7 | 30.1 | 9.0 | 2.9 |
| 2.083 | 1882.9 | 380.5 | 857.6 | 706.9 |
| 2.084 | 1174.6 | 172.9 | 349.6 | 116.2 |
| 2.085 | 2391.7 | 219.6 | 812.0 | 417.7 |
| 2.086 | 1246.0 | 57.7 | 358.0 | 28.5 |
| 2.087 | 896.4 | 67.0 | 59.3 | 6.2 |
| 2.088 | 38.7 | 6.1 | 13.6 | 1.6 |
| 2.089 | 102.1 | 3.7 | 32.9 | 3.1 |
| 2.090 | 53.3 | 10.2 | 19.5 | 2.4 |
| 2.091 | 776.1 | 94.2 | 236.7 | 16.1 |
| 2.092 | 1132.5 | 128.2 | 458.0 | 73.1 |
| 2.093 | 576.3 | 99.5 | 127.7 | 19.5 |
| 2.094 | 16570.6 | 1465.6 | | |
| 2.096 | 70.2 | 9.7 | 9.6 | 1.5 |
| 2.097 | 35.4 | 2.1 | 2.8 | 0.8 |
| 2.098 | 382.5 | 13.6 | 73.5 | 3.6 |
| 2.099 | 15.0 | | 3.8 | |
| fasudil | 346.3 | 17.6 | 96.4 | 6.4 |
| H-1152 | 18.5 | 5.3 | 2.0 | 0.3 |
| H7 | | | 124.7 | 5.6 |
| Y-27632 | 197.2 | 50.6 | 60.9 | 16.9 |
| Y-39983 | 34.7 | 11.1 | 3.6 | 0.9 |

Conclusion

Most of the compounds studied inhibited ROCK2 with a $K_i$ below 600 nM, many of these values below 60 nM. The most potent compounds in this assay showed $K_i$ values below 15 nM.

Example 2

NIH/3T3 Cell Morphology Assay

Relevance

The assay demonstrates that a compound's in vitro ROCK inhibition activity manifests itself in morphology changes, such as actin stress fiber disassembly and alteration in focal adhesions in intact cells leading to inhibition of acto-myosin driven cellular contraction. These morphology changes provide the basis for the beneficial pharmacological effects sought in the setting of the disease processes described in this application, specifically the disruption of the actin stress fibers and its impact on cell mobility (Howard et. at. *The J. of Cell Biology* 98:1265-1271, 1984); and endothelial and epithelial permeability (Stephens et al., *Am. Rev. Respir. Dis,* 137:4220-5, 1988 and Vandenbroucke et al., *Ann. N.Y. Acad. Sci.* 1123: 134-145, 2008.)

Protocol

NIH/3T3 cells were grown in DMEM-H containing glutamine and 10% Colorado Calf Serum. Cells were passaged regularly prior to reaching confluence. Eighteen to 24 hours prior to experimentation, the cells were plated onto Poly-L-Lysine-coated glass bottom 24-well plates. On the day of experimentation, the cell culture medium was removed and was replaced with the same medium containing from 10 nM to 25 µM of the test compound, and the cells were incubated for 60 minutes at 37° C. The culture medium was then removed and the cells were washed with warmed PBS and fixed for 10 minutes with warmed 4% paraformaldehyde. The cells were permeabilized with 0.5% Triton-X, stained with TRITC-conjugated phalloidin and imaged using a Nikon Eclipse E600 epifluorescent microscope to determine the degree of actin disruption. Results were expressed as a numerical score indicating the observed degree of disruption of the actin cytoskeleton at the test concentration, ranging from 0 (no effect) to 4 (complete disruption), and were the average of at least 2 determinations.

All compounds tested show measurable activity in the cell morphology assay, with most of the compounds providing substantial effects (score of ≧2 at 1 µM) on the actin cytoskeleton at the testing concentration (see Table 2).

TABLE 2

Cell Morphology Assay Data

| Compound | Cell score at 1 µM |
|---|---|
| 1.002 | 1.4 |
| 1.004 | 1.8 |
| 1.005 | 1.3 |
| 1.006 | 2 |
| 1.008 | 2 |
| 1.024 | 2.4 |
| 1.025 | 2 |
| 1.034 | 2 |
| 1.039 | 2 |
| 1.041 | 2.5 |
| 1.046 | 2.5 |
| 1.048 | 1.5 |
| 1.051 | 2.5 |
| 1.052 | 2.8 |
| 1.062 | 2.3 |
| 1.066 | 2 |
| 2.002 | 1.8 |
| 2.006 | 2.8 |
| 2.008 | 1 |
| 2.016 | 1.8 |
| 2.017 | 2 |
| 2.018 | 1.8 |
| 2.026 | 2 |

Example 3

Cytokine Secretion Assay

Cytokine secretion plays a major role in a number of inflammatory diseases. In the presence of increased cytokine levels, certain tissues show an up-regulation of adhesion molecules, increased vascular permeability, and increased extravasation of leukocytes including neutrophils, macrophages, and lymphocytes. In this assay, lipopolysaccharide (LPS) was used as the inflammatory stimulus to induce cytokine production in human monocytes, and ATP was used to stimulate release of the pro-inflammatory cytokine IL-1β.

Peripheral blood from healthy human volunteers was collected and the monocytes isolated via Ficoll-paque density centrifugation. The resultant pellet was re-suspended in media containing 1 ng/mL lipopolysaccharide (LPS) and plated at a density of 500,000 cells/mL. After 3 hours of incubation (37° C., 5% $CO_2$, humidified air), monocytes were selected by adherence to the tissue culture plastic by washing wells with media. Following the media wash, cells were incubated for 2 minutes with the Rho kinase inhibitors (10 µM) prior to the addition of 1 mM ATP. Cells were allowed to incubate with compounds for 30 minutes at 37° C. after which the supernatant was removed for immediate determination of IL-1β concentration. The concentration of IL-1β in cell supernatants was measured using the Human IL-1β kit and Bio-Plex system (Bio-Rad) according to manufacture's instructions.

FIG. 1 shows percent inhibition of IL-1β secretion in human monocytes by Rho kinase inhibitors. The tested Rho kinase inhibitors of Formula I or II at a 10 µM concentration demonstrated a varying efficacy range. Many compounds effectively reduced IL-1β secretion to low level.

Example 4

Cellular Proliferation Assay

Cellular proliferation is an important process in tumorigenesis and in remodeling effects. This assay measures the ability of compounds of this invention to regulate proliferation.

Figure 2:
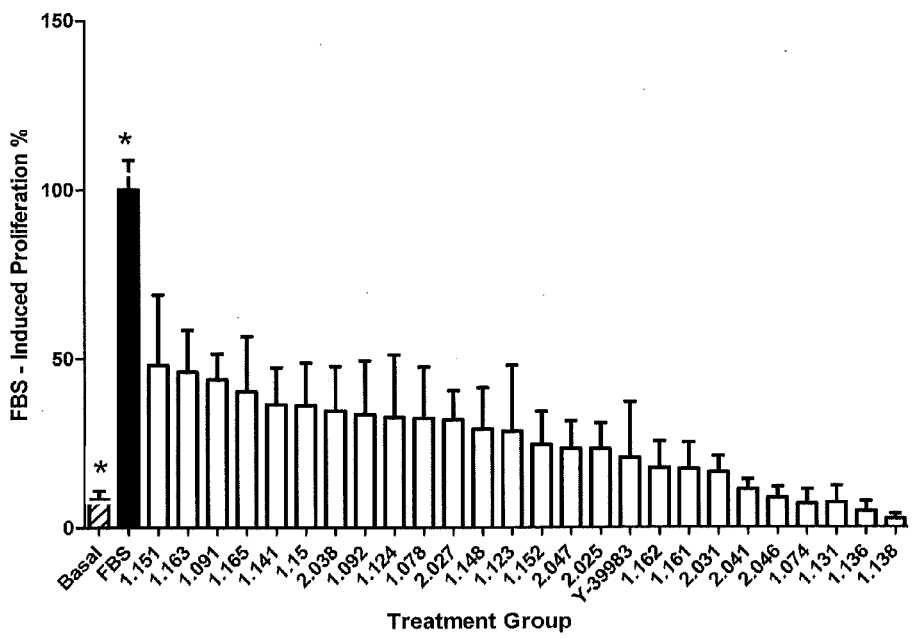
FIG. 2 shows percent of FBS induced proliferation. Each compound was tested at 30 uM and challenged with 10% FBS with an n=3. * indicates n=5.

Effects on cell proliferation were measured using a radiographic technique know as [$^3$H] thymidine incorporation. A-10 rat thoracic aorta cells (ATCC #CRL 1476) were grown on 24-well plates in Dulbecco's Modified Eagles Medium-High Glucose (Gibco cat. # 11995-065) containing 10% Fetal Bovine Serum (Sigma EC# 232-690-6) for 24 hrs in an incubator at 37° C. Growth media was then removed, the cells were washed with warmed PBS (Gibco cat# 14190-144) and warmed serum free media containing 0.1% BSA in order to force the cells into a quiescent state. 24 hours later the media was removed and replaced with warmed serum free media containing from 10 nM to 30 uM of test compound. The cells were incubated for 60 min at 37° C. The cells were then stimulated with either 10% FBS or 10 ng/mL PDGF (BD Biosciences cat# 354051) and placed in an incubator at 37° C. for 18 hrs. [$^3$H] thymidine (Perkin Elmer NET027A001MC) was then added to the cells at a final concentration of 3 uCi/mL and placed in an incubator at 37° C. for 24 hrs. The media was removed and the cells were washed with warmed PBS twice. 500 uL of warmed trypsin (Gibco cat# 25300-054) was added to each well and they were place in an incubator at 37° C. for 15 min. To precipitate the DNA, 500 uL of ice cold 20% TCA (MP Biomedicals cat# 152592) was added to each well. The resulting suspension was filtered using a vacuum manifold and glass fiber filters (Whatman cat# 1827-025). The fiber filters were then counted using a liquid scintillation counter (Wallac 1409). Results were normalized to the total signal of the challenge, graphed using Graphpad Prism (Ver. 5.00) and reported as % challenge stimulated proliferation. The results are shown in FIG. 2. The results demonstrate that the tested Rho kinase inhibitors of Formula I or II compounds reduced cell proliferation in vitro. The majority of the tested compounds decreased the proliferation to less than 50% of the normal rate at a concentration of 30 uM.

Example 5

Animal Model for Treating Diabetic Nephropathy

Animal studies are conducted according to the methods of Kolavennu, et al., Diabetes 57:714-723 (2008). db/db diabetic mice are administered Rho kinase inhibitor compound of Formula I or II via intraperitoneal injection every day at the dose of 1-100 mg/kg of body weight starting at 8 weeks of age. A control group receives intraperitoneal vehicle administration. After 16 weeks of treatment (24 weeks age), the mice are housed in individual metabolic cages for collection of urine. Blood glucose is measured after a 12-h fast. Urinary albumin, collagen IV, serum and urine creatinine are measured using standard commercially available techniques as described previously (Kolavennu, et al., Diabetes 57:714-723 (2008)). Animals are then sacrificed for subsequent morphometric studies.

Morphometric studies. The kidneys are fixed in 10% neutral buffered formalin and subsequently embedded in paraffin. The 4-µm sections of paraffin-embedded tissues are stained with periodic acid-Schiff (PAS). Light microscopic views of 40 consecutive glomerular cross-sections per mouse are scanned into a computer. Glomerular and mesangial matrix areas are quantified in a blinded fashion using an image analysis system. Mesangial matrix index (MMI) is calculated as the ratio of mesangial area to glomerular area× 100 (% area).

Immunohistochemistry. Immunoperoxidase staining is carried out on 4-µm paraffin-embedded kidney tissue sections. The sections are preincubated in boiling sodium citrate buffer (10 mmol/l sodium citrate, 0.05% Tween 20, pH 6.0) for antigen retrieval. Specific primary antibodies, anti-fibronectin antibody and anti-collagen IV antibody are incubated with the sections overnight.

Transmission electron microscopy. Small pieces of kidney cortex are fixed in 2.5% glutaraldehyde in 0.2 mol/l cacodylate buffer (pH 7.4). They are then dehydrated through graded ethanol and propylene oxide, embedded in epoxy resin, and polymerized at 60° C. overnight by standard procedures. Ultrathin sections are stained with uranyl acetate and lead citrate. The specimens are observed using a transmission electron microscope. For each specimen, images of the glomerular basement membrane in 10 consecutive glomeruli are captured onto a computer.

Results

Treatment of diabetic animals for 16 weeks with Rho kinase inhibitor compound of Formula I or II results in improvement in at least one of the following outcome measures as compared to vehicle control indicating overall benefit of compound in the treatment of diabetic nephropathy: (1) decreased albuminuria; (2) decreased mesangial expansion as measured by MMI; (3) decreased accumulation of glomerular type IV collagen; (4) reduced glomerular basement membrane thickening.

Example 6

*P. falcipirum* Induced Apoptosis Assay

In order to determine the effect of Rho kinase inhibitors on *P. falcipirum* induced endothelial cell apoptosis, primary endothelial cells (HLEC) are isolated from human lung and cultured as described. *Plasmodium falciparum* cultures are used to infect human red blood cells (pRBC) as described (Taoufiq Z et al. *J. Infectious Diseases*, 197:1062-1073, 2008). Human lung endothelial cells (HLECs) are cultured in 6-well plates and exposed for 24 h to a suspension of mature forms of parasitized red blood cells (pRBCs) or to control RBCs with or without a Rho kinase inhibitor compound of Formula I or II (1 to 100 μM). Therefore four test groups are examined: HLEC incubated with RBC+/−Rho kinase inhibitor compound of Formula I or II and HLEC incubated with pRBC+/−Rho kinase inhibitor compound of Formula I or II. APOPercentage™ is used as a mean to quantify induced apoptosis and the effect of compounds on cell survival during pRBC/HLEC co-incubations by quantitatively assessing the release of purple red dye by apoptotic HLEC using Analytical Digital Photomicroscopy (ADP).

Example 7

*P. Falcipirum* Induced Endothelial Permeability Assay

In order to measure the effect of pRBC exposure on endothelial cell permeability, a method based on Evans Blue diffusion through the endothelial monolayer is used. Briefly HLEC are raised on Transwell Permeable supports until confluence in growth medium, Endothelial monolayers are exposed to pRBC for 4 hours. Monolayers are then treated for 20 hours with 1 to 100 μM of Rho kinase inhibitor compound of Formula I or II. Similar incubations with non infected erythrocytes is used as a control. Transwell compartments are then washed 3 times with RPMI-based adhesion medium. Transwell inserts are transferred to a new plate filled with PBS; a solution of Evans Blue dye at is then added in the upper compartments and incubated for 5 minutes at 37° C. and 5% $CO_2$. Lower compartment liquids are collected for optical density analysis at 630 nm of diffused Evans Blue using a standard microtiter plate reader.

Example 8

*P. falcipirum* Induced Endothelial Activation Assay

To test if Rho-kinase inhibitors have an effect on *P. falciparum* induced endothelial activation, HLECs are cultured in tissue culture plates and exposed to pRBC for 6 hours. Rho kinase inhibitor compound of Formula I or II is added at a concentration of 1 to 100 μM concomitantly with pRBC. Vehicle treated cells are used as a control. TNFα at 20 ng/ml is used as a positive control of NF-kappaB nuclear translocation stimulation. Cells are then fixed and permeabilized for immunostaining with primary anti-NF-kappaB P65 subunit antibody and secondary FITC-anti-mouse IgG antibody. Nuclei are stained with diamidino-phenylindole. After immunostaining of the NF-kappaB P65 subunit, results are analyzed by fluorescence microscopy and the number of activated HLEC (cells with complete but not partial migration nuclear P65 staining) per each condition is counted.

Results

The effects of compounds on apoptosis, endothelial permeability or activation of NF-kappaB nuclear translocation are measured and compared to control treated HLEC. Improvement in at least one of the above-mentioned endpoints is observed.

Example 9

Effect of Compounds on an In Vivo Lung Metastasis Model

Metastatic invasion of vital organs is a key pathology of cancer that contributes to mortality. In this model, metastatic invasion of the lung by the human fibrosarcoma cell line HT1080 is determined. The lung metastasis model is based on the methods of Ying H et al. *Mol Cancer Ther*, 5:2158-2164, 2006. HT1080 cells are injected into the tail vein of nude mice on day 0 to seed cancer cells to the lung. The mice are implanted s.c. with mini pumps containing either 10× saline or Rho kinase inhibitor compound of Formula I or II to deliver 1 to 100 mg/kg/d (day 0-21). Twenty-one days after cell inoculation, the mice are euthanized and the lungs are fixed by injecting formalin into the tracheas followed by soaking with Bouin's solution. The nodules are macroscopically counted and the presence of tumor cells in the nodules is confirmed microscopically.

Example 10

Effect of Compounds on an in vivo Breast Cancer Model

MDA-MB-231 cells are a breast cancer cell line widely used to study tumor growth. Injection of these cells into athymic mice results in the formation of tumors and serves as an in vivo model of breast cancer. The model is based on the methods of Ying H et al. *Mol Cancer Ther*, 5:2158-2164, 2006. For the orthotopic model with MDA-MB-231 cells, athymic mice are placed under isoflurane anesthesia and 40 μL of 2×10$^6$ MDA-MB-231 cells mixed 1:1 with Matrigel are injected into the left inguinal mammary fat pad on day 0. Tumor volume (mm$^3$) is estimated by caliper measurement in two perpendicular directions and calculated using the formula: (shortest diameter)$^2$×(longest diameter)×0.5. Immediately after cell implantation, the oral gavage treatments begin. The control group receives water in the bottle and water by gavage twice daily (day 0-57). The "gavage-only" group receives Rho kinase inhibitor compound of Formula I or II by gavage (1 to 100 mg/kg) twice a day from day 0 to 57. The "dual administration" group receives compound of Formula I or II in the drinking water (1 to 100 mg/mL) from day 6 to 57 and by gavage (1 to 100 mg/kg) once a day from day 0 to 57. Tumors become palpable several weeks after cell implantation. On day 57, all mice are euthanized and the tumors are counted, excised and weighed.

Example 11

Effect of Compounds on an In Vivo Invasive Assay

This in vivo animal test assesses tumor cell adhesion, migration through the mesothelial layer and growth under the mesothelium. Tumor cell dissemination similar to this model is frequently seen in patients suffering ovarian or gastric cancer with a fatal outcome. This assay is based on the methods of Itoh K et al. *Nature Medicine*, 5:221-5, 1999. Rat MM1 hepatoma cells (2×10$^7$) stably expressing Val$^{14}$-RhoA or Δ4ROCK are injected into the peritoneal cavities of rats. Rho kinase inhibitor compound of Formula I or II (~1 to 100 mg in 200 μL per pump per day) is continuously delivered with the use of two osmotic pumps implanted into the peritoneal cavity. After 11 days (for a total dose of 0.022 to 2.2 g), the animals are euthanized and the incidence of ascites, tumor nodules and tumor cell dissemination are assessed by gross observation.

Results

In the lung metastasis model, the number of tumor nodules found in the lung is determined. In the breast cancer model, tumor number and size is determined. In the in vivo invasive assay, ascites levels, tumor nodules and tumor cell dissemination are assessed. At least one of the following improvements is observed in the groups treated with Rho kinase inhibitor compound of Formula I or II: (1) a decrease in the number of tumor nodules in the lung; (2) attenuation of tumor number or size; or (3) attenuation of ascites levels, tumor nodules or tumor cell dissemination.

Example 12

In Vivo Anti-inflammatory Activity

Relevance

The mouse ovalbumin sensitization model has been developed by investigators to study malfunctioning of the immune system, cellular infiltration composed primarily of eosinophils and neutrophils, acute and chronic inflammation, and fluid accumulation (edema), especially in asthma. Although this model is mostly utilized in the context of asthma, this model is utilized to demonstrate the general in vivo anti-inflammatory properties of Compounds of Formula I or II.

Protocol

Male BALB/c mice were ordered from Charles River Laboratories (Raleigh, N.C.). The animals were approximately 19 to 21 grams at time of receipt. Upon arrival, the animals were randomized into groups of five males per cage and assigned to a dosing group. Animals were quarantined for 7 days under test conditions. They were observed daily for general health status and ability to adapt to the water bottles. Animals were sensitized on day 0 and 14 of study by an intraperitoneal injection with 20 µg of ovalbumin (ova) and 2.0 mg aluminum hydroxide (alum) which initiates the development of a specific T-helper (Th) cells type 2 resulting in asthmatic animals (denoted as Ova in the figures). One group of animals received an injection of saline to use as control animals (denoted as normal in the figures). All animals were challenged with aerosolized 1% ova once daily for 25 minutes on days 28, 29, and 30 (Zosky, et al. *Respiratory Research*, 2004; 5:15). Aerosol challenge consists of using an Aerogen Aeroneb nebulizer and controller with a particle size of 4-6 µm mass median aerodynamic diameter (MMAD) with a distribution of 400 µl per minute. This aerosol challenge is necessary to target the Th2-driven allergic inflammation in the lower airways.

Figure 3:
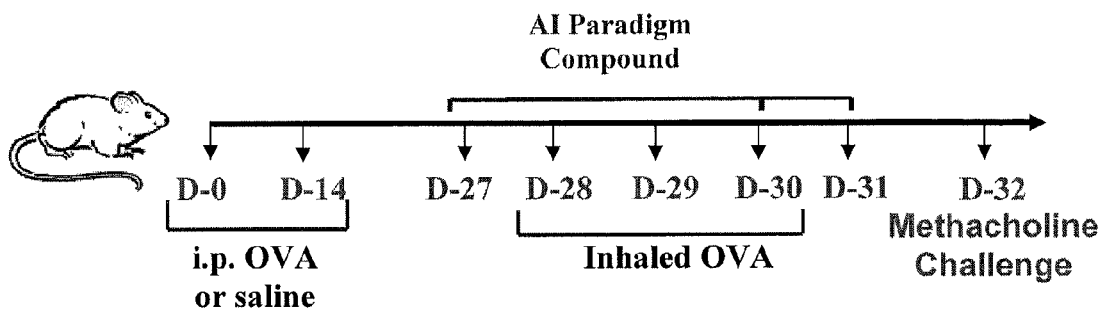
FIG. 3 shows the anti-inflammatory dosing paradigm.

The anti-inflammatory dosing paradigm (FIG. 3) was utilized to evaluate the anti-inflammatory effects of experimental compounds. The anti-inflammatory dosing paradigm consists of dosing the animals once a day starting on day 27 and finishing on either day 30 or 31 (1 hr prior to the aerosolized ovalbumin challenges on days 28 to 30) but not on day 32 when hyperreactivity evaluation occurs (described in Example 13). On day 32 of the experiment, after measurement of airway hyperreactivity, BALF was collected and all animals were anesthetized, bled and euthanized.

Bronchoalveolar lavage fluid (BALF) was collected by infusing 3.0 ml of saline with 10% fetal calf serum into the lungs via the trachea and then withdrawing the fluid. The total amount of cells/ml of BALF fluid was determined via manual cell count on hemocytometer. The BALF was centrifuged, supernatant removed and analyzed for cytokine concentrations as described below, and cell pellet reconstituted in 500 µL of fluid. Cytospin slides were prepared from the cell pellet using 100 µL of fluid and spinning samples for 5 minutes at 5000 rpms in a cytospin centrifuge. Following Hema3 stain, relative percentages of individual leukocytes were determined on a 200 cell count for each sample. The final concentration of individual leukocyte cell types per ml of BALF was determined by multiplication of the relative percentage of individual leukocytes with the total amount of cells/ml of BALF fluid.

Figure 4:
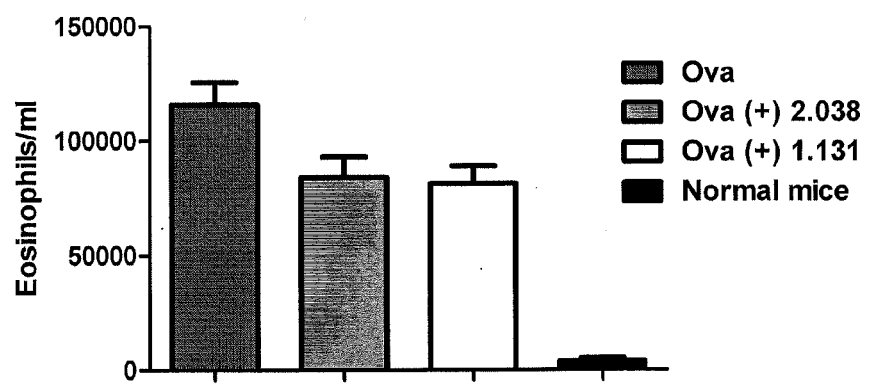
FIG. 4 shows the eosinophils per mL in ova-sensitized/ova-challenged mice, mice treated with Compound 2.038, mice treated with Compound 1.131 and normal mice.
Figure 5:
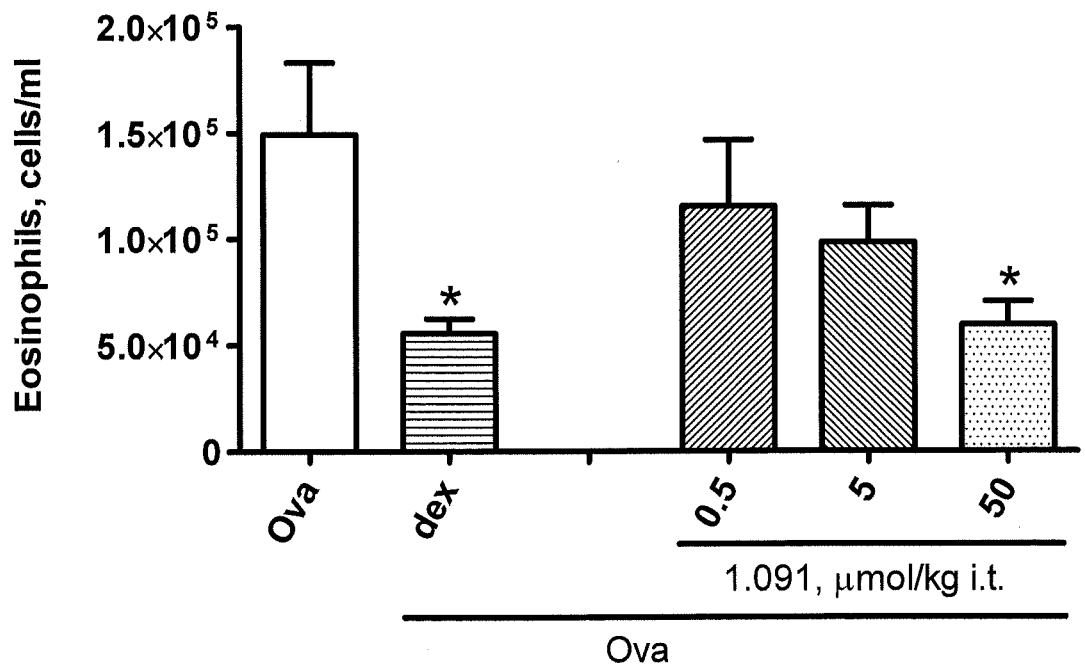
FIG. 5 shows the dose response effect of Compound 1.091 on eosinophil influx when dosed to ova-sensitized, ova-challenged mice, *, p<0.05 when compared to ova-sensitized, ova-challenged mice using Student's t-test.

Evaluation of the differential counts performed on these samples showed an increased number of inflammatory cells in the ova-sensitized, ova-challenged animals. FIG. 4 shows the eosinophils per ml of BALF in ova-sensitized, ova-challenged mice, mice treated with Compound 2.038, mice treated with Compound 1.131 and normal mice. Compounds were dosed orally to day 31 according to the anti-inflammatory dosing paradigm shown in FIG. 3. Airway eosinophil infiltration was reduced in animals treated with the two tested compounds (FIG. 4). As shown in FIG. 5, Compound 1.091 generates a reduction of eosinophils when dosed i.t. to day 30 according to the anti-inflammatory dosing paradigm shown in FIG. 3.

The concentrations of cytokines in the BALF samples were determined using commercially available Bio-plex kits (Bio-Rad) for the detection of mouse IL-5, IL-13, and Eotaxin. The analysis of cytokine levels was measured using the Bio-Plex 200 (Bio-Rad) system according to the manufacturer's instructions. Substantial evidence suggests that cytokines play an important role in orchestrating and regulating inflammatory processes through the involvement of T-helper type 2 lymphocytes.

Figure 6:
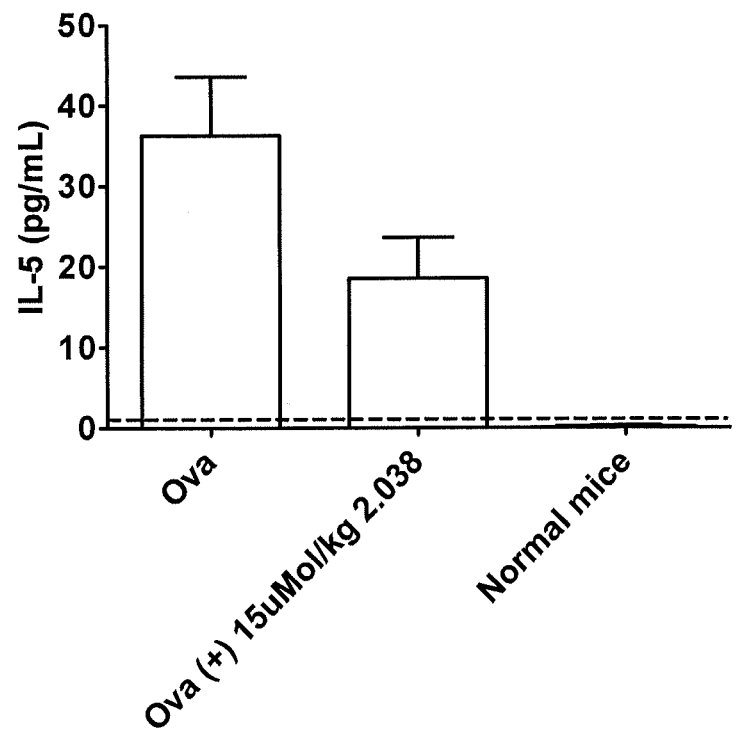
FIG. 6 shows the concentration of IL-5 (pg/mL) in BALF of (1) ova-sensitized, ova-challenged mice, (2) ova-sensitized, ova-challenged mice treated with Compound 2.038 (15 μmol/kg/oral), and (3) normal, saline-sensitized mice. Dashed line indicates the lower limit of detection for the cytokine of interest. Data represent mean±SEM, n=10 for ova-sensitized, ova-challenged mice, treated or untreated; n=5 for normal mice.
Figure 7:
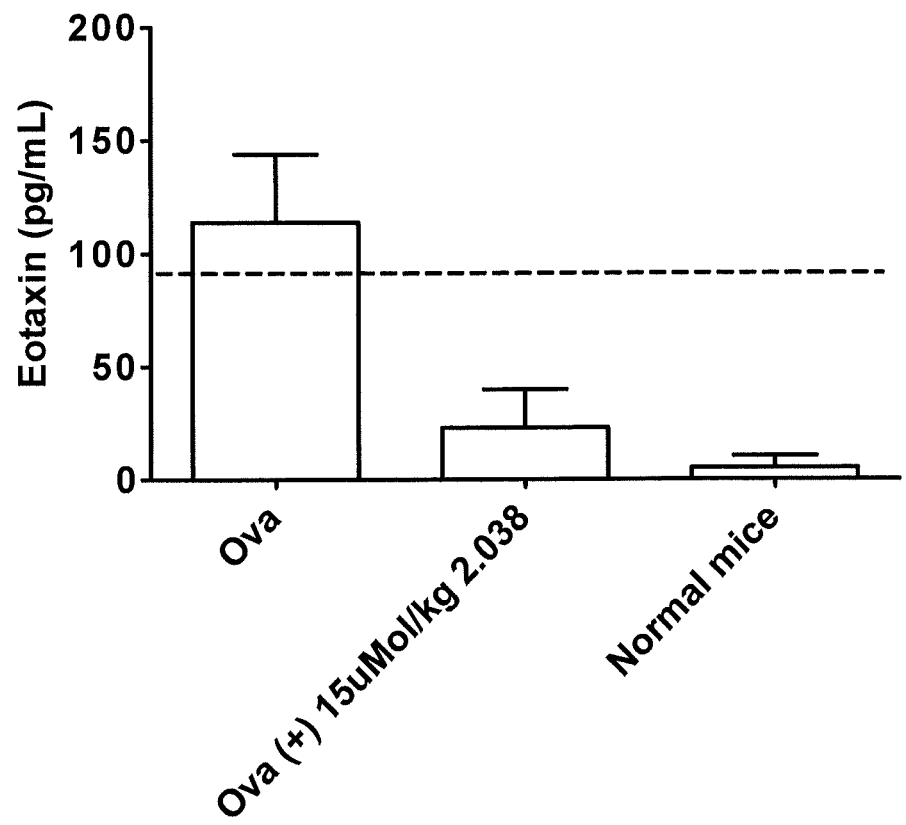
FIG. 7 shows the concentration of Eotaxin (pg/mL) in BALF of (1) ova-sensitized, ova-challenged mice, (2) ova-sensitized, ova-challenged mice treated with Compound 2.038 (15 μmol/kg/oral), and (3) normal, saline-sensitized mice. Dashed line indicates the lower limit of detection for the cytokine of interest. Data represent mean±SEM, n=10 for ova-sensitized, ova-challenged mice, treated or untreated; n=5 for normal mice.
Figure 8:
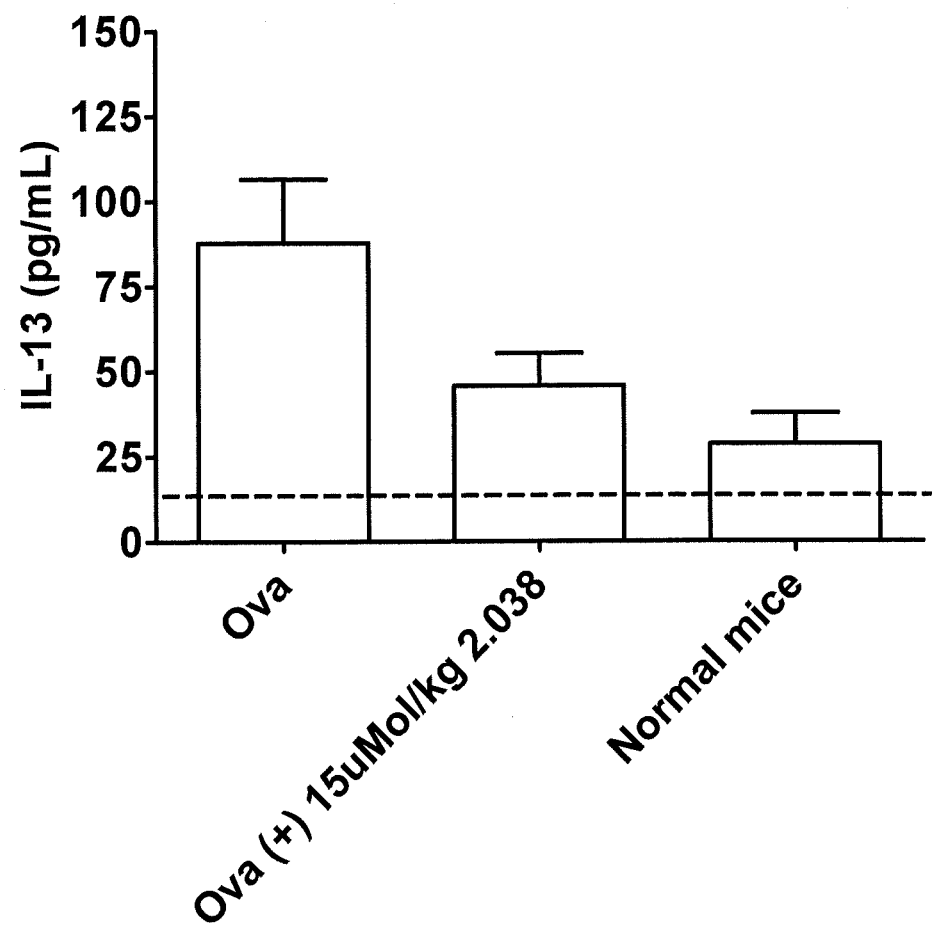
FIG. 8 shows the concentration of IL-13 (pg/mL) in BALF of (1) ova-sensitized, ova-challenged mice, (2) ova-sensitized, ova-challenged mice treated with Compound 2.038 (15 μmol/kg/oral), and (3) normal, saline-sensitized mice. Dashed line indicates the lower limit of detection for the cytokine of interest. Data represent mean±SEM, n=10 for ova-sensitized, ova-challenged mice, treated or untreated; n=5 for normal mice.

FIGS. 6-8 show the concentration of IL-5, Eotaxin, and IL-13 in (1) ova-sensitized, ova-challenged mice, (2) ova-sensitized, ova-challenged mice treated with Compound 2.038 (15 µmol/kg/oral on days 27 to 31), and (3) normal, saline-sensitized mice. The results showed that ova-sensitized, ova-challenged mice treated with Compound 2.038 had reduced levels of IL-5, Eotaxin, and IL-13.

Example 13

Prevention of Airway Hyperreactivity Development Via Decrease in Inflammation

Relevance

Airway hyperreactivity is a downstream physiologic effect of inflammation in the mouse ovalbumin sensitization model. The objective of the experiment was to answer whether the decrease in inflammation due to ROCK inhibitor anti-inflammatory dosing results in the prevention of downstream physiological consequences as measured by Penh. Although this concept is demonstrated in a model of airway hyperreactivity due to pulmonary inflammation, these data support the general use of these compounds as anti-inflammatory agents to prevent the downstream physiological consequences of inflammation in an in vivo model.

Protocol

Mouse model of ovalbumin sensitization was created as described in Example 13. The anti-inflammatory dosing paradigm (FIG. 3) was utilized to evaluate the prevention of airway hyperreactivity due to the anti-inflammatory effects of experimental compounds. The anti-inflammatory dosing paradigm consists of dosing the animals once a day starting on day 27 and finishing on either day 30 or 31 (1 hr prior to the aerosolized ovalbumin challenges on days 28 to 30) but not on day 32 when hyperreactivity evaluation occurs. On day 32 of the experiment, airway hyperreactivity was evaluated by placing conscious, unrestrained animals in a whole body plethysmometer (Buxco Wilmington, N.C.) and exposing them to escalating doses of nebulized methacholine, a known bronchial constrictor which acts through the muscarinic receptors of the lungs, (doses: 0.325-50 mg/ml). Exposure to the methacholine doses consisted of a 3 minute period during which a nebulizer was aerosolizing the methacholine and an additional 3 minute period following the cessation of nebulization. Over this 6 minute period, the plethysmometer monitors and generates numerical values for all parameters of the breath pattern. Enhanced pause (Penh), a unitless index of airway hyperreactivity, is derived from the expiratory side of the respiratory waveform measured via the plethysmograph and is used as an indirect measure of airway resistance and hyperreactivity. Penh is an indicator of changes in resistance within the airways and has been shown to be a valid marker for airway responsiveness to allergen challenge (Hamelmann, et al. *Am J Respir Crit. Care Med.* 1997; 156:768-775). Following the methacholine dose response, BALF was collected and all animals were anesthetized, bled and euthanized.

10(AUC). p values of less than 0.05 were considered statistically significant Computations were performed using PROC MIXED (SAS Version 9.1).

For Table 3, Penh values are reported as log 10 transformed AUC values. For FIG. 9, linear AUC values from compound treated mice were reported as a percent of linear AUC values from vehicle-treated ovalbumin-sensitized/ovalbumin-challenged (asthmatic) mice.

Figure 9:
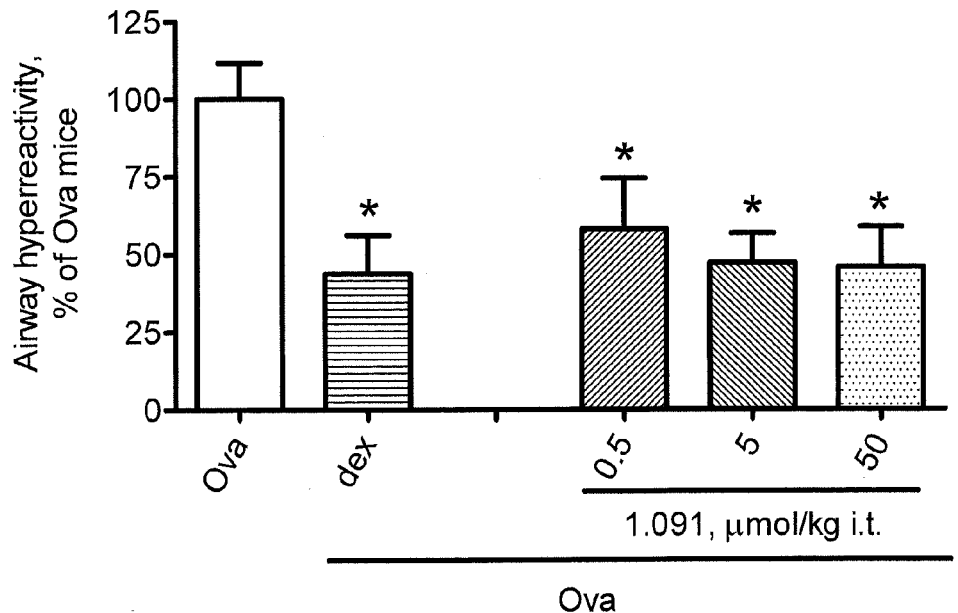
FIG. 9 shows the dose response effect of Compound 1.091 on airway hyperreactivity when dosed using the anti-inflammatory dosing paradigm on Days 27 to 30. *, p<0.05 using statistical analysis described in Example 13

The oral administration of 15 µMol/kg of Compound 1.131 or 2.038 once a day during days 27 to 31 resulted in prevention of airway hyperreactivity to metacholine dosed on Day 32 (Table 3). As shown in FIG. 9 and Table 3, intratracheal administration of Compound 1.091 once a day during days 27 to 30 (FIG. 9) or Compounds 1.161, 2.066 or 2.059 once a day during days 27 to 31 (Table 3) according to the anti-inflammatory dosing paradigm shown in FIG. 3 resulted in prevention of airway hyperreactivity. Compound 1.091, 1.161, 2.066 or 2.059 had similar efficacy to dexamethasone, a corticosteroid anti-inflammatory control. These data support the use of these compounds to prevent the downstream physiologic consequences of inflammation.

TABLE 3

Anti-inflammatory dosing: Statistical Analysis of the AUC for Average Penh Values Determined During Experiment Normalized to Baseline for Each Animal

| | Dosing concentration/ route of administration | Number of animals per group | log10AUC (Penh) | Standard Error | Student t-test p-value |
|---|---|---|---|---|---|
| asthmatic | Vehicle/oral | 70 | 2.3354 | 0.04751 | |
| 1.131 | 15 µmol/kg/oral | 10 | 2.0674 | 0.1061 | 0.0133 |
| 2.038 | 15 µmol/kg/oral | 20 | 1.8981 | 0.07966 | <0.0001 |
| 1.161 | 0.5 µmol/kg/ intratracheal | 10 | 2.0405 | 0.1083 | 0.0077 |
| 2.066 | 0.5 µmol/kg/ intratracheal | 10 | 2.0248 | 0.1091 | 0.0055 |
| 2.059 | 0.5 µmol/kg/ intratracheal | 10 | 1.9979 | 0.1084 | 0.0024 |
| Y-27632 | 30 µmol/kg/oral | 10 | 1.9942 | 0.1062 | 0.0017 |
| Dexamethasone | 1 mg/kg/oral | 30 | 2.0216 | 0.06546 | <0.0001 |
| non-asthmatic | Vehicle/oral | 20 | 1.7810 | 0.07973 | <0.0001 |

Statistical Methods

Within each experiment, a mouse was given a single compound and exposed to increasing doses of methacholine [0 (baseline), 0.375, 0.75, 1.5, 3, 6, 12, 25, 50 mg/ml]. The Penh value at each of the dose levels of methacholine represents the 6-minute average response. Change from baseline (CFB) in Penh was calculated at each methacholine dose and the area under the curve (AUC) for these CFB values was calculated using the trapezoidal rule. This same approach was applied for each mouse across multiple experiments.

For statistical analyses, a linear mixed-effects model where the response was the log 10 transformed value of AUC described above was used. Data from equal experimental conditions across experiments performed on different days were pooled for statistical analysis and data reporting. The various compounds were compared adjusting for the log 10-transformed baseline value of Penh and the chamber (1 of 10) of the plethysmometer each mouse was contained in during an experiment. A random intercept for each experiment was assumed to account for possible similarities of the results obtained from a given experiment (i.e., as a "blocking effect"). Pairwise comparisons of the compounds were performed using approximate t-tests to test the null hypothesis of no compound difference of the least-squares means of log Compounds were administered on days 27 to 31 according to the anti-inflammatory dosing paradigm. The t-test was conducted for the comparison of compound-treated to vehicle-treated "asthmatic groups" based on the vehicle which was run in every study.

Example 14

Human Neutrophil Chemotaxis

Relevance

Neutrophils are thought to contribute actively to the pathogenesis inflammatory diseases. This assay is an in vitro assay of neutrophil chemotaxis that can be used to evaluate the ability of Rho Kinase inhibitor compounds of Formula I or II to inhibit the migration of human neutrophils and their contribution to the inflammatory process.

Protocol

Peripheral blood from healthy human volunteers was collected and the neutrophils were isolated by Ficoll-paque density centrifugation followed by dextran sedimentation and hypotonic lysis of the red blood cells. Neutrophil chemotaxis was assessed using a modified Boyden Chamber (Neuroprobe, 96-well) with a 3 µm pore polycarbonate membrane.

The ability of the tested compounds to block chemotaxis induced by a 1 µM fMLP challenge during a one hour incubation at 37° C. with 5% $CO_2$ was assessed in a dose response manner. The results are shown in Table 4.

The results demonstrate that Rho Kinase inhibition by Formula I or II compounds inhibited human neutrophil migration toward a chemotactic stimulant in vitro with $IC_{50}$ potencies ranging from less than 1 µM to nearly 24 µM (Table 4).

TABLE 4

Inhibition of fMLP-induced neutrophil chemotaxis by Rho kinase inhibitors.

| Compound | Chemotaxis Avg $IC_{50}$, nM | Chemotaxis SEM, nM |
| --- | --- | --- |
| 2.038 | 734 | 367 |
| Y-39983 | 1,390 | 803 |
| 1.131 | 1,587 | 916 |
| 2.039 | 1,643 | 949 |
| 2.025 | 1,650 | 636 |
| 1.138 | 1,850 | 212 |
| 1.091 | 2,332 | 2,077 |
| 1.136 | 2,600 | 424 |
| 1.092 | 2,747 | 1,586 |
| 2.036 | 2,767 | 1,597 |
| 1.123 | 3,050 | 778 |
| 1.124 | 3,402 | 1,964 |
| 2.026 | 3,800 | 2,970 |
| H-1152 | 4,350 | 1,202 |
| 1.087 | 4,500 | 2,598 |
| 2.034 | 4,733 | 2,733 |
| 1.034 | 5,601 | 3,234 |
| 2.035 | 6,600 | 3,811 |
| Y-27632 | 6,765 | 1,747 |
| Fasudil | 23,800 | 13,741 |

Example 15

Human and Murine Eosinophil Chemotaxis

Relevance

Eosinophils are known to play a pivotal role in the pathogenesis of allergy and inflammation. Eosinophils are a major source of growth factors, lipids, basic granule proteins, cytokines and chemokines that contribute to allergy inflammation.

Protocol and Results

Human Eosinophil Isolation: Peripheral blood from healthy human volunteers was collected and the PMNs separated via Ficoll-paque density centrifugation followed by hypotonic lysis of the red blood cells. Subsequently, the human eosinophils were isolated from the cell suspension via StemCell Technologies Human Eosinophil Enrichment kit (Cat. No 19256) according to the manufacturer's recommendations. Briefly, unwanted cells were specifically labeled with dextran-coated magnetic nanoparticles using bispecific Tetrameric Antibody Complexes (TAC) directed against cell surface antigens on human blood cells: CD2, CD3, CD14, CD16, CD19, CD20, CD36, CD56, CD123, glycophorin A and dextran. The unwanted cells are then separated from the unlabelled eosinophils using the EasySep® magnetic isolation procedure.

Mouse Eosinophil Isolation: Bronchoalveolar lavage was collected from ovalbumin sensitized and challenged mice in a volume of 2.5 mL lavage buffer. The lavage buffer was 0.9% saline with 10% fetal bovine serum. The pooled lavages were maintained on ice until use. The murine eosinophils were isolated using MACS cell separation (Miltenyi Biotech) by depletion of B cells and T cells by positive selection following incubation with antibody conjugated magnetic beads specific for CD45-R (B220) and CD90 (Thy 1.2), which bind B cells and T cells, respectively.

Figure 10:
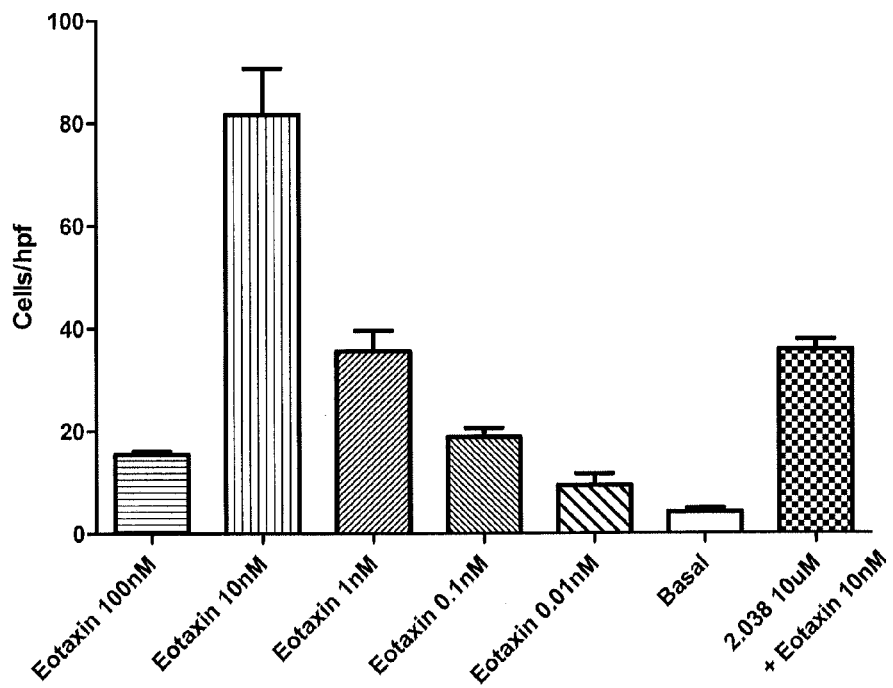
FIG. 10 shows the murine eosinophil chemotaxis. The data reported are mean number of migrated eosinophils per high power view field±SEM. Average of at least 2 view fields per well is presented, each treatment ran in triplicate.
Figure 11:
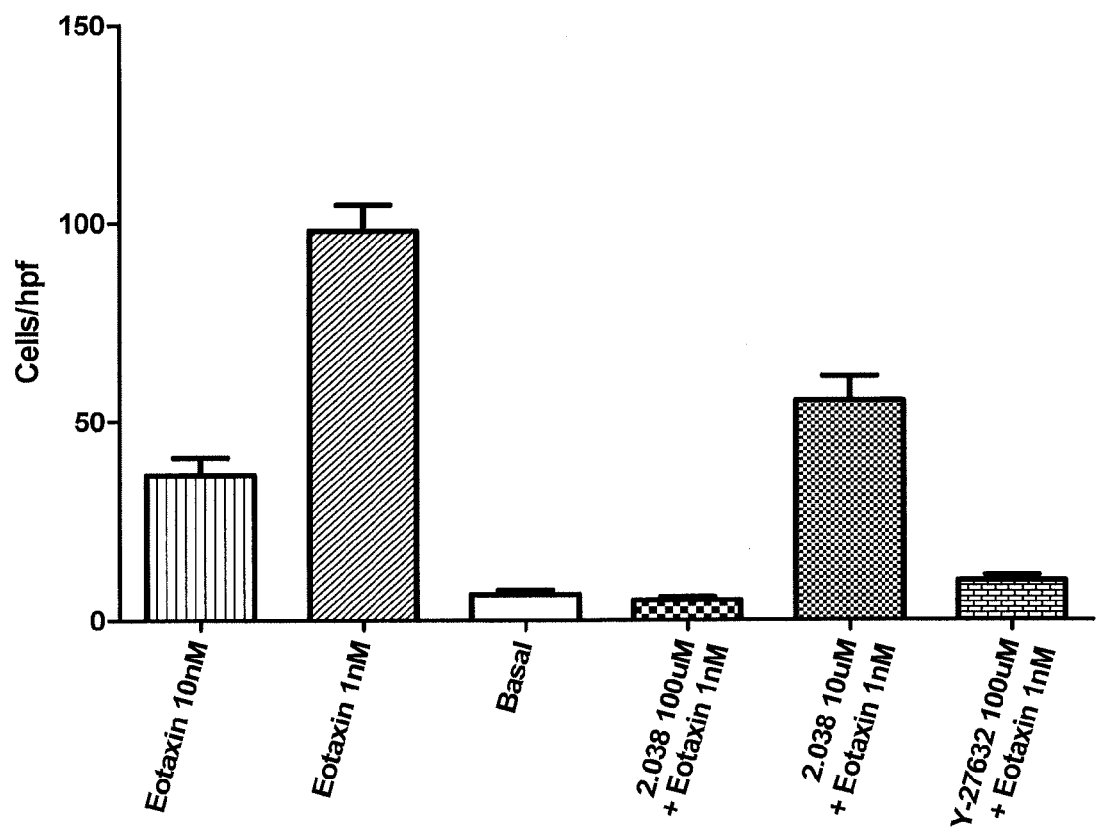
FIG. 11 shows the human eosinophil chemotaxis. The data reported are mean number of migrated eosinophils per high power view field±SEM. Average of at least 3 view fields per well is presented, each treatment ran in duplicate.

In Vitro Chemotaxis: Eosinophil chemotaxis was assessed using a modified Boyden Chamber (Neuroprobe, 96-well) with a 5 µm pore membrane. The ability of the tested compounds to block chemotaxis induced by a 10 nM eotaxin challenge (mouse) or 1 nM eotaxin challenge (human) during one hour incubation at 37° C. with 5% $CO_2$ was assessed. Chemotaxis was quantified via microscopy by counting the number of migrated cells in at least 3 view fields per treatment. The results are shown in FIGS. 10 and 11. FIG. 10 demonstrates that chemotaxis was induced by eotaxin in murine eosinophils; the chemotactic response was subsequently inhibited by Rho Kinase inhibitor Compound 2.038. FIG. 11 demonstates that chemotaxis was induced by eotaxin in human eosinophils. The chemotactic response was subsequently inhibited by Rho Kinase inhibitor Compound 2.038.

Example 16

Human Monocyte Cytokine Secretion Assay

Relevance:

This assay demonstrates a compound's ability to inhibit the secretion of multiple pro-inflammatory cytokines from human monocytes. Reduction in the levels of pro-inflammatory cytokines is associated with improvement in disorders with an inflammatory component.

Protocol

Peripheral blood from healthy human volunteers was collected and the monocytes isolated via Ficoll-paque density centrifugation. Monocytes were purified via an Easy Sep© Monocyte Enrichment Kit (Product number 19059) according to the manufacturer's instructions. The purified monocytes were then plated in 96-well plates at a density of 300,000 cells/mL in RPMI 1640+10% heat inactivated FBS media. The cells were allowed to pre-incubate with test compound at the indicated concentration for 30 minutes (37° C., 5% $CO_2$, humidified air); after which the supernatant was removed and media containing compound and 1 ng/mL LPS was added. Cells were allowed to incubate with compounds and LPS for 4 hours at 37° C. after which the supernatant was removed and stored at −80° C. Cytokine concentrations in the supernatant were determined using commercially available Bio-Rad Bio-plex™ kits according the manufacturer's instructions.

Results:

Compounds of Formulae I and II inhibit the release of multiple cytokines from human monocytes when incubated at 10 µM concentration in vitro, as shown in Table 5. Shown further in Table 6, potency determinations on compounds 2.059 and 2.066, both potent inhibitors of ROCK1 and ROCK2 and both of the chemical class in which $R_2$ is $R_2$-2, dose-dependently reduced the secretion of IL-1β, TNF-α and IL-9 from LPS-stimulated human monocytes, with potencies ranging from approximately 170 nM to 1 µM.

TABLE 5

Percent inhibition values for inhibition of cytokine secretion at 10 µM of test compound

| Compound | IL-1β % | IL-6 % | TNF-α % |
| --- | --- | --- | --- |
| 1.072 | 98.2 | 96.1 | 83.8 |
| 1.074 | 43.9 | 96.0 | 87.7 |

TABLE 5-continued

Percent inhibition values for inhibition of cytokine secretion at 10 μM of test compound

| Compound | IL-1β % | IL-6 % | TNF-α % |
|---|---|---|---|
| 1.075 | 49.7 | 73.9 | 51.6 |
| 1.076 | 51.0 | 81.2 | 78.9 |
| 1.077 | 30.3 | 43.3 | 52.3 |
| 1.078 | 60.4 | 111.0 | 88.1 |
| 1.079 | 59.3 | 31.1 | 56.5 |
| 1.091 | 165.5 | 108.2 | 104.6 |
| 1.093 | 109.0 | 49.7 | 76.1 |
| 1.106 | 121.5 | 95.0 | 80.6 |
| 1.107 | 111.3 | 122.1 | 83.1 |
| 1.108 | 131.3 | 89.8 | 116.7 |
| 1.109 | 190.5 | 312.9 | 118.3 |
| 1.110 | 133.6 | 111.7 | 118.6 |
| 1.123 | 82.6 | 64.7 | 62.7 |
| 1.124 | 99.5 | 101.4 | 61.5 |
| 1.127 | 198.0 | 67.3 | 97.3 |
| 1.131 | 48.3 | 68.6 | 85.2 |
| 1.132 | 58.6 | 72.5 | 80.3 |
| 1.133 | 54.5 | 70.7 | 66.2 |
| 1.134 | 43.2 | 74.6 | 69.1 |
| 1.135 | 57.0 | 123.2 | 108.0 |
| 1.136 | 66.3 | 95.0 | 71.5 |
| 1.137 | 40.3 | 46.2 | 58.0 |
| 1.138 | 257.4 | 76.6 | 130.9 |
| 1.141 | 50.4 | 71.7 | 75.7 |
| 1.142 | 82.8 | 40.7 | 68.6 |
| 1.143 | 76.8 | 130.5 | 66.4 |
| 1.145 | 129.2 | 95.1 | 88.9 |
| 1.146 | 85.2 | 128.0 | 97.7 |
| 1.148 | 63.9 | 78.6 | 56.1 |
| 1.149 | 69.8 | 121.5 | 119.9 |
| 1.150 | 78.2 | 89.2 | 94.4 |
| 1.151 | 84.5 | 114.1 | 88.9 |
| 1.152 | 74.7 | 94.7 | 120.1 |
| 1.153 | 64.1 | 106.2 | 74.3 |
| 1.154 | 52.3 | 104.4 | 86.4 |
| 1.155 | 76.7 | 121.8 | 79.7 |
| 1.156 | 60.7 | 92.5 | 70.5 |
| 1.157 | 121.4 | 92.6 | 65.1 |
| 1.158 | 80.8 | 133.1 | 86.6 |
| 1.159 | 97.1 | 84.8 | 76.1 |
| 1.161 | 87.7 | 86.3 | 153.5 |
| 1.162 | 95.5 | 99.8 | 158.7 |
| 1.163 | 166.7 | 140.9 | 91.6 |
| 1.164 | 80.1 | 109.5 | 89.0 |
| 1.165 | 129.9 | 114.3 | 103.5 |
| 1.166 | 107.0 | 87.2 | 82.2 |
| 1.170 | 80.6 | 72.7 | 67.8 |
| 1.171 | 78.9 | 91.8 | 72.2 |
| 1.173 | 86.1 | 79.5 | 80.1 |
| 1.175 | 29.3 | 38.2 | 47.4 |
| 1.176 | 95.2 | 112.4 | 72.4 |
| 1.183 | 68.7 | 123.3 | 76.5 |
| 1.185 | 39.8 | 63.0 | 66.6 |
| 1.186 | 64.1 | 105.3 | 68.2 |
| 1.195 | 115.4 | 94.4 | 67.7 |
| 1.197 | 179.1 | 128.8 | 83.3 |
| 1.200 | 0.0 | 0.0 | 0.2 |
| 1.206 | 88.7 | 164.0 | 97.3 |
| 1.208 | 62.0 | 109.0 | 92.0 |
| 1.212 | 116.3 | 111.0 | 108.1 |
| 1.213 | 111.1 | 81.7 | 77.4 |
| 1.215 | 136.7 | 63.2 | 60.4 |
| 1.217 | 118.6 | 73.8 | 71.3 |
| 1.219 | 138.9 | 127.7 | 82.1 |
| 1.223 | 117.0 | 88.5 | 60.7 |
| 1.226 | 99.3 | 52.2 | 66.6 |
| 1.227 | 69.4 | 66.7 | 79.3 |
| 1.229 | 44.9 | 63.2 | 50.7 |
| 1.233 | 78.5 | 78.9 | 79.0 |
| 1.236 | 75.2 | 93.0 | 98.0 |
| 1.237 | 97.1 | 100.9 | 70.6 |
| 1.238 | 101.1 | 62.9 | 73.2 |
| 1.239 | 39.4 | 84.7 | 58.5 |
| 1.246 | 103.0 | 108.3 | 79.0 |
| 1.249 | 133.8 | 56.2 | 60.0 |
| 1.252 | 139.2 | 68.3 | 101.6 |
| 1.253 | 160.6 | 228.6 | 126.8 |
| 1.258 | 104.1 | 83.5 | 94.0 |
| 1.262 | 145.7 | 156.6 | 135.3 |
| 2.026 | 166.0 | 180.7 | 109.1 |
| 2.031 | 49.0 | 89.3 | 66.4 |
| 2.038 | 90.8 | 79.7 | 70.2 |
| 2.039 | 49.8 | 70.3 | 47.8 |
| 2.054 | 24.0 | 56.8 | 37.9 |
| 2.058 | 1.2 | 1.3 | 10.6 |
| 2.059 | 0.3 | 0.0 | 6.9 |
| 2.060 | 5.9 | 19.6 | 33.0 |
| 2.064 | 14.3 | 45.7 | 66.2 |
| 2.066 | 0.0 | 0.0 | 25.2 |

TABLE 6

IC$_{50}$ values for inhibition of cytokine secretion

| | IL-1β (nM) | TNF-α (nM) | IL-9 (nM) |
|---|---|---|---|
| Compound 2.059 | 169.4 ± 13.0 | 207.1 ± 17.0 | 268.6 ± 28.1 |
| Compound 2.066 | 346.2 ± 182.3 | 610.6 ± 154.1 | 934.9 ± 407.5 |

Example 17

LPS-Induced Neutrophilia and Cytokine Production Assay

Relevance

Marked neutrophilia can occur upon tissue inflammation. The LPS-induced neutrophilia model is often used to determine the potential efficacy of therapeutic approaches to limit inflammatory responses. This assay is an in vivo assay of neutrophil accumulation and cytokine production that can be used to evaluate the activity of Rho Kinase inhibitor compounds of Formula I or II as anti-inflammatory agents in a whole animal model. Neutrophil accumulation and cytokine production are indicative of an inflammatory response and the activity of compounds to decrease neutrophil accumulation and cytokine production in this assay supports the use of these compounds to treat disorders with an inflammatory component Protocol Male BALB/c mice, approximately 19 to 21 grams, were ordered from Charles River Laboratories (Raleigh, N.C.). All animals were challenged with aerosolized LPS (10 μg/ml) for 25 minutes on study day 0, LPS aerosol was generated using an Aerogen Aeroneb nebulizer and controller providing a flow of 400 μl/min and a particle size of 2-4 μm MMAD. Rolipram was administered i.p at 20 mg/kg. Compound 1.091 or Compound 2.059 was administered intratracheally (i.t.) at 0.5-50 μmol/kg body weight one hour prior to LPS challenge. Four hours following LPS challenge, BALF was collected using a total of 3 ml of 0.9% sodium chloride containing 10% fetal calf serum. Total cell counts were determined using the Coulter Counter. For differential evaluations, BALF was centrifuged and cytospin slides prepared and stained with Hema3 stain. Manual leukocyte counts were then completed on 200 cells. The final concentration of individual leukocyte cell types per ml of BALF was determined by multiplication of the relative percentage of individual leukocytes with the total amount of cells/ml of BALF fluid. The concentration of IL-1β in the BALF samples was determined using commercially available Bio-plex kits (Bio-Rad). The analysis of cytokine levels was measured using the Bio-Plex 200 (Bio-Rad) system according to the manufacturer's instructions.

Results

Figure 12:
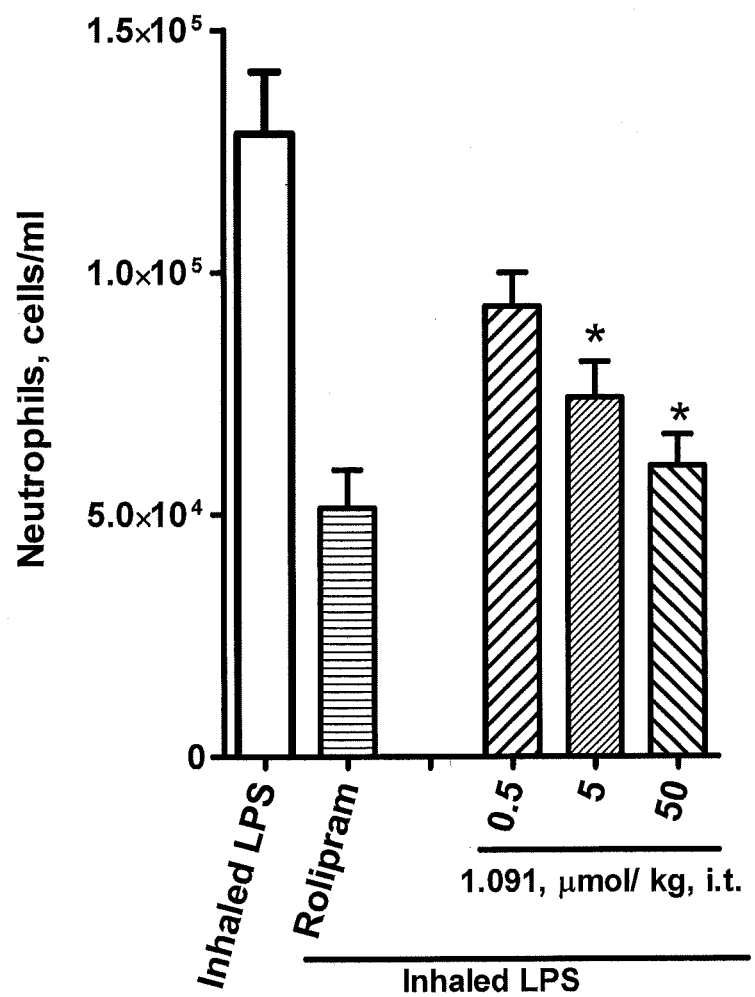
FIG. 12 shows the dose-dependent inhibition of LPS-induced neutrophilia by Compound 1.091 when dosed intratracheally to mice. Data are reported as cells/ml and are mean±SEM. *, p<0.05 when compared to LPS-treated mice using Student's t-test.
Figure 13:
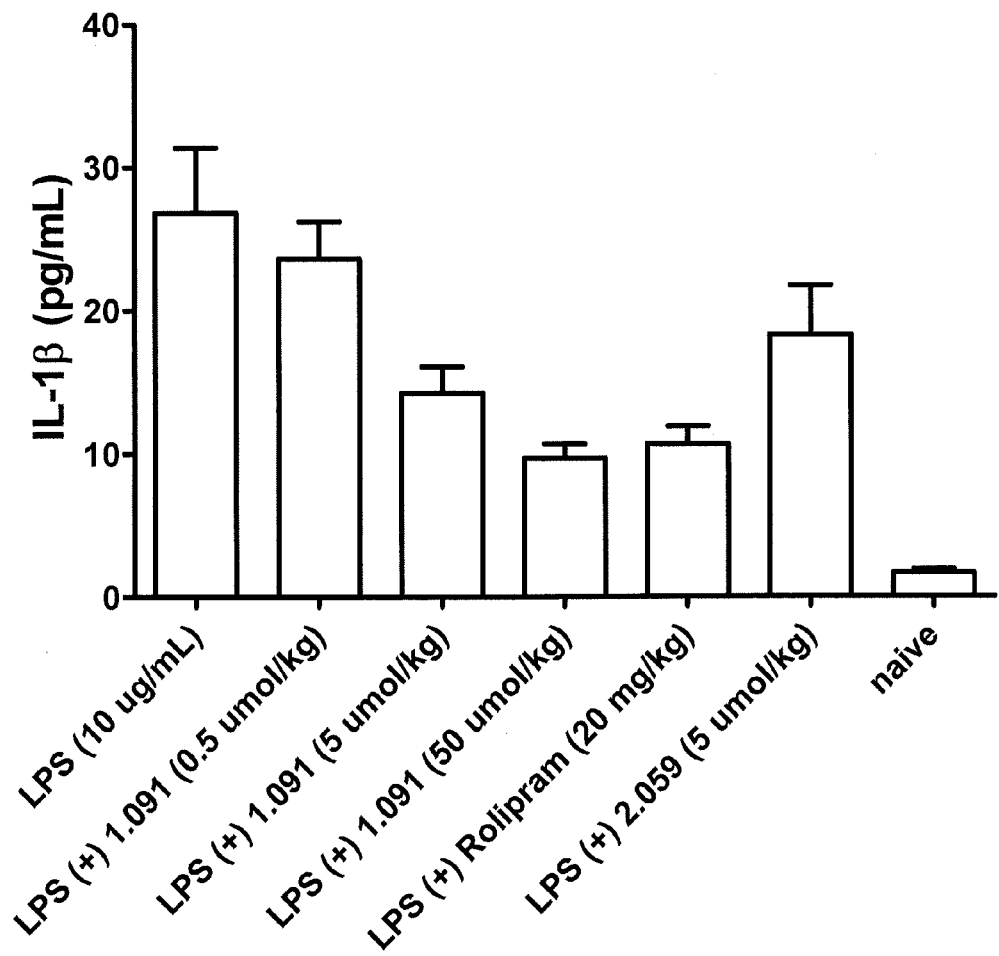
FIG. 13 shows the reduction of IL-1β levels in BALF from LPS-challenged mice upon intratracheal administration of Compound 1.091 or Compound 2.059. Data are reported as pg/mL of IL-1β and are mean±SEM.

FIG. 12 shows a significant reduction in pulmonary neutrophilia influx after intratracheal dosing of Compound 1.091. The efficacy of Compound 1.091 when dosed intratracheally is similar to the efficacy of the control compound rolipram dosed i.p. FIG. 13 shows the reduction in IL-1β after intratracheal administration of Compound 1.091 or Compound 2.059. These data demonstrate the efficacy of Rho kinase inhibitors of Formula I or II to inhibit inflammatory responses in vivo.

Example 18

PDGF-Stimulated Smooth Muscle Cell Proliferation Assay

Relevance:

This assay demonstrates a compound's ability to inhibit cellular proliferation induced by platelet derived growth factor (PDGF). Activity of compounds in the assay demonstrates the anti-proliferative properties of these compounds and supports the use of these compounds in the treatment of disorders associated with a proliferative component.

Protocol

Effects on cell proliferation were measured using a bromodeoxyuridine (BrdU) incorporation assay. A-10 rat thoracic aorta cells (ATCC #CRL 1476) were plated at 1000 cells per well in 96-well plates in Dulbecco's Modified Eagles Medium-High Glucose (Gibco cat. # 11995-065) containing 10% Fetal Bovine Serum (Sigma EC# 232-690-6) and allowed to grow for 24 hrs in an incubator at 37° C. Growth media was then removed and the cells were washed with warmed PBS (Gibco cat# 14190-144). Serum free media containing 0.1% BSA was added to the cells. 24 hours later the media was removed and replaced with warmed serum free media. Cells were treated with either 1 μM or 10 μM of test compound and incubated for 60 min at 37° C. prior to the addition of 10 ng/mL PDGF (BD Biosciences cat. # 354051) and placed in an incubator at 37° C. for 18 hrs with both compound and stimulant present. Proliferation was then monitored using the BrdU Cell Proliferation Assay, HTS (Calbiochem cat. # HTS01). BrdU was allowed to incorporate into cells for 24 hours prior to the addition of fixative/denaturing solution and the fluorometric detection of incorporated BrdU using a BrdU antibody as per manufacturer's directions. Data are reported as a percent of the PDGF-stimulated BrdU incorporation.

Results:

As shown in Table 7, compounds of Formulae I and II reduced PDGF-stimulated proliferation of A10 cells with efficacy ranging from 10-80% inhibition when dosed in vitro at 1 μM.

TABLE 7

Reduction of PDGF-stimulated proliferation of A-10 cells as a percent of the total challenge-stimulated proliferation.

| Compound | Percent of PDGF Induced Proliferation at 10 μM Avg | Percent of PDGF Induced Proliferation at 10 μM SEM | Percent of PDGF Induced Proliferation at 1 μM Avg | Percent of PDGF Induced Proliferation at 1 μM SEM |
| --- | --- | --- | --- | --- |
| 1.074 | 46.9 | 3.5 | 79.9 | 9.7 |
| 1.076 | 53.7 | 4.1 | 84.0 | 8.5 |
| 1.091 | 69.3 | 5.5 | 85.7 | 5.3 |
| 1.108 | 43.7 | 1.6 | 83.1 | 6.7 |
| 1.124 | 61.6 | 2.6 | 68.5 | 3.1 |
| 1.131 | 36.6 | 2.4 | 61.7 | 4.8 |
| 1.132 | 30.3 | 1.3 | 48.9 | 3.4 |
| 1.135 | 35.0 | 3.9 | 52.6 | 4.9 |
| 1.136 | 39.8 | 2.6 | 71.4 | 1.3 |
| 1.138 | 27.0 | 1.7 | 46.3 | 1.5 |
| 1.148 | 63.5 | 3.0 | 56.9 | 2.7 |
| 1.151 | 63.8 | 4.1 | 51.0 | 2.1 |
| 1.161 | 33.4 | 0.9 | 50.0 | 3.7 |
| 1.162 | 42.5 | 1.6 | 55.6 | 2.3 |
| 1.165 | 57.9 | 1.2 | 74.8 | 6.1 |
| 1.167 | 52.7 | 4.6 | 78.8 | 4.5 |
| 1.173 | 35.8 | 2.8 | 55.4 | 4.2 |
| 1.175 | 49.0 | 2.5 | 58.2 | 2.3 |
| 1.180 | 64.8 | 5.0 | 92.4 | 7.9 |
| 1.197 | 48.9 | 2.8 | 52.5 | 1.5 |
| 1.204 | 42.8 | 5.3 | 79.3 | 3.0 |
| 1.206 | 51.1 | 2.1 | 77.5 | 5.8 |
| 1.213 | 52.3 | 3.6 | 70.1 | 2.3 |
| 1.215 | 54.0 | 5.3 | 70.8 | 4.0 |
| 1.237 | 51.4 | 4.8 | 63.5 | 5.2 |
| 1.238 | 48.6 | 3.2 | 40.7 | 1.9 |
| 1.239 | 37.8 | 1.6 | 41.7 | 2.7 |
| 1.253 | 47.9 | 2.0 | 44.8 | 3.1 |
| 1.258 | 43.4 | 4.7 | 50.5 | 3.3 |
| 2.009 | 56.5 | 3.9 | 128.9 | 13.4 |
| 2.022 | 39.4 | 1.1 | 89.7 | 4.5 |
| 2.025 | 68.0 | 4.1 | 69.8 | 4.6 |
| 2.026 | 52.0 | 2.5 | 74.5 | 6.5 |
| 2.027 | 64.4 | 5.8 | 79.4 | 5.6 |
| 2.031 | 52.6 | 2.8 | 90.3 | 9.9 |
| 2.038 | 62.7 | 3.5 | 58.6 | 1.2 |
| 2.041 | 61.5 | 3.1 | 81.8 | 4.8 |
| 2.046 | 32.1 | 1.4 | 57.4 | 1.2 |
| 2.047 | 53.8 | 3.2 | 65.3 | 3.0 |
| 2.054 | 84.6 | 6.4 | 68.2 | 4.0 |
| 2.059 | 25.5 | 1.1 | 75.0 | 5.7 |
| 2.064 | 56.2 | 3.9 | 53.1 | 1.9 |
| 2.066 | 19.8 | 0.7 | 20.0 | 0.7 |

Example 19

Akt3 and p70S6K Inhibition Assay

Relevance

This assay demonstrates a compound's ability to inhibit the kinases Akt3 and p70S6K in vitro. Both kinases are known to play a role in proliferation pathways, Protocol Inhibition of Akt3 and p70S6K activity was determined using the IMAP™FP Progressive Binding Kit (Molecular Devices product number R8127). Akt3 human enzyme (Upstate Chemicon #14-502), or p70S6K human enzyme (Upstate Chemicon #14-486), and Flourescein tagged substrate peptide (Molecular Devices product number R7110) or (Molecular Devices product number R7184), for Akt3 and p70S6K respectively, was pre-incubated with test compound for 5 minutes in buffer containing 10 mM Tris-HCL pH 7.2, 10 mM $MgCl_2$, 1 mM DTT and 0.1% BSA. Following the pre-incubation, 30 μM ATP was added to initiate the reaction.

After 60 minutes at RT, Molecular Devices IMAP™ binding solution was added to bind phosphorylated substrate. After 30 minutes of incubation in the presence of the IMAP™ beads the fluorescence polarization was read and the ratio was reported as mP. $IC_{50}$ results were calculated using the Prism software from Graphpad. The $K_i$ values were determined according to the following formula: $K_i=IC_{50}/(1+([ATP\ Challenge]/EC_{50}\ ATP))$.

Results:

As shown in Table 8, many compounds of Formulae I and II show sub-micromolar inhibitory potencies against both Akt3 and p70S6K.

TABLE 8

Akt3 and p70S6K potency data

| Compound | Akt3 Ki, Avg, nM | Akt3 Ki, StdDev, nM | p70S6K Ki, Avg, nM | p70S6K Ki, StdDev, nM |
|---|---|---|---|---|
| 1.072 | 4752.1 | 617.1 | 1130.3 | 263.7 |
| 1.074 | 437.4 | 13.2 | 548.3 | 170.9 |
| 1.075 | 5321.5 | 61.8 | 974.6 | 166.8 |
| 1.076 | 240.9 | 6.2 | 414.3 | 162.7 |
| 1.077 | 5253.2 | 1422.9 | 715.5 | 291.5 |
| 1.078 | 3267.4 | 150.9 | 1678.1 | 640.4 |
| 1.079 | 7191.7 | 445.6 | 3012.8 | 963.8 |
| 1.091 | 5388.5 | 171.6 | 1420.4 | 78.5 |
| 1.093 | 1824.9 | 27.9 | 2025.6 | 356.8 |
| 1.106 | 3914.9 | 257.1 | 1329.1 | 268.0 |
| 1.107 | 16304.0 | 1575.9 | 3356.5 | 701.7 |
| 1.108 | 205.0 | 2.2 | 510.6 | 106.0 |
| 1.109 | 5190.9 | 318.3 | 2495.6 | 314.8 |
| 1.110 | 462.6 | 2.3 | 1298.2 | 175.9 |
| 1.123 | 2406.9 | 287.1 | 2810.7 | 597.6 |
| 1.124 | 7868.0 | 909.4 | 3325.3 | 542.0 |
| 1.127 | 975.4 | 126.4 | 2065.5 | 54.3 |
| 1.131 | 282.6 | 2.0 | 502.8 | 112.4 |
| 1.132 | 81.8 | 8.2 | 514.6 | 111.1 |
| 1.133 | 148.3 | 3.7 | 531.8 | 45.6 |
| 1.134 | 150.7 | 22.1 | 519.7 | 81.1 |
| 1.135 | 444.2 | 32.9 | 588.6 | 142.4 |
| 1.136 | 289.7 | 12.5 | 1236.7 | 413.1 |
| 1.137 | 197.9 | 10.3 | 353.6 | 132.2 |
| 1.138 | 91.3 | 48.3 | 443.5 | 36.3 |
| 1.141 | 1263.0 | 133.1 | 387.5 | 5.8 |
| 1.142 | 8268.5 | 702.6 | 2524.8 | 882.2 |
| 1.143 | 706.5 | 130.5 | 538.2 | 173.7 |
| 1.145 | 1190.5 | 63.5 | 2296.4 | 602.2 |
| 1.146 | 204.9 | 24.7 | 741.5 | 272.3 |
| 1.148 | 1131.4 | 161.7 | 435.5 | 138.0 |
| 1.149 | 7395.9 | 410.0 | 1888.4 | 661.8 |
| 1.150 | 3183.1 | 98.7 | 1273.8 | 106.7 |
| 1.151 | 708.9 | 112.8 | 530.7 | 69.6 |
| 1.152 | 1976.2 | 155.8 | 523.5 | 295.5 |
| 1.153 | 9950.2 | 2150.4 | 2376.1 | 553.3 |
| 1.154 | 4947.5 | 541.2 | 1130.1 | 355.3 |
| 1.155 | 5680.5 | 644.8 | 1751.6 | 502.8 |
| 1.156 | 8772.6 | 427.6 | 3244.6 | 675.0 |
| 1.157 | 29192.3 | 10235.1 | 8693.4 | 2357.4 |
| 1.158 | 5905.2 | 343.4 | 1971.7 | 454.0 |
| 1.159 | 1232.9 | 459.5 | 2061.8 | 271.7 |
| 1.161 | 63.5 | 3.6 | 129.4 | 73.5 |
| 1.162 | 92.0 | 0.9 | 387.4 | 217.4 |
| 1.163 | 4423.8 | 182.3 | 1875.2 | 496.6 |
| 1.164 | 4306.8 | 26.6 | 1957.4 | 729.2 |
| 1.165 | 4140.0 | 293.7 | 1627.1 | 584.4 |
| 1.166 | 18132.9 | 4816.3 | 5163.5 | 1419.0 |
| 1.167 | 8247.3 | 802.7 | 1071.0 | 516.6 |
| 1.170 | 7814.9 | 82.1 | 2046.3 | 580.9 |
| 1.171 | 9326.9 | 448.0 | 3419.0 | 841.6 |
| 1.173 | 157.0 | 0.5 | 339.7 | 204.4 |
| 1.175 | 2820.2 | 294.6 | 853.0 | 92.0 |
| 1.176 | 20941.5 | 4664.9 | 8755.7 | 3209.3 |
| 1.178 | 711.4 | 5.8 | 1116.2 | 637.4 |
| 1.180 | 12022.9 | 416.9 | 1029.2 | 139.1 |
| 1.183 | 9007.8 | 1662.8 | 2477.1 | 1431.3 |
| 1.185 | 4216.6 | 403.6 | 1152.2 | 761.8 |
| 1.186 | 10237.7 | 1867.1 | 1612.5 | 982.8 |
| 1.195 | 21975.8 | 379.4 | 2731.0 | 1192.9 |
| 1.197 | 64051.2 | 47694.4 | 8688.8 | 366.2 |
| 1.200 | 10608.5 | 131.2 | 3903.1 | 3979.1 |
| 1.204 | 1908.2 | 34.3 | 926.8 | 122.9 |
| 1.206 | 529.1 | 22.0 | 314.4 | 209.6 |
| 1.208 | 345.7 | 19.4 | 720.6 | 705.8 |
| 1.212 | 390.2 | 3.8 | 894.0 | 580.3 |
| 1.213 | 3207.8 | 140.6 | 2097.2 | 112.7 |
| 1.215 | 14753.0 | 1613.1 | 1285.8 | 108.5 |
| 1.217 | 10301.1 | 93.6 | 3501.9 | 3691.2 |
| 1.219 | 38297.7 | 11679.7 | 4969.9 | 1893.5 |
| 1.223 | 11139.0 | 1467.2 | 3101.9 | 1629.9 |
| 1.226 | 531.0 | 1.1 | 1348.5 | 1389.6 |
| 1.227 | 3476.0 | 196.6 | 1580.9 | 623.5 |
| 1.229 | 24557.8 | 17008.1 | 3128.5 | 322.4 |
| 1.233 | 2628.6 | 182.4 | 2004.9 | 815.1 |
| 1.236 | 3716.5 | 474.9 | 2755.4 | 2914.8 |
| 1.237 | 7910.2 | 217.5 | 9873.2 | 7272.6 |
| 1.238 | 4171.1 | 173.1 | 2609.6 | 1573.2 |
| 1.239 | 17657.7 | 4393.7 | 10026.9 | 8534.5 |
| 1.246 | 1096.1 | 9.5 | 1879.2 | 1883.4 |
| 1.249 | 1599.7 | 63.8 | 937.5 | 226.8 |
| 1.252 | 205.0 | 11.9 | 170.7 | 84.1 |
| 1.253 | 2597.1 | 29.9 | 2515.0 | 1464.8 |
| 1.258 | 315.2 | 94.1 | 531.5 | 229.6 |
| 1.262 | 861.0 | 1.0 | 5436.6 | 49.5 |
| 2.009 | 3725.8 | 198.3 | 1280.8 | 361.0 |
| 2.022 | 4115.1 | 209.4 | 501.1 | 6.9 |
| 2.025 | 966.4 | 103.5 | 498.8 | 74.2 |
| 2.026 | 2076.0 | 196.5 | 536.0 | 4.6 |
| 2.027 | 657.7 | 58.8 | 509.0 | 70.6 |
| 2.031 | 1357.9 | 0.6 | 326.4 | 52.7 |
| 2.038 | 2553.9 | 184.2 | 1397.4 | 345.6 |
| 2.039 | 1988.0 | 66.7 | 1010.3 | 195.5 |
| 2.041 | 3443.4 | 187.8 | 2095.1 | 161.9 |
| 2.046 | 1975.4 | 142.9 | 758.9 | 401.2 |
| 2.047 | 1942.1 | 163.1 | 437.5 | 184.9 |
| 2.054 | 414.8 | 5.7 | 438.9 | 207.3 |
| 2.055 | 977.5 | 72.3 | 311.6 | 180.9 |
| 2.058 | 1936.0 | 136.7 | 212.6 | 44.7 |
| 2.059 | 119.8 | 24.5 | 207.9 | 173.8 |
| 2.060 | 328.8 | 10.3 | 181.3 | 102.7 |
| 2.064 | 382.0 | 6.7 | 178.2 | 103.4 |
| 2.066 | 2510.4 | 30.5 | 368.3 | 133.1 |

Example 20

Kinase Panel Screen

Relevance

This assay demonstrates a compound's ability to inhibit members of a panel of kinases known to be involved in signaling pathways connected to inflammatory processes.

Protocol

Compounds of Formulae I and II were examined for activity against a selected panel of kinases using the KinaseProfiler™ enzyme profiling services (Upstate, Millipore Bioscience Division). Percent kinase activity at 10 μM and 1 μM test compound and 10 μM ATP was determined against 40 wild-type recombinant human kinases according to Upstate's standard protocol: ASK1, BTK, CSK, c-RAF, GCK, GSK3β, IKKα, IKKβ, IRAK1, IRAK4, JNK1α1, JNK2α2, JNK3, ERK1, ERK2, MAPKAP-$K_2$, MAPKAP-K3, MEK1, MKK4, MKK6, MKK7β, Mnk2, MSK1, PAK3, PDK1, PRAK, ROCK1, Rsk2, SAPK2a, SAPK2b, SAPK3, SAPK4, SRPK1, SRPK2, Syk, TAK1, TBK1, PI3-Kβ, PI3-Kγ, PI3-Kδ.

Results:

Percent inhibition results are reported in Table 9 for four compounds against six kinases in the panel. Only compounds in which $R_2$ is $R_2$-2 were found to inhibit significantly GCK, ERK1/2, Mnk2 and IRAK1/2. Only ERK1/2 were inhibited by ~50% at 1 µM by both compounds 2.059 and 2.066.

TABLE 9

Percent inhibition data for six of the tested kinases

|  | Compound 2.059 | | Compound 2.066 | | Compound 1.161 | | Compound 1.162 | |
| --- | --- | --- | --- | --- | --- | --- | --- | --- |
|  | 1 µM | 10 µM | 1 µM | 10 µM | 1 µM | 10 µM | 1 µM | 10 µM |
| ERK1 | 37 | 4 | 52 | 15 | 97 | 75 | 84 | 50 |
| ERK2 | 56 | 12 | 50 | 12 | 104 | 92 | 89 | 60 |
| Mnk2 | 49 | 12 | 99 | 54 | 108 | 106 | 111 | 65 |
| IRAK4 | 63 | 22 | 77 | 25 | 96 | 109 | 105 | 88 |
| IRAK1 | 87 | 30 | 74 | 32 | 106 | 99 | 100 | 97 |
| GCK | 75 | 34 | 39 | 7 | 96 | 91 | 93 | 75 |

Example 21

Rodent Pharmacokinetic Analyses of ROCK Inhibitors

Plasma (EDTA K2 anticoagulant) was collected from male, cannulated, CD Sprague Dawley rats to determine the pharmacokinetics of formulations containing compound inhibitors of Rho kinase. Each animal was dosed orally with a 4 ml/kg solution or suspension of each test compound in 10 mM acetate buffered saline, pH 4.5 at a final concentration range of 20-30 µmol/kg. Blood was collected at 0.25, 0.5, 1, 2, 4, 6, 8, and 24 hours. Plasma samples were assayed for the concentration of the test compound using an on-line, solid phase extraction LC/MS/MS analysis system.

Samples were analyzed on a QSTAR Elite, hybrid quadrupole time-of-flight mass spectrometer (Applied Biosystems, Framingham, Mass.) coupled with a Symbiosis Pharma integrated, on-line SPE-HPLC system (Spark Holland Inc., Plainsboro, N.J.). Analyst QS 2.0 software was used for instrument control, data acquisition and processing. An aliquot of each sample was injected onto a Luna C18 column (50×2 mm, 4 um, 80A, Phenomenex, Torrance, Calif.), and elution was carried out using a gradient from 2-98% acetonitrile. Mobile Phase A consisted of 0.1% ammonium hydroxide in water and Mobile Phase B consisted of 0.1% formic acid in acetonitrile. Pharmacokinetic analyses were performed using WinNonlin software version 5.2 (Pharsight Corporation, Mountain View, Calif.).

The pharmacokinetic results based on the observed plasma concentrations of the test compounds in rats are shown in Table 10.

TABLE 10

Pharmacokinetic results from rat oral PK studies (mean plasma values for n = 3 rats)

| Compound | Tmax (hr) | Cmax (nM) | AUC (0-last) (nM * hr) | t½ (hr) | Vz_F (L/kg) |
| --- | --- | --- | --- | --- | --- |
| 1.131 | 0.83 | 5610 | 10825 | 1.55 | 6.8 |
| 1.092 | 0.25 | 2101 | 1849 | 1.74 | 19.0 |
| 1.123 | 0.33 | 2044 | 2064 | 0.9 | 14.8 |
| 2.038 | 0.5 | 1037 | 1283 | 0.71 | 22.5 |
| 2.039 | 0.33 | 783 | 905 | 1.13 | 59.4 |
| 1.074 | 0.42 | 735 | 1167 | 0.86 | 45.7 |
| 1.107 | 1.67 | 544 | 1586 | 1.28 | 36.3 |
| 1.124 | 0.5 | 415 | 535 | 1.39 | 93.4 |
| 2.045 | 0.67 | 223 | 456 | 1.59 | 226 |
| 1.108 | 0.83 | 209 | 415 | 1.36 | 116 |
| 1.091 | BLQ | BLQ | BLQ | BLQ | BLQ |
| 2.026 | BLQ | BLQ | BLQ | BLQ | BLQ |
| 1.136 | BLQ | BLQ | BLQ | BLQ | BLQ |

BLQ indicates that the compound was below the limit of quantitation in the assay As determined from the plasma concentration versus time curves, the time to peak and peak exposure are represented by the values $T_{max}$ and $C_{max}$, respectively. The AUC values (nM*hr) shown were calculated as the areas under the plasma concentration versus time curves from time zero through the time of the last observable value and represent the total exposure of the compound over the course of the study. Half-life values or the amount of time required for the plasma levels of the compound to decline to half the initial value are represented as t1/2. The volume of distribution (Vz_F expressed in L/kg) relates the amount of theoretical volume needed to account for the observed concentration of a given dose of a compound. For rats, the total body water content is approximately 0.15 L/kg. Calculated volumes of distribution below 0.15 L/kg are considered low, whereas values between 5 and 100 L/kg are considered high. The volume of distribution varies depending on the degree of plasma protein binding as well as partitioning of the compound into fat and tissues. Table 10 provides evidence that our ROCK inhibiting compounds have a varying degree of pharmacokinetic properties that would allow them to be optimized for multiple routes of administration. These compounds are quickly absorbed, as indicated by a $T_{max}$ of generally less than 1 hour, with varying degrees of peak and total exposure as indicated by $C_{max}$ and AUC, with higher values indicating greater exposure. Regardless of exposure, these compounds demonstrate a similar clearance, t1/2.

Additionally, compound concentrations were determined in the plasma and lungs of male, ovalbumin-sensitized, Balb/c mice from a murine model of asthma. Test compounds were formulated in water or 1% polysorbate 80 and dosed at 15 µmol/kg for intraperitoneal (IP) or oral (PO) administration or formulated for intratracheal (IT) administration and dosed at 5 µmol/kg, which directly targets the lungs. Following completion of the in vivo study, mice were euthanized and blood and plasma collected approximately 2.5-3 hours post administration of test compound for bronchodilator (BD) studies and 24 hours post administration for anti-inflamatory (AI) studies. Lungs were homogenized in Matrix A lysing tubes using a FastPrep 24 tissue and cell homogenizer (MP Biomedicals, Solon, Ohio). Both plasma samples and lung extracts were assayed for compound concentrations using an on-line, solid phase extraction LC/MS/MS system. The actual lung tissue concentrations of each compound in mouse were extrapolated from the lung and plasma concentrations, data are shown in Table 11. The results of a set of experiments using unsensitized mice and collecting only plasma 15 minutes post administration of test compounds are shown in Table 12.

TABLE 11

Compound concentrations in ova-sensitized, ova-challenged mice lungs post IP, PO and IT administration (mean plasma corrected lung values for n = 9 or 10 mice)

| Compound | Efficacy Model | Route | Time Point, h | Lung, nM[1] |
|---|---|---|---|---|
| 1.131 | BD | PO | 3 | 7353 |
| 2.038 | BD | PO | 3 | 440 |
| 1.092 | BD | PO | 3 | 152 |
| 1.091 | BD | IP | 3 | 117 |
| 1.091 | BD | IT | 2.5 | 123 |
| 1.131 | AI | PO | 24 | 33 |
| 2.038 | AI | PO | 24 | 11 |

[1] for calculation of lung concentrations, it was assumed that 22.6% of the lung mass was plasma (R. H. Storey, Cancer Research, 943-947, 1951)

TABLE 12

Compound concentrations in mice at 15 min post administration (mean plasma values for n = 3 mice)

| Compound | Plasma Mean Concentration, nM | Plasma Concentration StdDev, nM |
|---|---|---|
| 1.072 | 1770.9 | 320.9 |
| 1.074 | 506.1 | 407.9 |
| 1.075 | 348.0 | 83.9 |
| 1.076 | 1715.0 | 474.9 |
| 1.077 | 25.9 | 0.2 |
| 1.078 | 1018.8 | 75.8 |
| 1.079 | 2442.5 | 302.9 |
| 1.090 | 5.9 | 5.2 |
| 1.091 | 333.8 | 82.7 |
| 1.092 | 314.3 | 60.4 |
| 1.093 | 362.6 | 148.7 |
| 1.106 | 441.4 | 146.7 |
| 1.107 | 211.1 | 129.5 |
| 1.108 | 394.5 | 9.0 |
| 1.109 | 187.2 | 36.0 |
| 1.110 | 792.0 | 311.9 |
| 1.123 | 71.4 | 11.8 |
| 1.124 | 118.0 | 2.4 |
| 1.126 | 0.0 | 0.0 |
| 1.127 | 980.2 | 757.5 |
| 1.131 | 444.5 | 130.0 |
| 1.132 | 982.4 | 207.7 |
| 1.133 | 1097.9 | 234.3 |
| 1.134 | 1550.8 | 623.9 |
| 1.135 | 656.8 | 115.4 |
| 1.136 | 25.9 | 6.3 |
| 1.137 | 556.9 | 279.8 |
| 1.138 | 1863.8 | 378.7 |
| 1.141 | 1643.1 | 368.6 |
| 1.142 | 329.7 | 171.6 |
| 1.143 | 274.5 | 68.8 |
| 1.145 | 109.0 | 117.9 |
| 1.146 | 1255.7 | 703.5 |
| 1.148 | 767.1 | 63.9 |
| 1.149 | 1559.4 | 789.6 |
| 1.150 | 1392.3 | 1278.3 |
| 1.151 | 478.6 | 173.6 |
| 1.152 | 435.4 | 44.5 |
| 1.153 | 521.5 | 61.3 |
| 1.154 | 1039.5 | 447.9 |
| 1.155 | 32.4 | 36.3 |
| 1.156 | 88.0 | 37.5 |
| 1.157 | 357.2 | 131.9 |
| 1.158 | 101.6 | 54.4 |
| 1.159 | 250.5 | 343.2 |
| 1.161 | 392.5 | 14.9 |
| 1.162 | 76.1 | 12.9 |
| 1.163 | 10.1 | 1.1 |
| 1.164 | 1504.3 | 580.6 |
| 1.165 | 93.5 | 49.6 |
| 1.166 | 342.4 | 118.1 |
| 1.168 | 587.5 | 258.9 |
| 1.170 | 638.6 | 154.7 |
| 1.171 | 368.8 | 208.9 |
| 1.172 | 111.1 | 32.0 |
| 1.173 | 144.4 | 72.6 |
| 1.175 | 1126.5 | 112.5 |
| 1.176 | 89.1 | 69.1 |
| 1.177 | 283.1 | 125.6 |
| 1.182 | 452.5 | 297.7 |
| 1.183 | 708.5 | 359.6 |
| 1.185 | 1023.6 | 492.8 |
| 1.186 | 2169.4 | 1599.1 |
| 1.191 | 260.0 | 58.8 |
| 1.193 | 55.4 | 26.0 |
| 1.194 | 355.0 | 133.5 |
| 1.195 | 107.9 | 23.1 |
| 1.197 | 453.1 | 354.0 |
| 1.198 | 643.2 | 112.1 |
| 1.200 | 0.0 | 0.0 |
| 1.202 | 129.7 | 71.9 |
| 1.203 | 1134.7 | 44.2 |
| 1.204 | 549.1 | 183.6 |
| 1.206 | 671.5 | 80.9 |
| 1.208 | 281.1 | 45.4 |
| 1.210 | 285.8 | 122.9 |
| 1.212 | 863.4 | 104.1 |
| 1.213 | 396.4 | 135.1 |
| 1.215 | 2651.2 | 529.0 |
| 1.217 | 292.5 | 176.0 |
| 1.219 | 1678.9 | 516.3 |
| 1.223 | 12.8 | 0.6 |
| 1.226 | 526.1 | 157.9 |
| 1.227 | 1859.4 | 603.7 |
| 1.229 | 1453.9 | 465.0 |
| 1.233 | 41.1 | 11.6 |
| 1.234 | 239.6 | 79.4 |
| 1.236 | 47.7 | 18.1 |
| 1.237 | 178.4 | 64.6 |
| 1.238 | 48.3 | 29.6 |
| 1.239 | 258.9 | 111.8 |
| 1.241 | 991.4 | 134.5 |
| 1.242 | 579.8 | 314.0 |
| 1.245 | 1524.0 | 127.5 |
| 1.246 | 587.4 | 299.7 |
| 1.249 | 2147.1 | 688.2 |
| 1.252 | 1259.2 | 1210.0 |
| 1.253 | 240.0 | 20.3 |
| 1.258 | 567.5 | 223.5 |
| 1.259 | 264.4 | 39.1 |
| 1.260 | 291.2 | 120.7 |
| 1.262 | 285.2 | 76.2 |
| 2.025 | 73.7 | 21.2 |
| 2.026 | 629.5 | 94.6 |
| 2.027 | 502.6 | 248.5 |
| 2.031 | 1430.4 | 139.2 |
| 2.034 | 664.7 | 649.4 |
| 2.036 | 1343.9 | 1603.3 |
| 2.038 | 728.9 | 222.8 |
| 2.039 | 92.0 | 47.6 |
| 2.041 | 986.5 | 287.0 |
| 2.043 | 60.8 | 24.7 |
| 2.046 | 488.1 | 96.1 |
| 2.047 | 3.0 | 1.7 |
| 2.054 | 765.5 | 214.3 |
| 2.055 | 656.1 | 172.6 |
| 2.056 | 1257.0 | 230.6 |
| 2.057 | 431.2 | 41.5 |
| 2.058 | 193.6 | 167.4 |
| 2.059 | 89.6 | 21.5 |
| 2.060 | 307.6 | 157.6 |
| 2.061 | 73.2 | 21.1 |
| 2.062 | 659.9 | 582.8 |
| 2.063 | 347.9 | 248.5 |

TABLE 12-continued

Compound concentrations in mice at 15 min post administration (mean plasma values for n = 3 mice)

| Compound | Plasma Mean Concentration, nM | Plasma Concentration StdDev, nM |
|---|---|---|
| 2.064 | 201.6 | 78.7 |
| 2.065 | 236.4 | 29.8 |
| 2.066 | 491.6 | |

The results of these quantitative analyses have enabled the selection of compounds for additional studies based on desirable pharmacokinetic profiles and preferential distribution in the target organ (lungs). We have identified compounds which possess high bioavailability and efficacy against airway hyperreactivity when dosed orally, as well as compounds that are efficacious when administered intraperitoneally or intratracheally, but do not reach systemic levels when dosed orally and thus are not efficacious by the oral route. Characterization of the pharmacokinetic properties and distribution of these Rho Kinase inhibitors is an essential part of the selection of compounds for drug development.

Example 22

Efficacy of Compounds of Formula I or II to Inhibit Proliferation of Primary Smooth-Muscle Like Cells Derived from Human LAM Patients Relevance This assay measures the ability of a compound to directly inhibit the proliferation of primary smooth-muscle like cells derived from human LAM patients. Activity of compounds in this assay supports the use of these compounds for the treatment of diseases with a proliferative component.

Protocol

LAM cells were dissociated from LAM nodules from the lung of patients with LAM who have undergone lung transplant. In brief, cells were dissociated by enzymatic digestion in M199 medium containing 0.2 mM $CaCl_2$, 2 mg/ml collagenase D, 1 mg/ml trypsin inhibitor, and 3 mg/ml elastase. The cell suspension was filtered and then washed with equal volumes of cold DF8 medium, consisting of equal amounts of Ham's F-12 and Dulbecco's modified Eagle's medium supplemented with $1.6 \times 10^{-6}$ M ferrous sulfate, $1.2 \times 10^{-5}$ U/ml vasopressin, $1.0 \times 10^{-9}$ M triiodothyronine, 0.025 mg/ml insulin, $1.0 \times 10^{-8}$ M cholesterol, $2.0 \times 10^{-7}$ M hydrocortisone, 10 pg/ml transferrin, and 10% fetal bovine serum. The cells were cultured in DF8 medium and were passaged twice per week. All LAM cells had a high degree of proliferative activity in the absence of any stimuli. Two separate LAM cell lines were tested and denoted as LAM1 or LAM2 cells. LAM cells in subculture during the 3rd through 12th cell passages were used. DNA synthesis was measured using a [$^3$H]thymidine incorporation assay. In brief, near-confluent cells that were serum-deprived for 48 h were incubated with 10 μM of compound or with vehicle (control). After 18 h of incubation, cells were labeled with [methyl-3H]thymidine for 24 hours. The cells were then scraped and lysed, and DNA was precipitated with 10% trichloroacetic acid. The precipitants were aspirated on glass filters and extensively washed and dried, and [$^3$H]thymidine incorporation was counted (Goncharova et al., Mol Pharmacol 73:778-788, 2008)

Results

Figure 14A:
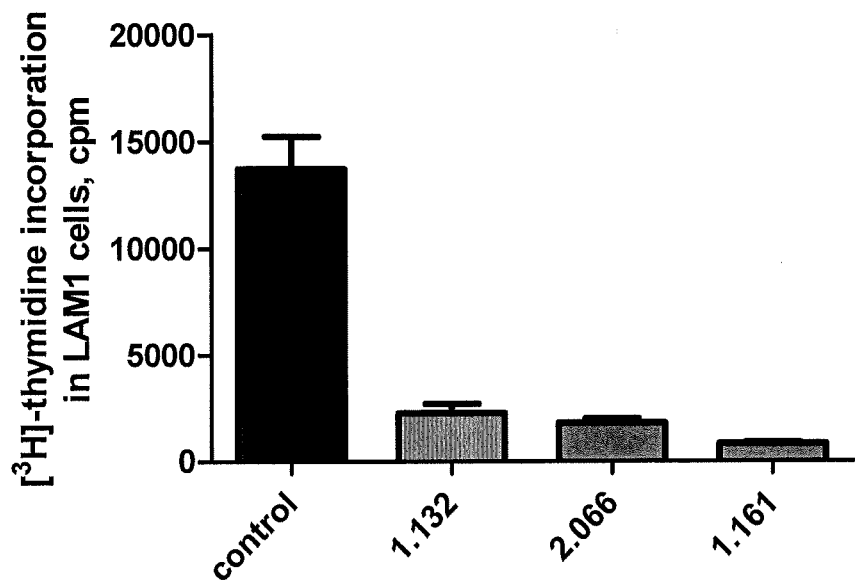
FIGS. 14A and 14B show [$^3$H]-thymidine incorporation in primary human LAM-derived cells. Cells were treated with vehicle alone (control) or with 10 μM of Compound 1.132, Compound 2.066 or Compound 1.161. Experiments were performed on two separate cell lines, LAM1 cells (FIG. 14A) and LAM2 cells (FIG. 14B). Data are reported as counts per minute (CPM) of incorporated [$^3$H]-thymidine and are mean±SEM.
Figure 14B:
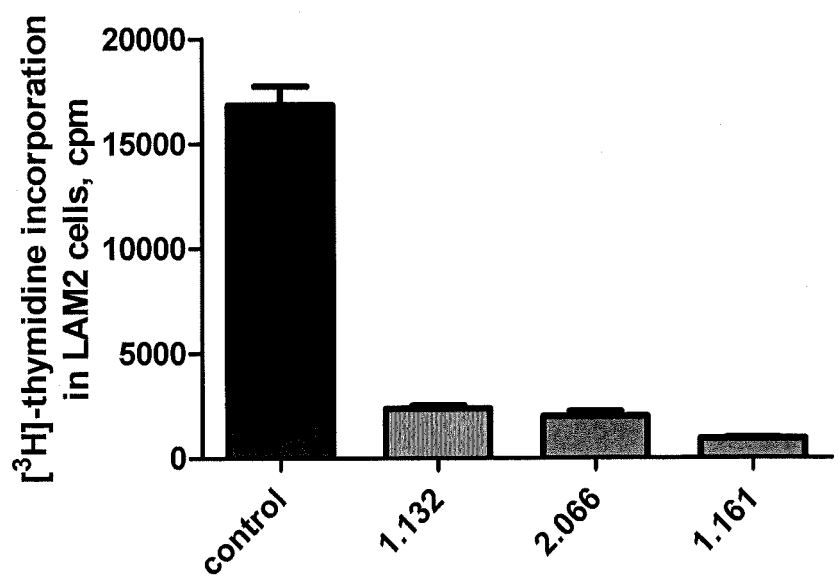

As shown in FIGS. 14A and 14B, compounds of Formula I and II reduced proliferation of LAM1 (FIG. 14A) and LAM2 (FIG. 14B) cells when dosed in vitro at 10 μM. These results demonstrate that Compounds of Formula I and II are efficacious in inhibiting the proliferation of primary cells.

Example 23

Summary of Data of Preferred Compounds

Principal biological data describing the preferred compounds of the invention have been collected into Table 13. Displayed in this table are ROCK1 and ROCK2 average Ki values in nM (as detailed in Example 1), Akt3 and p70S6K average Ki values in nM (as detailed in Example 19), average percent of PDGF stimulated proliferation at 10 and 1 μM of test compound (as detailed in Example 18), average percent of stimulated IL-1β, IL-6, and TNF-α secretion from human monocytes at 10 μM of test compound (as detailed in Example 16), average $IC_{50}$ for inhibition of fMLP-induced neutrophil chemotaxis in μM (as detailed in Example 14), mean compound plasma concentrations in mice at 15 minutes post oral administration (as detailed in Example 21).

TABLE 13

Summary of Data of Preferred Compounds

| Compound | ROCK1 Ki, nM | ROCK2 Ki, nM | Akt3 Ki, nM | p70S6K Ki, nM | Proliferation at 10 μM, % | Proliferation at 1 μM, % | IL-1β % | IL-6, % | TNF-α % | Chemotaxis IC50, μM | Mouse Oral PK, nM |
|---|---|---|---|---|---|---|---|---|---|---|---|
| 1.074 | 40.1 | 4.1 | 437.4 | 548.3 | 46.9 | 79.9 | 43.9 | 96.0 | 87.7 | | 506 |
| 1.075 | 48.7 | 4.4 | 5321.5 | 974.6 | | | 49.7 | 73.9 | 51.6 | | 348 |
| 1.076 | 14.3 | 2.6 | 240.9 | 414.3 | 53.7 | 84.0 | 51.0 | 81.2 | 78.9 | | 1715 |
| 1.077 | 76.1 | 11.1 | 5253.2 | 715.5 | | | 30.3 | 43.3 | 52.3 | | 26 |
| 1.079 | 71.5 | 4.7 | 7191.7 | 3012.8 | | | 59.3 | 31.1 | 56.5 | | 2443 |
| 1.091 | 71.4 | 3.3 | 5388.5 | 1420.4 | 69.3 | 85.7 | 165.5 | 108.2 | 104.6 | 2.3 | 334 |
| 1.093 | 64.5 | 7.7 | 1824.9 | 2025.6 | | 109.0 | 49.7 | 76.1 | | 363 | |
| 1.108 | 25.6 | 6.5 | 205.0 | 510.6 | 43.7 | 83.1 | 131.3 | 89.8 | 116.7 | | 395 |
| 1.109 | 58.8 | 9.6 | 5190.9 | 2495.5 | | | 190.5 | 312.9 | 118.3 | | 187 |
| 1.123 | 82.3 | 9.6 | 2406.9 | 2810.7 | | | 82.6 | 64.7 | 62.7 | 3.1 | 71 |
| 1.124 | 64.5 | 3.3 | 7868.0 | 3325.3 | 61.6 | 68.5 | 99.5 | 101.4 | 61.5 | 3.4 | 118 |
| 1.126 | 76.2 | 17.2 | | | | | | | | | 0 |
| 1.131 | 19.7 | 3.8 | 282.6 | 502.8 | 36.6 | 61.7 | 48.3 | 68.6 | 85.2 | 1.6 | 445 |
| 1.132 | 22.5 | 3.5 | 81.8 | 514.6 | 30.3 | 48.9 | 58.6 | 72.5 | 80.3 | | 982 |
| 1.133 | 25.0 | 4.3 | 148.3 | 531.8 | | | 54.5 | 70.7 | 66.2 | | 1098 |
| 1.134 | 22.4 | 4.4 | 150.7 | 519.7 | | | 43.2 | 74.6 | 69.1 | | 1551 |
| 1.135 | 40.3 | 5.4 | 444.2 | 588.6 | 35.0 | 52.6 | 57.0 | 123.2 | 108.0 | | 657 |
| 1.136 | 25.8 | 5.1 | 289.7 | 1236.7 | 39.8 | 71.4 | 66.3 | 95.0 | 71.5 | 2.6 | 26 |
| 1.137 | 36.3 | 7.2 | 197.9 | 353.6 | | | 40.3 | 46.2 | 58.0 | | 557 |

TABLE 13-continued

Summary of Data of Preferred Compounds

| Compound | ROCK1 Ki, nM | ROCK2 Ki, nM | Akt3 Ki, nM | p70S6K Ki, nM | Proliferation at 10 μM, % | Proliferation at 1 μM, % | IL-1β % | IL-6, % | TNF-α % | Chemotaxis IC50, μM | Mouse Oral PK, nM |
|---|---|---|---|---|---|---|---|---|---|---|---|
| 1.138 | 41.1 | 6.3 | 91.3 | 443.5 | 27.0 | 46.3 | 257.4 | 76.6 | 130.9 | 1.9 | 1864 |
| 1.141 | 28.5 | 3.8 | 1263.0 | 387.5 | | | 50.4 | 71.7 | 75.7 | | 1643 |
| 1.148 | 24.3 | 3.6 | 1131.4 | 435.5 | 63.5 | 56.9 | 63.9 | 78.6 | 56.1 | | 767 |
| 1.149 | 46.8 | 4.2 | 7395.9 | 1888.4 | | | 69.8 | 121.5 | 119.9 | | 1559 |
| 1.150 | 33.2 | 3.2 | 3183.1 | 1273.8 | | | 78.2 | 89.2 | 94.4 | | 1392 |
| 1.152 | 19.8 | 3.3 | 1976.2 | 523.5 | | | 74.7 | 94.7 | 120.1 | | 435 |
| 1.153 | 62.8 | 4.2 | 9950.2 | 2376.1 | | | 64.1 | 106.2 | 74.3 | | 522 |
| 1.155 | 45.4 | 7.0 | 5680.5 | 1751.6 | | | 76.7 | 121.8 | 79.7 | | 32 |
| 1.156 | 135.8 | 13.0 | 8772.6 | 3244.6 | | | 60.7 | 92.5 | 70.5 | | 88 |
| 1.157 | 263.8 | 8.8 | 29192.3 | 8693.4 | | | 121.4 | 92.6 | 65.1 | | 357 |
| 1.158 | 64.1 | 5.1 | 5905.2 | 1971.7 | | | 80.8 | 133.1 | 86.6 | | 102 |
| 1.161 | 9.9 | 2.5 | 63.5 | 129.4 | 33.4 | 50.0 | 87.7 | 86.3 | 153.5 | | 392 |
| 1.162 | 15.2 | 2.8 | 92.0 | 387.4 | 42.5 | 55.6 | 95.5 | 99.8 | 158.7 | | 76 |
| 1.163 | 33.6 | 2.9 | 4423.8 | 1875.2 | | | 166.7 | 140.9 | 91.6 | | 10 |
| 1.164 | 42.4 | 6.1 | 4306.8 | 1957.4 | | | 80.1 | 109.5 | 89.0 | | 1504 |
| 1.165 | 50.7 | 3.4 | 4140.0 | 1627.1 | 57.9 | 74.8 | 129.9 | 114.3 | 103.5 | | 94 |
| 1.166 | 95.2 | 8.0 | 18132.9 | 5163.5 | | | 107.0 | 87.2 | 82.2 | | 342 |
| 1.171 | 109.2 | 16.0 | 9326.9 | 3419.0 | | | 78.9 | 91.8 | 72.2 | | 369 |
| 1.173 | 15.1 | 3.6 | 157.0 | 339.7 | 35.8 | 55.4 | 86.1 | 79.5 | 80.1 | | 144 |
| 1.175 | 65.9 | 7.6 | 2820.2 | 853.0 | 49.0 | 58.2 | 29.3 | 38.2 | 47.4 | | 1126 |
| 1.176 | 314.3 | 11.2 | 20941.5 | 8755.7 | | | 95.2 | 112.4 | 72.4 | | 89 |
| 1.186 | 129.3 | 11.9 | 10237.7 | 1612.5 | | | 64.1 | 105.3 | 68.2 | | 2169 |
| 1.193 | 64.9 | 14.8 | | | | | | | | | 55 |
| 1.195 | 196.2 | 10.3 | 21975.8 | 2731.0 | | | 115.4 | 94.4 | 67.7 | | 108 |
| 1.197 | 120.2 | 5.0 | 64051.2 | 8688.8 | 48.9 | 52.5 | 179.1 | 128.8 | 83.3 | | 453 |
| 1.200 | 76.5 | 5.9 | 10608.5 | 3903.1 | | | 0.0 | 0.0 | 0.2 | | 0 |
| 1.206 | 64.4 | 9.1 | 529.1 | 314.4 | 51.1 | 77.5 | 88.7 | 164.0 | 97.3 | | 672 |
| 1.212 | 44.2 | 3.9 | 390.2 | 894.0 | | | 116.3 | 111.0 | 108.1 | | 863 |
| 1.213 | 106.3 | 3.0 | 3207.8 | 2097.2 | 52.3 | 70.1 | 111.1 | 81.7 | 77.4 | | 396 |
| 1.215 | 102.8 | 3.5 | 4753.0 | 1285.8 | 54.0 | 70.8 | 136.7 | 63.2 | 60.4 | | 2651 |
| 1.217 | 70.1 | 12.1 | 10301.1 | 3501.9 | | | 118.6 | 73.8 | 71.3 | | 293 |
| 1.219 | 343.6 | 15.4 | 38297.7 | 4969.9 | | | 138.9 | 127.7 | 82.1 | | 1679 |
| 1.223 | 239.5 | 15.7 | 11139.0 | 3101.9 | | | 117.0 | 88.5 | 60.7 | | 13 |
| 1.233 | 47.2 | 1.3 | 2628.6 | 2004.9 | | | 78.5 | 78.9 | 79.0 | | 41 |
| 1.236 | 49.3 | 2.1 | 3716.5 | 2755.4 | | | 75.2 | 93.0 | 98.0 | | 48 |
| 1.237 | 286.7 | 4.0 | 7910.2 | 9873.2 | 51.4 | 63.5 | 97.1 | 100.9 | 70.6 | | 178 |
| 1.238 | 61.2 | 1.5 | 4171.1 | 2609.6 | 48.6 | 40.7 | 101.1 | 62.9 | 73.2 | | 48 |
| 1.239 | 282.6 | 6.3 | 17657.7 | 10026.9 | 37.8 | 41.7 | 39.4 | 84.7 | 58.5 | | 259 |
| 1.249 | 91.7 | 8.6 | 1599.7 | 937.5 | | | 133.8 | 56.2 | 60.0 | | 2147 |
| 1.252 | 30.5 | 4.5 | 205.0 | 170.7 | | | 139.2 | 68.3 | 101.6 | | 1259 |
| 1.253 | 59.9 | 1.7 | 2597.1 | 2515.0 | 47.9 | 44.8 | 160.6 | 228.6 | 126.8 | | 240 |
| 1.258 | 9.5 | 1.3 | 315.2 | 531.5 | 43.4 | 50.5 | 104.1 | 83.5 | 94.0 | | 567 |
| 1.259 | 19.5 | 2.1 | | | | | | | | | 264 |
| 1.260 | 70.9 | 7.1 | | | | | | | | | 291 |
| 1.261 | 307.4 | 14.8 | | | | | | | | | |
| 1.262 | 54.9 | 4.0 | 861.0 | 5436.6 | | | 145.7 | 156.6 | 135.3 | | 285 |
| 1.270 | 130.5 | 9.9 | | | | | | | | | |
| 1.273 | 31.3 | 8.2 | | | | | | | | | |
| 1.275 | 401.7 | 14.1 | | | | | | | | | |
| 1.277 | 42.3 | 4.6 | | | | | | | | | |
| 1.281 | 71.8 | 7.4 | | | | | | | | | |
| 2.025 | 6.9 | 2.9 | 966.4 | 498.8 | 68.0 | 69.8 | | | | 1.7 | 74 |
| 2.026 | 38.0 | 13.0 | 2076.0 | 536.0 | 52.0 | 74.5 | 166.0 | 180.7 | 109.1 | 3.8 | 629 |
| 2.031 | 14.6 | 5.3 | 1357.9 | 326.4 | 52.6 | 90.3 | 49.0 | 89.3 | 66.4 | | 1430 |
| 2.038 | 28.9 | 6.3 | 2553.9 | 1397.0 | 62.7 | 58.6 | 90.8 | 79.7 | 70.2 | 0.7 | 729 |
| 2.039 | 18.8 | 6.7 | 1988.0 | 1010.3 | | | 49.8 | 70.3 | 47.8 | 1.6 | 92 |
| 2.041 | 30.8 | 9.6 | 3443.4 | 2095.1 | 61.5 | 81.8 | | | | | 987 |
| 2.046 | 16.7 | 5.6 | 1975.4 | 758.9 | 32.1 | 57.4 | | | | | 488 |
| 2.047 | 26.4 | 7.0 | 1942.1 | 437.5 | 53.8 | 65.3 | | | | | 3 |
| 2.054 | 17.1 | 3.7 | 414.8 | 438.9 | 84.6 | 68.2 | 24.0 | 56.8 | 37.9 | | 765 |
| 2.055 | 16.0 | 6.4 | 977.5 | 311.6 | | | | | | | 656 |
| 2.057 | 6.2 | 3.7 | | | | | | | | | 431 |
| 2.058 | 15.3 | 3.3 | 1936.0 | 212.6 | | | 1.2 | 1.3 | 10.6 | | 194 |
| 2.059 | 3.9 | 2.7 | 119.8 | 207.9 | 25.5 | 75.0 | 0.3 | 0.0 | 6.9 | | 90 |
| 2.060 | 4.9 | 3.2 | 328.8 | 181.3 | | | 5.9 | 19.6 | 33.0 | | 308 |
| 2.061 | 10.5 | 1.8 | | | | | | | | | 73 |
| 2.064 | 4.1 | 2.2 | 382.0 | 178.2 | 56.2 | 53.1 | 14.3 | 45.7 | 66.2 | | 202 |
| 2.065 | 4.1 | 1.8 | | | | | | | | | 236 |
| 2.066 | 10.2 | 2.3 | 2510.4 | 368.3 | 19.8 | 20.0 | 0.0 | 0.0 | 25.2 | | 492 |
| 2.067 | 19.6 | 4.2 | | | | | | | | | |
| 2.068 | 8.0 | 5.8 | | | | | | | | | |
| 2.069 | 16.7 | 2.4 | | | | | | | | | |
| 2.072 | 7.5 | 4.4 | | | | | | | | | |
| 2.073 | 12.7 | 4.2 | | | | | | | | | |
| 2.076 | 8.0 | 2.4 | | | | | | | | | |

TABLE 13-continued

Summary of Data of Preferred Compounds

| Compound | ROCK1 Ki, nM | ROCK2 Ki, nM | Akt3 Ki, nM | p70S6K Ki, nM | Proliferation at 10 μM, % | Proliferation at 1 μM, % | IL-1β % | IL-6, % | TNF-α % | Chemotaxis IC50, μM | Mouse Oral PK, nM |
|---|---|---|---|---|---|---|---|---|---|---|---|
| 2.077 | 33.7 | 5.0 | | | | | | | | | |
| 2.078 | 18.3 | 2.6 | | | | | | | | | |
| 2.079 | 18.5 | 2.3 | | | | | | | | | |
| 2.082 | 131.7 | 9.0 | | | | | | | | | |
| 2.096 | 70.2 | 9.6 | | | | | | | | | |
| 2.097 | 35.4 | 2.8 | | | | | | | | | |
| 2.099 | 15.0 | 3.8 | | | | | | | | | |

Although the invention has been described with reference to the presently preferred embodiments, it should be understood that various modifications could be made without departing from the scope of the invention.

What is claimed:

1. A method of treating diabetic nephropathy; the method comprises the steps of first identifying a subject suffering from diabetic nephropathy, then administering to the subject an effective amount of a compound of Formula II to treat diabetic nephropathy;

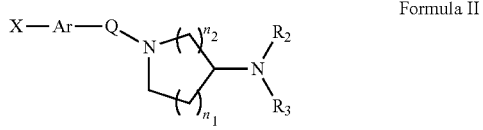

Formula II wherein:
Q is $(CR_4R_5)_{n3}$;
$n_1$ is 1;
$n_2$ is 1;
$n_3$ is 1, 2, or 3;
$R_2$ is $R_2$-2:

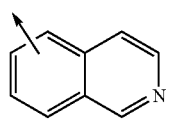

$R_2$-2

Ar is a monocyclic aryl or bicyclic aryl;
X is from 1 to 3 substituents on Ar, and each is independently selected from the group consisting of $OR_8$, $NR_8R_9$, $SR_8$, $SO_2NR_8R_9$, $NR_8SO_2R_9$, $CONR_8R_9$, $NR_8C(=O)R_9$, $NR_8C(=O)OR_9$, $OC(=O)NR_8R_9$, and $NR_8C(=O)NR_9R_{10}$;
$R_3$ is H, alkyl, alkenyl, alkynyl, cycloalkyl, cycloalkenyl, cycloalkylalkyl, cycloalkylalkenyl, or cycloalkylalkynyl, optionally substituted;
$R_4$ and $R_5$ are H;
$R_8$-$R_{10}$ are independently H, alkyl, alkenyl, alkynyl, aryl, arylalkyl, arylalkenyl, arylalkynyl, cycloalkyl, cycloalkenyl, cycloalkylalkyl, cycloalkylalkenyl, cycloalkylalkynyl, heteroaryl, heteroarylalkyl, heteroarylalkenyl, heteroarylalkynyl, (heterocycle)alkyl, (heterocycle)alkenyl, (heterocycle)alkynyl, or heterocycle; optionally substituted by one or more halogen or heteroatom-containing substituents selected from the group consisting of $OR_{11}$, $NR_{11}R_{12}$, $NO_2$, $SR_{11}$, $SOR_{11}$, $SO_2R_{11}$, $SO_2NR_{11}R_{12}$, $NR_{11}SO_2R_{12}$, $OCF_3$, $CONR_{11}R_{12}$, $NR_{11}C(=O)R_{12}$, $NR_{11}C(=O)OR_{12}$, $OC(=O)NR_{11}R_{12}$, and $NR_{11}C(=O)NR_{12}R_{13}$;
$R_{11}$-$R_{13}$ are independently H, alkyl, alkenyl, alkynyl, aryl, arylalkyl, arylalkenyl, arylalkynyl, cycloalkyl, cycloalkenyl, cycloalkylalkyl, cycloalkylalkenyl, cycloalkylalkynyl, heteroaryl, heteroarylalkyl, heteroarylalkenyl, heteroarylalkynyl, (heterocycle)alkyl, (heterocycle)alkenyl, (heterocycle)alkynyl, or heterocycle;
with the proviso that if X is acyclic and is connected to Ar by an oxygen or nitrogen atom, then X contains at least one additional oxygen, nitrogen or sulfur atom.

2. The method according to claim 1, wherein Ar is 3-substituted phenyl; 4-substituted phenyl; 3,4-disubstituted phenyl; or 2,3-disubstituted phenyl.

3. The method according to claim 1, wherein said compound is Compound 2.026, which is (R)—N-(1-(4-(methylthio)benzyl)pyrrolidin-3-yl)isoquinolin-5-amine; Compound 2.038, which is (R)—N-(3-((3-(isoquinolin-5-ylamino)pyrrolidin-1-yl)methyl)phenyl)methanesulfonamide; Compound 2.039, which is (R)-2-(3-((3-(isoquinolin-5-ylamino)pyrrolidin-1-yl)methyl)phenoxy)ethanol; Compound 2.040, which is (R)-2-(3-(3-(isoquinolin-5-ylamino)pyrrolidin-1-yl)methyl)phenoxy)acetamide; Compound 2.041, which is (R)—N-(3(3-(isoquinolin-5-ylamino)pyrrolidin-1-yl)methyl)phenyl)ethanesulfonamide; or Compound 2.044, which is (R)-2-(3-((3-(isoquinolin-5-ylamino)pyrrolidin-1-yl)methyl)phenoxy)acetic acid.

4. The method of claim 1, wherein Ar is phenyl.

5. The method of claim 1, wherein Q is $CH_2$.

6. The method of claim 4, wherein X is $OR_8$, or $NR_8SO_2R_9$.

7. The method of claim 6, wherein $R_8$ is H, alkyl, arylalkyl, cycloalkylalkyl, optionally substituted with $OR_{11}$, $NR_{11}SO_2R_{12}$, or $CONR_{11}R_{12}$.

8. A method of treating diabetic nephropathy; the method comprises the steps of first identifying a subject suffering from diabetic nephropathy, then administering to the subject an effective amount of Compound 2.038, which is (R)—N-(3-((3-(isoquinolin-5-ylamino)pyrrolidin-1-yl)methyl)phenyl)methanesulfonamide, to treat diabetic nephropathy.

9. The method of claim 1, wherein said compound is Compound 2.039, which is (R)-2-(3-((3-(isoquinolin-5-ylamino)pyrrolidin-1-yl)methyl)phenoxy)ethanol.

* * * * *